(12) United States Patent
Brody et al.

(10) Patent No.: US 9,499,820 B2
(45) Date of Patent: Nov. 22, 2016

(54) METHODS OF ELIMINATING OR REDUCING EXPRESSION OF GENES IN FILAMENTOUS FUNGAL STRAINS BY TRANSITIVE RNA INTERFERENCE

(75) Inventors: Howard Brody, Davis, CA (US);
Donna Moyer, Davis, CA (US);
Amanda Fisher, Davis, CA (US)

(73) Assignee: NOVOZYMES, INC., Davis, CA (US)

( * ) Notice: Subject to any disclaimer, the term of this patent is extended or adjusted under 35 U.S.C. 154(b) by 832 days.

(21) Appl. No.: 12/520,067

(22) PCT Filed: Dec. 20, 2007

(86) PCT No.: PCT/US2007/088447
§ 371 (c)(1),
(2), (4) Date: Aug. 11, 2009

(87) PCT Pub. No.: WO2008/080017
PCT Pub. Date: Jul. 3, 2008

(65) Prior Publication Data
US 2010/0055755 A1    Mar. 4, 2010

Related U.S. Application Data

(60) Provisional application No. 60/876,895, filed on Dec. 21, 2006.

(51) Int. Cl.
| | | |
|---|---|---|
| C12P 1/02 | (2006.01) | |
| C12N 1/15 | (2006.01) | |
| C12N 15/80 | (2006.01) | |
| C12N 15/113 | (2010.01) | |

(52) U.S. Cl.
CPC ...... *C12N 15/1137* (2013.01); *C12N 2310/111* (2013.01); *C12N 2310/14* (2013.01); *C12N 2310/53* (2013.01)

(58) Field of Classification Search
USPC ............. 435/6, 91.1, 91.21, 91.31, 6.1, 171, 435/254.11, 471; 536/23.1, 24.5, 24.3
See application file for complete search history.

(56) References Cited

U.S. PATENT DOCUMENTS

| | | | |
|---|---|---|---|
| 2006/0073500 A1* | 4/2006 | Peters et al. | 435/6 |
| 2009/0048111 A1* | 2/2009 | Huang et al. | 504/241 |
| 2010/0169996 A1* | 7/2010 | Navarro et al. | 800/21 |
| 2011/0152347 A1* | 6/2011 | Zamore et al. | 514/44 A |

FOREIGN PATENT DOCUMENTS

| | | |
|---|---|---|
| WO | WO 98/53083 | 11/1998 |
| WO | WO 01/49844 | 7/2001 |
| WO | WO 03/050288 | 6/2003 |
| WO | WO 2005-026356 | 3/2005 |
| WO | WO 2005/056772 | 6/2005 |

OTHER PUBLICATIONS

Alder et al., RNA J., vol. 9, pp. 25-32 (2003).*
Bleys et al., RNA J., vol. 1, pp. 1633-1639 (2006).*
Van Houdt et al., Plant Phisiology, vol. 131, pp. 245-253 (2003).*
Alder et al., 2003, *RNA J.* 9: 25-32.
Bailis and Forsburg, 2002, *Genome Biol.* 3, Reviews 1035.
Hammond and Baulcombe, 1996, *Plant Mol. Biol.* 32: 79-88.
Bernstein et al., 2001, *Nature* 409: 363.
Bleys et al., 2006, *RNA J.* 12: 1633-1639.
Bosher et al., 1999, *Genetics* 153: 1245-56.
Chi et al., 2003, *Proc. Natl. Acad. Sci. USA* 100: 6343-6346.
Elbashir et al., 2001, *Genes and Dev.* 15: 188.
Elbashir et al., 2001, *Nature* 411: 494.
Fabian et al., 2002, *Plant Cell* 14: 857-867.
Garcia-Perez et al., 2004, *The Plant Journal* 38: 594-602.
Grewal and Moazed, 2003, *Science* 301: 798-802.
Hammond et al., 2001, *Science* 293: 1146.
Hannon, 2002, *Nature* 418: 244-251.
Hoa et al., 2003, *Insect Biochemistry and Molecular Biology* 33: 949-957.
Kennerdell et al., 2000, *Nat. Biotechnol.* 18: 896-8.
McCaffrey et al., 2003, *Nat. Biotechnol.* 21: 639-44.
Matzke and Matzke, 1998, *Cell. Mol. Life. Sci.* 54: 94-103.
Morel et al., 2000, *Curr. Biol.* 10: 1591-1594.
Nykanen et al., 2001, *Cell* 197: 300.
Petersen et al., 2005, *Plant Molecular Biology* 58: 575-583.
Roignamt et al., 2003, *RNA J.* 9: 299-308.
Selker, 1997, *Trends Genet.* 13: 296-301.
Sijen et al., 2001, *Cell* 107: 465-476.
Vaistij et al., 2002, *The Plant Cell* 14: 857-867.
Van Houdt et al., 2003, *Plant Physiol.* 131: 245-253.
Voorhoeve and Agami, 2003, *Trends Biotechnol.* 21: 2-4.
Xi-Song Ke et al., 2003, *Current Opinion in Chemical Biology* 7: 516-523.
Fulci et al., 2007, Curr Op Microbiol 10, 199-203.
Goldoni et al., 2004, Fungal Gen Biol 41, 1016-1024.
Nicolas et al. 2003, Embo J 22 (15), 3983-3991.
Brummel et al, 2003, Plant J 33, 793-800.

* cited by examiner

*Primary Examiner* — Jane Zara
(74) *Attorney, Agent, or Firm* — Robert Starnes

(57) ABSTRACT

The present invention relates to methods of reducing or eliminating expression of a target gene in a filamentous fungal strain by transitive RNA interference.

8 Claims, 9 Drawing Sheets

METHODS OF ELIMINATING OR REDUCING EXPRESSION OF GENES IN FILAMENTOUS FUNGAL STRAINS BY TRANSITIVE RNA INTERFERENCE

CROSS-REFERENCE TO RELATED APPLICATIONS

This application is a 35 U.S.C. 371 national application of PCT/US2007/088447 filed on Dec. 20, 2007 and claims priority from U.S. provisional application Ser. No. 60/876,895 filed on Dec. 21, 2006, which applications are fully incorporated herein by reference.

REFERENCE TO A SEQUENCE LISTING

This application contains a Sequence Listing in computer readable form. The computer readable form is incorporated herein by reference.

BACKGROUND OF THE INVENTION

1. Field of the Invention

The present invention relates to methods of reducing or eliminating expression of a gene in a filamentous fungal strain.

2. Description of the Related Art

Filamentous fungal strains are widely used for the production of biological substances of commercial value. However, filamentous fungal strains with desirable traits of increased expression and secretion of a biological substance may not necessarily have the most desirable characteristics for successful fermentation. The production of a biological substance may be accompanied by the production of other substances, e.g., enzymes, that degrade the biological substance or co-purify with the biological substance, which can complicate recovery and purification of the biological substance.

One solution to these problems is to inactivate the gene(s) involved in the production of the undesirable substance. Inactivation can be accomplished by deleting or disrupting the gene(s) using methods well known in the art. However, in some cases, inactivation of the gene may be difficult because of poor targeting to homologous regions of the genome. Inactivation can also be accomplished by random mutagenesis, which is not always specific for the intended target gene and other mutations are often introduced into the host organism. In other situations, the gene and its product may be required for survival of the filamentous fungal strain. Where multiple genes are to be inactivated by deletion or disruption, the task can be very cumbersome and time-consuming. When highly homologous members of gene families exist, deletion or disruption of all members can be extremely tedious and difficult.

In recent years various forms of epigenetic gene regulation have been described (Selker, 1997, *Trends Genet.* 13: 296-301; Matzke and Matzke, 1998, *Cell. Mol. Life. Sci.* 54: 94-103). These processes influence gene expression by modulating the levels of messenger RNA (Hammond and Baulcombe, 1996, *Plant Mol. Biol.* 32: 79-88; Xi-song Ke et al., 2003, *Current Opinion In Chemical Biology* 7: 516-523) via micro RNAs (Morel et al., 2000, *Curr. Biol.* 10: 1591-1594; Bailis and Forsburg, 2002, *Genome Biol.* 3, Reviews 1035; Grewal and Moazed, 2003, *Science* 301: 798-802).

Based on genetic studies of *Drosophila* and *Caenorhabditis elegans*, RNA interference (RNAi), also known as post-transcriptional gene silencing (in plants), is understood to involve silencing expression of a gene by assembly of a protein-RNA effector nuclease complex that targets homologous RNAs for degradation (Hannon, 2002, *Nature* 418: 244-251). The processing of double-stranded RNA (dsRNA) into small interfering RNAs (siRNAs) is accomplished by a family of enzymes known as Dicer (Bernstein et al., 2001, *Nature* 409: 363). Dicer, a member of the RNase III family of endonucleases that specifically cleaves dsRNA, is responsible for digestion of dsRNA into siRNAs ranging from 20-25 nucleotides (Elbashir et al., 2001, *Nature* 411: 494). These siRNAs then associate with the RNA Induced Silencing Complex (RISC) (Elbashir et al., 2001, *Genes and Dev.* 15: 188; NyKanen et al., 2001, *Cell* 197: 300; Hammond et al., 2001, *Science* 293: 1146). Although not well understood, RISC targets the mRNA from which the anti-sense fragment was derived followed by endo and exonuclease digestion of the mRNA effectively silencing expression of that gene. RNAi has been demonstrated in plants, nematodes, insects, mammals, and filamentous fungi (Matzke and Matzke, 1998, supra; Kennerdell et al., 2000, *Nat. Biotechnol.* 18: 896-8; Bosher et al., 1999, *Genetics* 153: 1245-56; Voorhoeve and Agami, 2003, *Trends Biotechnol.* 21: 2-4; McCaffrey et al., 2003, *Nat. Biotechnol.* 21: 639-44; WO 03/050288; WO 01/49844; WO 98/53083; and WO 05/056772).

Transitive RNAi, also known as spreading, refers to the movement of the silencing signal beyond a particular gene. In plants, transitive silencing has been found to occur both upstream and downstream of the mRNA targeted for gene silencing by double-stranded RNA (Fabian et al., 2002, *Plant Cell* 14: 857-867; Garcia-Perez et al., 2004, *The Plant Journal* 38: 594-602; Vaistij et al., 2002, *The Plant Cell* 14: 857-867; Van Houdt et al., 2003, *Plant Physiol.* 131: 245-253). In *Caenorhabditis elegans*, transitive RNAi has been described as silencing of the transcript upstream of the target dsRNA (Alder et al., 2003, *RNA J.* 9: 25-32; Hannon, 2002, *Nature* 418: 244-251; Sijen et al., 2001, *Cell* 107: 465-476). In *C. elegans*, descriptions of transitive RNAi indicate that in addition to siRNAs derived from the dsRNA target, secondary siRNAs sharing homology with 5' flanking sequences are generated, presumably the result of RNA-dependent RNA polymerase (RdRP) and Dicer activity (Bleys et al., 2006, *RNA J.* 12: 1633-1639; Petersen et al., 2005, *Plant Molecular Biology* 58: 575-583). Transitive RNAi is not ubiquitous among insects and mammals (Chi et al., 2003, *Proc. Natl. Acad. Sci. USA* 100: 6343-6346; Hoa et al., 2003, *Insect Biochemistry and Molecular Biology* 33: 949-957; Rolgnamt et al., 2003, *RNA J.* 9: 299-308).

Transitive RNAi differs from conventional RNAi in several ways. Although double-stranded RNA serves as inducer of both RNAi and transitive RNAi, transitive RNAi appears to require an RdRP, whereas RNAi alone does not. Consequently, in organisms demonstrating transitive RNAi, gene silencing is not limited by the boundaries of double-stranded RNA, and gene silencing can extend into flanking sequences. However, in organisms lacking transitive RNAi, gene silencing is confined within the region of double strandedness.

It would be an advantage in the art to have alternative methods of reducing or eliminating expression of one or more genes for strain development and improvement, functional genomics, and pathway engineering of filamentous fungal strains.

The present invention relates to methods of reducing or eliminating expression of one or more genes in a filamentous fungal strain.

SUMMARY OF THE INVENTION

The present invention relates to methods of reducing or eliminating expression of a target gene encoding a biological substance in a filamentous fungal strain, comprising:

(a) inserting into the genome of the filamentous fungal strain a double-stranded transcribable nucleic acid construct comprising a promoter operably linked to a first polynucleotide comprising a first transcribable region with homology to the target gene encoding the biological substance and a second polynucleotide comprising a second transcribable region with no effective homology to the target gene, wherein the second transcribable region comprises two segments complementary to each other in reverse orientation and the first and second transcribable regions are transcribed as a single mRNA molecule; and (b) inducing production of short interfering RNAs (siRNAs), comprising sequences of the target gene to be silenced by the process of transitive RNAi, by cultivating the filamentous fungal strain under conditions to produce RNA transcripts of the double-stranded transcribable nucleic acid construct that are then converted to the siRNAs, which interact with RNA transcripts of the target gene to reduce or eliminate expression of the target gene encoding the biological substance.

The present invention also relates to a filamentous fungal strain comprising a double-stranded transcribable nucleic acid construct comprising a promoter operably linked to a first polynucleotide comprising a first transcribable region with homology to the target gene encoding the biological substance and a second polynucleotide comprising a second transcribable region with no effective homology to the target gene, wherein the second transcribable region comprises two segments complementary to each other in reverse orientation and the first and second transcribable regions are transcribed as a single mRNA molecule, wherein production of short interfering RNAs (siRNAs), comprising sequences of the target gene to be silenced by the process of transitive RNAi, is induced by cultivating the filamentous fungal strain under conditions to produce RNA transcripts of the double-stranded transcribable nucleic acid construct that are then converted to the siRNAs, which interact with RNA transcripts of the target gene to reduce or eliminate expression of the target gene encoding the biological substance.

The present invention further relates to methods of producing a biological substance of interest, comprising:

(a) cultivating a filamentous fungal strain under conditions conducive for production of the biological substance, wherein the filamentous fungal strain comprises a double-stranded transcribable nucleic acid construct comprising a promoter operably linked to a first polynucleotide comprising a first transcribable region with homology to a target gene encoding an undesirable biological substance and a second polynucleotide comprising a second transcribable region with no effective homology to the target gene, wherein the second transcribable region comprises two segments complementary to each other in reverse orientation and the first and second transcribable regions are transcribed as a single mRNA molecule, wherein RNA transcripts of the double-stranded transcribable nucleic acid construct are produced by the cultivating of the filamentous fungal strain that are then converted to short interfering RNAs (siRNAs), comprising sequences of the target gene to be silenced by the process of transitive RNAi, which interact with RNA transcripts of the target gene to reduce or eliminate expression of the target gene encoding the undesirable biological substance; and wherein the filamentous fungal strain comprises a third polynucleotide encoding the biological substance; and (b) recovering the biological substance from the cultivation medium.

DEFINITIONS

Figure 1:
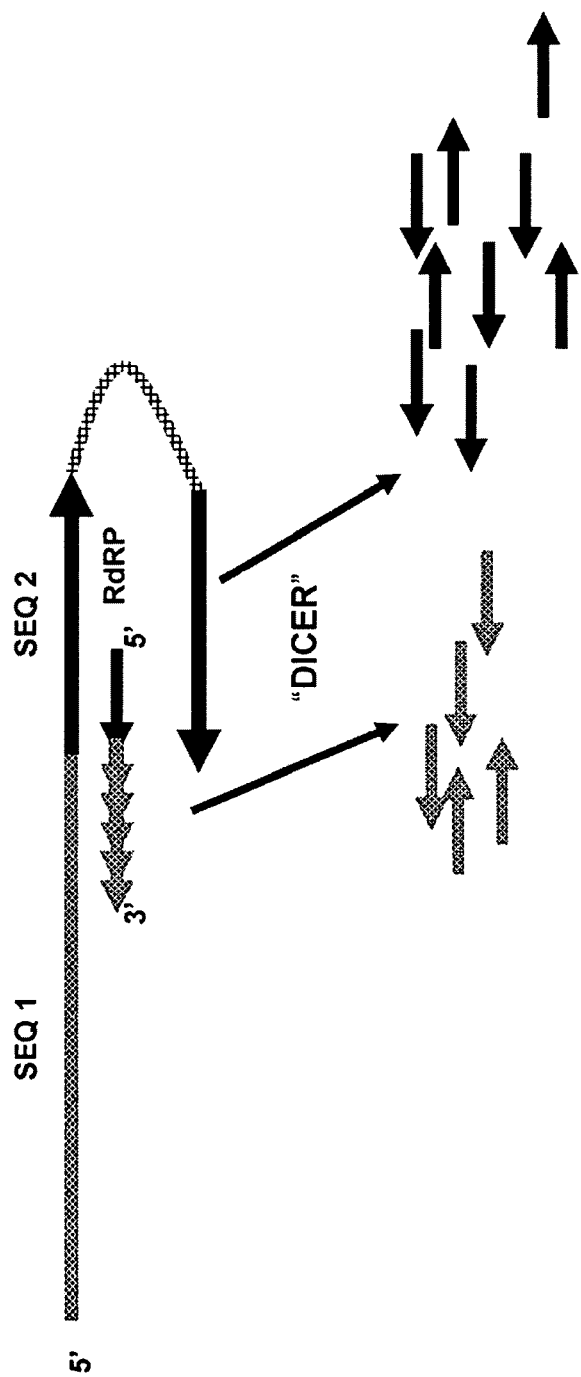
FIG. 1 shows a schematic representation of transitive RNA interference in filamentous fungi.

Transitive RNA interference: The term "transitive RNA interference" or "transitive RNAi" is defined herein as the movement of the silencing signal beyond a particular gene. In transitive RNAi, double-stranded RNA (dsRNA) can serve as template for the synthesis of new dsRNA from which siRNA sharing homology with the target sequence results in the extension or spread of silencing of new sequence along the mRNA.

Short interfering RNAs: The term "short interfering RNAs" or "siRNAs" is defined herein as 20-25 nucleotide long RNA fragments, the products of Dicer mediated digestion of double-stranded RNA.

No effective homology: The term "no effective homology" is defined herein as corresponding nucleotides on a sense strand and the reverse complement strand, which comprises preferably less than 20, more preferably less than 15, even more preferably less than 10, and most preferably less than 5 contiguous nucleotides of identical sequence to the target gene.

Two segments complementary to each other in reverse orientation: The phrase "two segments complementary to each other in reverse orientation" is defined herein as one of several stretches or pieces of DNA that fit with others to constitute a whole and capable of undergoing Watson-Crick base pairing.

Transitive silenced target sequences: The phrase "transitive silenced target sequences" is defined herein as a dsRNA sequence earmarked for gene silencing, wherein the dsRNA sequence is the result of siRNA extension from adjoining sequences.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of
Alignment−Total Number of Gaps in Alignment)

cDNA: The term "cDNA" is defined herein as a DNA molecule that can be prepared by reverse transcription from a mature, spliced, mRNA molecule obtained from a eukaryotic cell (Sambrook, J., Fritsch, E. F., and Maniatis, T, 1989, Molecular Cloning: A Laboratory Manual. $2^{nd}$ ed., Cold Spring Harbor Laboratory, Cold Spring Harbor, N.Y.). cDNA lacks intron sequences that are present in genomic DNA. The initial, primary RNA transcripts are precursor molecules that are processed through a series of steps before appearing as mature spliced mRNAs. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence.

Control sequence: The term "control sequences" is defined herein to include all components necessary for expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Promoter: The term "promoter" is defined herein as a DNA sequence that binds RNA polymerase and directs the polymerase to the correct downstream transcriptional start site of a nucleic acid sequence encoding a biological substance to initiate transcription. RNA polymerase effectively catalyzes the assembly of messenger RNA complementary to the appropriate DNA strand of a coding region. The term "promoter" will also be understood to include the 5' non-coding region (between promoter and translation start) for translation after transcription into mRNA, cis-acting transcription control elements such as enhancers, and other nucleotide sequences capable of interacting with transcription factors.

Mutant promoter: The term "mutant promoter" is defined herein as a promoter having a nucleotide sequence comprising a substitution, deletion, and/or insertion of one or more nucleotides of a parent promoter, wherein the mutant promoter has more or less promoter activity than the corresponding parent promoter. The term "mutant promoter" also encompasses natural mutants and in vitro generated mutants obtained using methods well known in the art such as classical mutagenesis, site-directed mutagenesis, and DNA shuffling.

Hybrid promoter: The term "hybrid promoter" is defined herein as parts of two or more promoters that are fused together to generate a sequence that is a fusion of the two or more promoters, which when operably linked to a coding sequence mediates the transcription of the coding sequence into mRNA.

Tandem promoter: The term "tandem promoter" is defined herein as two or more promoter sequences, arranged in tandem, operably linked to a coding sequence for mediating transcription of the coding sequence into mRNA.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a genomic DNA, cDNA, synthetic DNA, or recombinant nucleotide sequence.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide of the present invention.

DETAILED DESCRIPTION OF THE INVENTION

The present invention relates to methods of reducing or eliminating expression of a target gene encoding a biological substance in a filamentous fungal strain, comprising: (a) inserting into the genome of the filamentous fungal strain a double-stranded transcribable nucleic acid construct comprising a promoter operably linked to a first polynucleotide comprising a first transcribable region with homology to the target gene encoding the biological substance and a second polynucleotide comprising a second transcribable region with no effective homology to the target gene, wherein the second transcribable region comprises two segments complementary to each other in reverse orientation and the first and second transcribable regions are transcribed as a single mRNA molecule; and (b) inducing production of short interfering RNAs (siRNAs), comprising sequences of the target gene to be silenced by the process of transitive RNAi, by cultivating the filamentous fungal strain under conditions to produce RNA transcripts of the double-stranded transcribable nucleic acid construct that are then converted to the siRNAs, which interact with RNA transcripts of the target gene to reduce or eliminate expression of the target gene encoding the biological substance.

FIG. 1 demonstrates transitive RNA interference. Transformants produce transcription products composed of a target segment flanked 3' by an inverted repeat (IR) having no homology with the target gene. Double-stranded RNA (dsRNA) produced by folding and annealing of the IR are processed by Dicer producing siRNA sharing homology with the IR. Using the transcript as template, a portion of siRNAs are extended by an RNA-dependent RNA polymerase (RdRP) further than the 5' IR boundary infiltrating the target sequence. Continued extension produces dsRNA encoded by the target, initiating RNAi.

The methods of the present invention provide new opportunities for strain development and improvement, functional genomics, and pathway engineering in filamentous fungal strains. For example, the present methods can be used as a tool for filamentous fungal host strain development by means of gene manipulation and pathway engineering or as replacement for gene knockouts, a time-consuming approach with variable rates of success. A gene may be resistant to inactivation by standard methods known in the art such as gene knockout. The methods of the present invention provide a solution for reducing or eliminating expression of such a gene. Gene knockouts are dependent on site-specific gene replacement. In fungi efficacy of this process is affected by chromosome locus, DNA sequences shared by the replacement construct and genome, and/or length of the shared homology. Attainment of transitive gene silencing as described is uniquely dependent on cloning of a portion of the target sequence upstream of a second sequence comprised of an inverted repeat. The methods are also particularly useful and efficient for reducing or eliminating a highly expressed gene in a particular filamentous fungal strain, which can be very important, for example, in developing the organism as a production host. This ability demonstrates the strength of the methods of the present invention. The methods are also useful for reducing or eliminating expression of a multiple of genes that are highly homologous to each other, especially genes of the same family or homologous genes in a biosynthetic or metabolic pathway. The methods are further useful because they can be manipulated to cause a variable reduction in expression of a biological substance. This variability is especially important where a complete knock-out of a gene encoding a biological substance would be lethal to a particular filamentous fungal strain, such as in a secondary pathway that feeds into a biosynthetic pathway of interest.

In the methods of the present invention, the first polynucleotide comprises a first transcribable region with homology to the target gene. The second polynucleotide comprises a second transcribable region with no effective homology to the target gene, wherein the second transcribable region comprises two segments complementary to each other in reverse orientation.

The first polynucleotide comprising a first transcribable region with homology to the target gene encoding the biological substance and a second polynucleotide comprising a second transcribable region with no effective homology to the target gene may or may not be separated by a polynucleotide intervening sequence, which is a nucleotide sequence that has little or no homology to the first and second polynucleotides in the double-stranded transcribable nucleic acid construct. The polynucleotide sequences of the double-stranded transcribable nucleic acid construct may be of genomic, cDNA, RNA, semisynthetic, synthetic origin, or any combinations thereof.

In a preferred aspect, the first and second polynucleotides are separated by a polynucleotide intervening sequence. The intervening sequence preferably consists of less than 150 nucleotides, more preferably less than 100 nucleotides, more preferably less than 60 nucleotides, more preferably less than 40 nucleotides, even more preferably less than 20 nucleotides, and most preferably less than 10 nucleotides.

In a more preferred aspect, the first and second polynucleotides are not separated by a polynucleotide intervening sequence.

The intervening sequence can be any nucleotide sequence without homology to the first or second polynucleotide and preferably has little or no homology to sequences in the genome of the filamentous fungal strain to minimize undesirable targeting/recombination.

Promoter

The promoter sequence may be native or foreign (heterologous) to the first homologous transcribable region and native or foreign to the filamentous fungal strain. In the methods of the present invention, the promoter can be a native promoter, heterologous promoter, mutant promoter, hybrid promoter, or tandem promoter.

Examples of promoters useful in the methods of the present invention include the promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Dana (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In preferred aspect, the promoter is the NA2-tpi promoter. In another preferred aspect, the promoter is the TAKA/NA2-tpi leader hybrid promoter.

Homologous Transcribable Region

The term "transcribable region with homology to a target gene" is defined herein as a nucleotide sequence that is homologous to the open reading frame of a target gene, or a portion thereof, and is transcribed into an RNA, e.g., ncRNA (non-coding RNA), tRNA (transfer RNA), rRNA (ribosomal RNA), miRNA (micro RNA), or mRNA (messenger RNA), which may or may not be translated into a biological substance, e.g., polypeptide, when placed under the control of the appropriate regulatory sequences. The boundaries of the transcribable region are generally determined by the transcription start site located just upstream of the open reading frame at the 5' end of the mRNA and a transcription terminator sequence located just downstream of the open reading frame at the 3' end of the mRNA. A homologous transcribable region can include, but is not limited to, genomic DNA, cDNA, semisynthetic, synthetic, and recombinant nucleic acid sequences.

In the methods of the present invention, the transcribable region homologous to the target gene may be identical to the corresponding region of the target gene or may be a homologue thereof.

The degree of identity between the homologue and the corresponding region of the target gene required to achieve inactivation or reduction of expression of the target gene will likely depend on the target gene. The smaller the homologue's nucleotide sequence is relative to the entire target gene, the degree of identity between the sequences should preferably be very high or identical. The larger the homologue's nucleotide sequence is relative to the entire target gene, the degree of identity between the sequences can likely be lower.

In the methods of the present invention, the degree of identity of the homologue's nucleotide sequence to the corresponding region of the target gene is at least 65%, preferably at least 70%, more preferably at least 75%, more preferably at least 80%, more preferably at least 85%, more preferably at least 90%, even more preferably at least 95%, and most preferably at least 97%. For purposes of the present invention, the degree of identity between two nucleic acid sequences is determined as defined herein.

Alternatively, the ability of the homologue and the corresponding region of the target gene to hybridize to each other under various stringency conditions can also provide an indication of the degree of relatedness required for inactivation or reduction of expression of a target gene. However, it should be recognized that the lower the stringency conditions required, e.g., low stringency, to achieve hybridization between the homologue and the corresponding region of the target gene, inactivation or reduction of expression of the target gene will likely be less efficient.

In a preferred aspect, the homologue and the corresponding region of the target gene hybridize under low stringency conditions. In a more preferred aspect, the homologue and the corresponding region of the target gene hybridize under medium stringency conditions. In an even more preferred aspect, the homologue and the corresponding region of the target gene hybridize under medium-high stringency conditions. In a most preferred aspect, the homologue and the corresponding region of the target gene hybridize under high stringency conditions. In an even most preferred aspect, the homologue and the corresponding region of the target gene hybridize under very high stringency conditions.

For probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For probes of about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For probes of about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

The first homologous region preferably consists of at least 19 nucleotides, more preferably at least 40 nucleotides, more preferably at least 60 nucleotides, more preferably at least 80 nucleotides, even more preferably at least 100 nucleotides, and most preferably at least 200 nucleotides. The first homologous region can also consist of the entire open reading frame of the gene or a homologue thereof.

Non-Homologous Transcribable Region

The double-stranded transcribable nucleic acid construct also comprises a second transcribable region with no effective homology to the target gene or the host genome, wherein the second transcribable region comprises two segments complementary to each other in reverse orientation.

In a preferred aspect, the second transcribable region is any transcribable part of any gene, such as the 5'-untranslated region, the coding sequence, or the 3'-untranslated region of a gene, which has no effective homology to the target gene or the host genome.

In a more preferred aspect, the second transcribable region corresponds to the coding sequence of a gene with no effective homology to the target gene or the host genome.

In another more preferred aspect, the second transcribable region corresponds to the 5'-untranslated region of a gene with no effective homology to the target gene or the host genome.

In another more preferred aspect, the second transcribable region corresponds to the 3'-untranslated region of a gene with no effective homology to the target gene or the host genome.

In a most preferred aspect, the second transcribable region is a portion of a non-endogenous gene, which has no homology to the target gene or the host genome, e.g., the hygromycin resistance gene of *E. coli*.

The second transcribable region preferably consists of at least 19 nucleotides, more preferably at least 40 nucleotides, more preferably at least 60 nucleotides, more preferably at least 80 nucleotides, more preferably at least 100 nucleotides, more preferably at least 250 nucleotides, even more preferably at least 500 nucleotides, most preferably at least 750 nucleotides, and even most preferably at least 1000 nucleotides.

The two segments complementary to each other in reverse orientation can be separated by a polynucleotide linker. The linker preferably consists of at least 4 nucleotides, more preferably of at least 20 nucleotides, more preferably at least 40 nucleotides, more preferably at least 60 nucleotides, more preferably at least 80 nucleotides, even more preferably at least 100 nucleotides, most preferably at least 250 nucleotides, and even most preferably at least 500 nucleotides.

Target Gene

The target gene may be any gene encoding a substance having a biological activity or any gene encoding a polypeptide having biological activity involved in the biosynthesis of a metabolite (hereinafter "biological substance"). The biological substance may be an RNA (e.g., ncRNA, rRNA, tRNA, miRNA, or mRNA). The biological substance may also be a polypeptide having a biological activity. The biological substance may also be a metabolite. The substance having biological activity may be native to the filamentous fungal strain or foreign or heterologous to the strain. A foreign or heterologous substance is a substance that is not native to the cell; or a native substance to which structural modifications have been made to alter the native substance.

In a preferred aspect, the biological substance is a polypeptide having biological activity. The polypeptide may be any polypeptide having a biological activity. The term "polypeptide" is not meant herein to refer to a specific length of the encoded product and, therefore, encompasses peptides, oligopeptides, polypeptides and proteins. The term "polypeptide" also encompasses two or more polypeptides combined to form the encoded product. Polypeptides also include hybrid polypeptides, which comprise a combination of partial or complete polypeptide sequences obtained from at least two different polypeptides wherein one or more may be heterologous to the filamentous fungal cell. Polypeptides further include naturally occurring allelic and engineered variations of the above-mentioned polypeptides and hybrid polypeptides.

In a preferred aspect, the polypeptide is an antibody, antigen, antimicrobial peptide, enzyme, growth factor, hormone, immunodilator, neurotransmitter, receptor, reporter protein, structural protein, and transcription factor.

In a more preferred aspect, the polypeptide is an oxidoreductase, transferase, hydrolase, lyase, isomerase, or ligase. In a most preferred aspect, the polypeptide is an acetylxylan esterase, aminopeptidase, amylase, carbohydrase, carboxypeptidase, catalase, cellulase, chitinase, cutinase, cyclodextrin glycosyltransferase, deoxyribonuclease, esterase, ferulic acid esterase, alpha-galactosidase, beta-galactosidase, glucoamylase, glucocerebrosidase, alpha-glucosidase, beta-glucosidase, invertase, laccase, lipase, mannosidase, mutanase, oxidase, pectinolytic enzyme, peroxidase, phospholipase, phytase, polyphenoloxidase, proteolytic enzyme, ribonuclease, transglutaminase, urokinase, or xylanase In another preferred aspect, the polypeptide is an albumin, collagen, tropoelastin, elastin, or gelatin; or a variant or hybrid thereof.

The biological substance may also be the product of a selectable marker. A selectable marker is a gene the product of which provides for biocide or viral resistance, resistance to heavy metals, prototrophy to auxotrophs, and the like. Selectable markers include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof.

It may be necessary in the practice of the present invention to isolate the target gene. The techniques used to isolate or clone a gene are known in the art and include isolation from genomic DNA, preparation from cDNA, or a combination thereof. The cloning of the gene from such genomic DNA can be effected, e.g., by using the well known polymerase chain reaction (PCR). See, for example, Innis et al., 1990, PCR Protocols: A Guide to Methods and Application, Academic Press, New York. The cloning procedures may involve excision and isolation of a desired nucleic acid fragment comprising the gene encoding a biological substance, insertion of the fragment into a vector molecule, and incorporation of the recombinant vector into a filamentous fungal cell where multiple copies or clones of the nucleic acid sequence will be replicated. The nucleic acid sequence may be of genomic, cDNA, RNA, semisynthetic, synthetic origin, or any combinations thereof.

In a preferred aspect, expression of the target gene is reduced by at least 20%, preferably at least 30%, more preferably at least 40%, more preferably at least 50%, more preferably at least 60%, more preferably at least 70%, even more preferably at least 80%, most preferably at least 90%, and even most preferably 100%.

Where it is desired to use a target sequence within the 5' untranslated region, the coding sequence, or the 3' untranslated region, gene silencing vectors constructed with inverted repeats within any one of these regions may additionally enable the silencing of genes that are homologous to the coding sequence present in the silencing vector. When it is, therefore, desired to silence homologues of a gene within an organism, the construction of a silencing vector containing a transitive expressed target sequence having homology within the 5' untranslated region, the coding sequence, or the 3' untranslated region may allow the elimination or reduction of expression of one or more genes exhibiting sequence homology to the coding sequence within the construct. The term "homology" or "homologous" usually denotes those sequences that are of some common ancestral structure and exhibit a high degree of sequence similarity of the active regions.

In a preferred aspect, the interfering RNA interacts with RNA transcripts of one or more homologues of the target gene to reduce or eliminate expression of the one or more homologues of the target gene.

In a more preferred aspect, expression of one or more homologues of the target gene is reduced by at least 20%, preferably at least 30%, more preferably at least 40%, more preferably at least 50%, more preferably at least 60%, more preferably at least 70%, even more preferably at least 80%, most preferably at least 90%, and even most preferably 100%

Filamentous Fungal Strains

The present invention also relates to filamentous fungal strains comprising a double-stranded transcribable nucleic acid construct comprising a promoter operably linked to a first polynucleotide comprising a first transcribable region with homology to the target gene encoding the biological substance and a second polynucleotide comprising a second transcribable region with no effective homology to the target gene, wherein the second transcribable region comprises two segments complementary to each other in reverse orientation and the first and second transcribable regions are transcribed as a single mRNA molecule, wherein production of short interfering RNAs (siRNAs), comprising sequences of the target gene to be silenced by the process of transitive RNAi, is induced by cultivating the filamentous fungal strain under conditions to produce RNA transcripts of the double-stranded transcribable nucleic acid construct that are then converted to the siRNAs, which interact with RNA transcripts of the target gene to reduce or eliminate expression of the target gene encoding the biological substance.

The filamentous fungal strain may be any filamentous fungal strain useful in the methods of the present invention. "Filamentous fungi" include all filamentous forms of the subdivision Eumycota and Oomycota (as defined by Hawksworth et al., In, Ainsworth and Bisby's Dictionary of The Fungi, 8th edition, 1995, CAB International, University Press, Cambridge, UK). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as Saccharomyces cerevisiae is by budding of a unicellular thallus and carbon catabolism may be fermentative.

In a preferred aspect, the filamentous fungal strain is an Acremonium, Aspergillus, Aureobasidium, Bierkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes, or Trichoderma strain.

In a more preferred aspect, the filamentous fungal strain is an Aspergillus awamori, Aspergillus fumigatus, Aspergillus foetidus, Aspergillus japonicus, Aspergillus nidulans, Aspergillus niger or Aspergillus oryzae strain. In another most preferred aspect, the filamentous fungal strain is a Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, or Fusarium venenatum strain. In another most preferred aspect, the filamentous fungal strain is a Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei, or Trichoderma viride strain.

In a most preferred aspect, the Aspergillus oryzae strain is Aspergillus oryzae strain deposit no. IFO 4177. In another most preferred aspect, the Fusarium venenatum strain is Fusarium venenatum A3/5, which was originally deposited as Fusarium graminearum ATCC 20334 and recently reclassified as Fusarium venenatum by Yoder and Christianson, 1998, Fungal Genetics and Biology 23: 62-80 and O'Donnell et al., 1998, Fungal Genetics and Biology 23: 57-67; as well as taxonomic equivalents of Fusarium venenatum regardless of the species name by which they are currently known. In another most preferred aspect, the Fusarium venenatum strain is a morphological mutant of Fusarium venenatum A3/5 or Fusarium venenatum ATCC 20334, as disclosed in WO 97/26330. In another most preferred aspect, the Trichoderma reesei strain is Trichoderma reesei ATCC 56765. In another most preferred aspect, the Aspergillus niger strain is Aspergillus niger Bo-1 (DSM 12665). In another most preferred aspect, the Aspergillus niger strain is a mutant of Aspergillus niger Bo-1 (DSM 12665), as disclosed in WO 2004/090155.

Filamentous fungal strains may be transformed by a process involving protoplast formation, transformation of the protoplasts, and regeneration of the cell wall in a manner known per se. Suitable procedures for transformation of Aspergillus and Trichoderma strains are described in EP 238 023 and Yelton et al., 1984, Proceedings of the National Academy of Sciences USA 81: 1470-1474. Suitable methods for transforming Fusarium species are described by Malardier et al., 1989, Gene 78: 147-156 and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, Journal of Bacteriology 153: 163; and Hinnen et al., 1978, Proceedings of the National Academy of Sciences USA 75:1920.

Reduction or elimination of expression of a target gene encoding an undesirable biological substance may be detected using methods known in the art that are specific for the targeted biological substance. These detection methods may include use of specific antibodies, high performance liquid chromatography, capillary electrophoresis, formation of an enzyme product, disappearance of an enzyme substrate, SDS-PAGE, or loss or appearance of a phenotype, e.g., spore color. For example, an enzyme assay may be used to determine the activity of the enzyme. Procedures for determining enzyme activity are known in the art for many enzymes (see, for example, D. Schomburg and M. Salzmann (eds.), Enzyme Handbook, Springer-Verlag, New York, 1990).

Methods of Production

The present invention also relates to methods of producing a biological substance of interest, comprising: (a) cultivating a filamentous fungal strain under conditions conducive for production of the biological substance of interest, wherein the filamentous fungal strain comprises a double-stranded transcribable nucleic acid construct comprising a promoter operably linked to a first polynucleotide comprising a first transcribable region with homology to a target gene encoding an undesirable biological substance and a second polynucleotide comprising a second transcribable region with no effective homology to the target gene, wherein the second transcribable region comprises two segments complementary to each other in reverse orientation and the first and second transcribable regions are transcribed as a single mRNA molecule, wherein RNA transcripts of the double-stranded transcribable nucleic acid construct are produced by cultivating the filamentous fungal strain under conditions to produce the RNA transcripts that are then converted to short interfering RNAs (siRNAs), comprising sequences of the target gene to be silenced by the process of transitive RNAi, which interact with RNA transcripts of the target gene to reduce or eliminate expression of the target gene encoding the undesirable biological substance; and wherein the filamentous fungal strain comprises a third polynucleotide encoding the biological substance of interest; and (b) recovering the biological substance of interest from the cultivation medium.

The biological substance of interest may be any biological substance as described herein. In a preferred aspect, the biological substance of interest is a polypeptide having biological activity. It may be native or foreign to the filamentous fungal strain. The reduction or elimination of expression of the target gene encoding the undesirable biological substance can lead to increased expression of another biological substance of interest. The undesirable biological substance could directly affect production or expression of the biological substance of interest. For example, the undesirable biological substance may be a protease that attacks the biological substance of interest thereby lowering the amount of the biological substance of interest produced. By reducing or eliminating expression of the protease, more of the biological substance of interest will be expressed and produced. Or, the undesirable biological substance may share a cellular process or processes, e.g., transcription factor or secretory pathway, with the biological substance of interest thereby lowering the amount of the biological substance of interest produced. By reducing or eliminating expression of the undesirable biological substance, more of the cellular process or processes will be available to the biological substance of interest, e.g., expression-limiting transcription elements, thereby increasing the amount of the biological substance of interest expressed and produced. Moreover, the undesirable biological substance may be a toxin that contaminates the biological substance of interest preventing the use of the biological substance of interest in a particular application, e.g., an enzyme in a food process.

In the production methods of the present invention, the filamentous fungal strains are cultivated in a nutrient medium suitable for production of the biological substance of interest using methods known in the art. For example, the strain may be cultivated by shake flask cultivation, and small-scale or large-scale fermentation (including continuous, batch, fed-batch, or solid state fermentations) in laboratory or industrial fermentors performed in a suitable medium and under conditions allowing the biological substance to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the biological substance is secreted into the nutrient medium, it can be recovered directly from the medium. If the biological substance is not secreted, it can be recovered from cell lysates.

The biological substance of interest may be detected using methods known in the art that are specific for the biological substances. These detection methods may include use of specific antibodies, high performance liquid chromatography, capillary chromatography, formation of an enzyme product, disappearance of an enzyme substrate, or SDS-PAGE. For example, an enzyme assay may be used to determine the activity of the enzyme. Procedures for determining enzyme activity are known in the art for many enzymes (see, for example, D. Schomburg and M. Salzmann (eds.), *Enzyme Handbook*, Springer-Verlag, New York, 1990).

The resulting biological substance of interest may be isolated using methods known in the art. For example, a polypeptide of interest may be isolated from the cultivation medium by conventional procedures including, but not limited to, centrifugation, filtration, extraction, spray-drying, evaporation, or precipitation. The isolated polypeptide may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., *Protein Purification*, J.-C. Janson and Lars Ryden, editors, VCH Publishers, New York, 1989). A metabolite of interest may be isolated from a cultivation medium by, for example, extraction, precipitation, or differential solubility, or any method known in the art. The isolated metabolite may then be further purified using methods suitable for metabolites.

Polynucleotides Encoding a Biological Substance

An isolated polynucleotide sequence encoding a biological substance of interest may be obtained from any prokaryotic, eukaryotic, or other source. For purposes of the present invention, the term "obtained from" as used herein in connection with a given source shall mean that the biological substance is produced by the source or by a cell in which a gene from the source has been inserted.

The techniques used to isolate or clone a polynucleotide encoding a biological substance of interest are known in the art and include isolation from genomic DNA, preparation from cDNA, or a combination thereof. The cloning of the polynucleotide from such genomic DNA can be effected, e.g., by using the well known polymerase chain reaction (PCR). See, for example, Innis et al., 1990, *PCR Protocols: A Guide to Methods and Application*, Academic Press, New York. The cloning procedures may involve excision and isolation of a desired nucleic acid fragment comprising the polynucleotide encoding the biological substance, insertion of the fragment into a vector molecule, and incorporation of the recombinant vector into the mutant filamentous fungal cell where multiple copies or clones of the nucleic acid sequence will be replicated. The polynucleotide may be of genomic, cDNA, RNA, semisynthetic, synthetic origin, or any combinations thereof.

Nucleic Acid Constructs

An isolated polynucleotide encoding a biological substance of interest may be contained in a nucleic acid construct in the filamentous fungal strain. A nucleic acid construct comprises a nucleotide sequence encoding the biological substance of interest operably linked to at least one promoter and one or more control sequences that direct expression of the nucleotide sequence in a filamentous fungal strain under conditions compatible with the control sequences. Expression will be understood to include any step involved in the production of the biological substance of interest including, but not limited to, transcription, post-transcriptional modification, translation, post-translational modification, and secretion.

The isolated polynucleotide encoding the biological substance of interest may be further manipulated in a variety of ways to provide for expression of the biological substance. Manipulation of the nucleotide sequence prior to its insertion into a vector may be desirable or necessary depending on the expression vector. The techniques for modifying nucleotide sequences utilizing recombinant DNA methods are well known in the art.

The polynucleotide may comprise one or more native control sequences or one or more of the native control sequences may be replaced with one or more control sequences foreign to the nucleotide sequence for improving expression of the coding sequence in a host cell. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a biological substance of interest.

The control sequence may be an appropriate promoter sequence, a nucleotide sequence that is recognized by a host cell for expression of a polynucleotide encoding biological substance. The promoter sequence contains transcriptional control sequences that mediate expression of the biological substance. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

The control sequence may be a suitable transcription terminator sequence, a sequence recognized by a host cell to terminate transcription. The terminator sequence is operably linked to the 3' terminus of the nucleic acid sequence encoding the biological substance. Any terminator that is functional in the filamentous fungal strain of choice may be used in the present invention.

Preferred terminators for filamentous fungal strain are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

The control sequence may also be a suitable leader sequence, a nontranslated region of an mRNA that is important for translation by the filamentous fungal strain. The leader sequence is operably linked to the 5' terminus of the nucleic acid sequence encoding the biological substance. Any leader sequence that is functional in the filamentous fungal strain of choice may be used in the present invention.

Preferred leaders for filamentous fungal strains are obtained from the genes for *Aspergillus oryzae* TAKA amylase, *Aspergillus nidulans* triose phosphate isomerase, *Fusarium venenatum* trypsin, and *Fusarium venenatum* glucoamylase.

The control sequence may also be a polyadenylation sequence, a sequence operably linked to the 3' terminus of the nucleic acid sequence that, when transcribed, is recognized by the host cell as a signal to add polyadenosine residues to transcribed mRNA. Any polyadenylation sequence that is functional in the filamentous fungal strain of choice may be used in the present invention.

Preferred polyadenylation sequences for filamentous fungal strains are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region that directs the expressed polypeptide into the secretory pathway of a fungal host cell of choice may be used in the present invention.

Effective signal peptide coding regions for filamentous fungal strains are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences that allow the regulation of expression of the biological substance relative to the growth of the filamentous fungal strain. Examples of regulatory systems are those that cause expression of the gene to be turned on or off in response to a chemical or physical stimulus, including the presence of a regulatory compound. In filamentous fungi, the TAKA alpha-amylase promoter, *Aspergillus niger* glucoamylase promoter, *Aspergillus oryzae* glucoamylase promoter, and *Fusarium venenatum* glucoamylase promoter may be used as regulatory sequences. Other examples of regulatory sequences are those that allow for gene amplification. In eukaryotic systems, these include the dihydrofolate reductase gene that is amplified in the presence of methotrexate, and the metallothionein genes that are amplified with heavy metals. In these cases, the nucleotide sequence encoding the biological substance of interest would be operably linked with the regulatory sequence.

Expression Vectors

A polynucleotide encoding a biological substance of interest may be contained in a recombinant expression vector comprising a promoter, the nucleotide sequence encoding the biological substance, and transcriptional and translational stop signals. The various nucleic acids and control sequences described herein may be joined together to produce a recombinant expression vector that may include one or more (several) convenient restriction sites to allow for insertion or substitution of the nucleotide sequence encoding the polypeptide at such sites. Alternatively, a polynucleotide sequence may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors preferably contain one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of origins of replication useful in a filamentous fungal cell are AMA1 and ANS1 (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide may be inserted into a host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors are well known to one skilled in the art (see, e.g., Sambrook et al., 1989, supra).

The present invention is further described by the following examples that should not be construed as limiting the scope of the invention.

EXAMPLES

Media and Solutions amdS Overlay agar was composed per liter of 20 ml of COVE salt solution, 273.8 g of sucrose, 8 g of Noble agar, 10 mM acetamide, and 15 mM CsCl, pH 5.0.

AMG trace metals solution was composed per liter of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4.H_2O$, and 3.0 g of citric acid.

Cellulase-inducing medium was composed per liter of 20 g of Arbocel-natural cellulose fibers (J. Rettenmaier USA LP), 10 g of corn steep solids (Sigma Chemical Co., St. Louis, Mo., USA), 1.45 g of $(NH_4)_2SO_4$, 2.08 g of $KH_2PO_4$, 0.28 g of $CaCl_2$, 0.42 g of $MgSO_4.7H_2O$, 0.42 ml of

*Trichoderma reesei* trace metals solution, and 2 drops of pluronic acid. The pH was adjusted to 6.0 with 10 N NaOH before autoclaving.

COVE selection plates were composed per liter of 342.3 g of sucrose, 20 ml of COVE salt solution, 10 mM acetamide, 15 mM CsCl$_2$, and 25 g or 30 g of Noble agar.

COVE2 plates were composed per liter of 30 g of sucrose, 20 ml of COVE salt solution, 10 mM acetamide, and 25 g or 30 g of Noble agar.

COVE salt solution was composed per liter of 26 g of KCl, 26 g of MgSO$_4$.7H$_2$O, 76 g of KH$_2$PO$_4$, and 50 ml of COVE trace metals solution.

COVE trace metals solution was composed per liter of 0.04 g of NaB$_4$O$_7$.10H$_2$O, 0.4 g of CuSO$_4$.5H$_2$O, 1.2 g of FeSO$_4$.7H$_2$O, 0.7 g or 1 g of MnSO$_4$.H$_2$O, 0.8 g of Na$_2$MoO$_2$.2H$_2$O, and 10 g of ZnSO$_4$.7H$_2$O.

COVE A salt solution was composed per liter of 26 g of KCl, 26 g of MgSO$_4$, 76 g of KH$_2$PO$_4$, and 50 ml of COVE A trace elements solution.

COVE A trace elements solution was composed per liter of 0.04 g of NaB$_4$O$_7$.10H$_2$O, 0.4 g of CuSO$_4$.5H$_2$O, 0.8 g of FeSO$_4$.7H$_2$O, 0.8 g of MnSO$_4$.H$_2$O, 0.8 g of Na$_2$MoO$_2$.2H$_2$O, 10 g of ZnSO$_4$.7H$_2$O, and 10 g of citric acid.

COVE A minus urea plus acetamide selective plates were composed per liter of 20 ml of COVE A salt solution, 220 g of sorbitol, 10 g of glucose, 10 mM acetamide, and 30 g of Bacto agar, pH 5.2.

M410 was composed per liter of 50 g of maltose, 50 g of glucose, 2 g of MgSO$_4$.7H$_2$O, 2 g of KH$_2$PO$_4$, 4 g of citric acid, 8 g of yeast extract, 2 g of urea, 0.5 ml of AMG trace metals solution, and 0.5 g of CaCl$_2$, pH 6.0.

Minimal medium was composed per liter of 6 g of NaNO$_3$, 0.52 g of KCl, 1.52 g of KH$_2$PO$_4$, 1 ml of COVE trace elements solution, 10 g of glucose, 0.5 g of MgSO$_4$.7H$_2$O, and 0.004 g of D-biotin.

Minimal medium agar was composed per liter of 6 g of NaNO$_3$, 0.52 g of KCl, 1.52 g of KH$_2$PO$_4$, 1 ml of COVE trace elements solution, 20 g of Agar Noble, 10 g of glucose, 0.5 g of MgSO$_4$.7H$_2$O, and 0.004 g of D-biotin.

PDA plates were composed per liter of 39 g of DIFCO™ Potato Dextrose Sugar (Becton Dickinson and Co., Sparks, Md., USA).

PEG was composed of 60% PEG 4000 (Polysciences, Inc., Warrington, Pa., USA), 10 mM CaCl$_2$, and 10 mM Tris-HCl, pH 6.5, filter sterilized.

SPC was composed of 40% PEG 4000, 50 mM CaCl$_2$, and 0.8 M sorbitol, pH 4.5-5.5, filter sterilized.

20×SSC was composed per liter of 175.3 g of NaCl and 88.2 g of sodium citrate pH 7.0.

0.5×SSC was composed per liter of 4.38 g of NaCl and 2.2 g of sodium citrate pH 7.0.

STC was composed of 1 M sorbitol, 10 mM CaCl$_2$, and 10 mM Tris-HCl, pH 6.5, filter sterilized.

*Trichoderma reesei* trace metals solution was composed per liter of 216 g of FeCl$_3$.6H$_2$O, 58 g of ZnSO$_4$.7H$_2$O, 27 g of MnSO$_4$.H$_2$O, 10 g of CuSO$_4$.5H$_2$O, 2.4 g of H$_3$BO$_3$, and 336 g of citric acid.

YPG was composed per liter of 10 g of yeast extract (Fisher Scientific, Fair Lawn, N.J., USA), 20 g of BACTO™ peptone (Becton Dickinson and Co., Sparks, Md., USA), and 20 g of glucose.

Example 1

Construction of Plasmid pCW098

Plasmid pCW098 was constructed to contain the TAKA/NA2-tpi leader hybrid promoter (U.S. Pat. No. 6,461,837), an inverted repeat (hyg IR) made from a portion of the *Escherichia coli* hygromycin resistance gene (Kaster et al, 1983, *Nucleic Acids Res.* 11: 6895-6911), the *Aspergillus niger* amyloglucosidase (AMG) terminator (Hata et al., 1991, *Agric. Biol. Chem.* 55: 941-949, and the *Aspergillus nidulans* pyrG gene as a selectable marker (Ballance and Turner, 1985, *Gene* 36: 321-331).

To express a double-stranded RNA (dsRNA) derived from the *Escherichia coli* aph(4) (hygB) gene (Kaster et al., 1983, supra), one half of the inverted repeat, 199 base pairs from within the open reading frame of the aph(4) gene, was PCR amplified using a sense strand primer possessing a Not I restriction site and an antisense primer possessing a 5' Sma I or Xma I restriction site, as shown below.

```
Primer cwhygnot.1 (sense):
                                       (SEQ ID NO: 1)
5'-gcggccgcGCGATGTTCGGGGATTCCCAATACGAGGTC-3'

Primer cwhygsma.1a (antisense):
                                       (SEQ ID NO: 2)
5'-cccgggGCATCATCGAAATTGCCGTCAACCAAGCTC-3'
```

Portions of the hygB coding sequence are shown in uppercase letters.

The amplification reaction (50 µl) was composed of 1× THERMOPOL™ Reaction Buffer (New England Biolabs, Beverly, Mass., USA), 0.4 mM dNTPs, 100 ng of pSMai155 (WO 05/074647), 50 pmoles of sense primer, 50 pmoles of antisense primer, and 5 units of Taq DNA polymerase (New England Biolabs, Beverly, Mass., USA). The reactions were incubated in an EPPENDORF® MASTERCYCLER® 5333 (Eppendorf AG, Hamburg, Germany) programmed for 30 cycles each for 30 seconds at 94° C., 30 seconds at 55° C., and 1 minute at 72° C. (7 minute final extension).

A PCR product of 214 bp was purified by 1% agarose gel electrophoresis in TAE buffer (4.84 g of Tris Base, 1.14 ml of glacial acetic acid, and 2 ml of 0.5 M EDTA pH 8.0 per liter) and further purified using a QIAQUICK® Gel Extraction Kit (QIAGEN Inc., Valencia, Calif., USA). The 214 bp PCR product was ligated with pCR2.1-TOPO® using a TOPO® TA Cloning Kit and transformed into ONE SHOT® TOP10 chemically competent *E. coli* cells according to the manufacturer's instructions (Invitrogen Corporation, Carlsbad, Calif., USA). Plasmid DNA from several transformants was purified using a BIOROBOT® 9600 (QIAGEN Inc., Valencia, Calif., USA) and analyzed by DNA sequencing to identify those containing the desired hygB insert. One plasmid with the expected DNA sequence was designated MP#3.

The other half of the inverted repeat including a 100 base pair spacer was amplified using a sense strand primer possessing a 5' Pac I restriction site and an antisense primer possessing a 5' Sma I or Xma I restriction site shown below; hygB sequence is shown in uppercase letters.

```
Primer cwhygpac.2 (sense):
                                       (SEQ ID NO: 3)
5'-ttaattaaGCGATGTTCGGGGATTCCCAATACGAGGTC-3'

Primer cwhygsma.2a (antisense):
                                       (SEQ ID NO: 4)
5'-cccgggATCGGTCCAGACGGCCGCGCTTCTGCGGGC-3'
```

The amplification reaction (50 µl) was composed of 1× THERMOPOL™ Reaction Buffer, 0.4 mM dNTPs, 100 ng of pSMai155, 50 pmoles of sense primer, 50 pmoles of antisense primer, and 5 units of Taq DNA polymerase. The reactions were incubated in an EPPENDORF® MASTER-CYCLER® 5333 programmed for 30 cycles each for 30 seconds at 94° C., 30 seconds at 55° C., and 1 minute at 72° C. (7 minute final extension).

A PCR product of 314 bp was purified by 1% agarose gel electrophoresis in TAE buffer and further purified using a QIAQUICK® Gel Extraction Kit. The 314 bp PCR product was ligated with pCR2.1-TOPO® using a TOPO® TA Cloning Kit and transformed into ONE SHOT® TOP10 chemically competent *E. coli* cells according to the manufacturer's instructions. Plasmid DNA from several transformants was purified using a BIOROBOT® 9600 and analyzed by DNA sequencing to identify those containing the desired hygB insert. One plasmid with the expected DNA sequence was designated MP#9.

Figure 2:
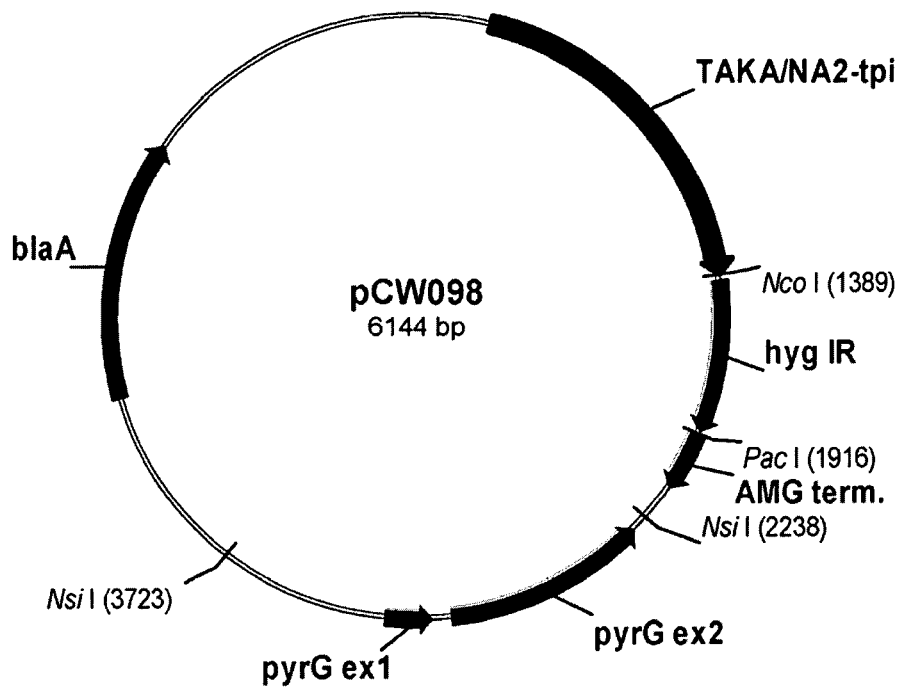
FIG. 2 shows a restriction map of pCW098.

MP#3 was digested with Not I and Xma I. MP#9 was digested with Pac I and Xma I. Both hygB DNA fragments were purified by 1% agarose gel electrophoresis in TAE buffer and extracted using a QIAQUICK® Gel Extraction Kit. The fragments were ligated to Not I/Pac I digested vector pAILo2 (WO 05/056772, Example 21) to create pCW098 (FIG. 2).

Example 2

Construction of Plasmid pCW099

Plasmid pCW099 was constructed to contain the TAKA/NA2-tpi leader hybrid promoter, a fragment of the *Aspergillus oryzae* wA gene (SEQ ID NO: 5 for the full-length genomic DNA sequence and SEQ ID NO: 6 for the deduced amino acid sequence), the *Escherichia coli* hygB inverted repeat (hyg IR), the *Aspergillus niger* amyloglucosidase (AMG) terminator, and the *Aspergillus nidulans* pyrG gene as a selectable marker.

A 176 bp fragment of the *Aspergillus oryzae* wA gene (SEQ ID NO: 7 for the DNA sequence and SEQ ID NO: 8 for the deduced amino acid sequence thereof) was PCR amplified from plasmid plus wA flanking sequence rescued from *Aspergillus oryzae* strain P2-5.1 (WO 05/056772, Examples 27 and 28) using primers cwwanco.1corr (sense) and cwwanot.1a (antisense) shown below. The sense primer was engineered to have a Nco I site at the 5'-end and the antisense primer was engineered to have a Not I site at the 5'-end.

```
Primer cwwanco.1corr (sense):
                                (SEQ ID NO: 9)
5'-ccatggAGCACTTCGATTGCATTAG-3'

Primer cwwanot.1a (antisense):
                                (SEQ ID NO: 10)
5'-gcggccgcAGAACGAACGCAGGTTTTATAC-3'
``` wA sequence is shown in uppercase letters.

The amplification reactions (50 µl) were composed of 1× THERMOPOL® Reaction Buffer, 0.4 mM dNTPs, 100 ng of *Aspergillus oryzae* P2-5.1 DNA (WO 05/056772), 50 pmoles of primer cwwanco.1corr, 50 pmoles of primer cwwanot.1a, and 5 units of Taq DNA polymerase. The reactions were incubated in an EPPENDORF® MASTER-CYCLER® 5333 programmed for 30 cycles each for 30 seconds at 94° C., 30 seconds at 55° C., and 1 minute at 72° C. (7 minute final extension).

A PCR product of 188 bp was purified by 1% agarose gel electrophoresis in TAE buffer and further purified using a QIAQUICK® Gel Extraction Kit. The 188 bp PCR product was ligated with pCR2.1-TOPO® using a TOPO® TA Cloning Kit and transformed into ONE SHOT® TOP10 chemically competent *E. coli* cells according to the manufacturer's instructions. Plasmid DNA from several transformants was purified using a BIOROBOT® 9600 and analyzed by DNA sequencing to identify those containing the desired wA insert. One plasmid with the expected DNA sequence was designated MP#10.

Figure 3:
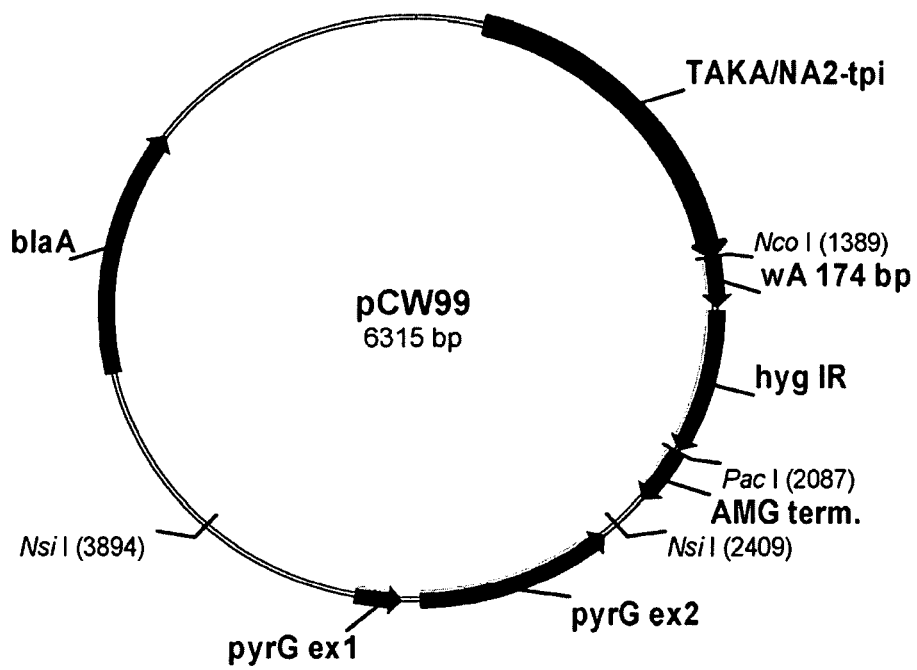
FIG. 3 shows a restriction map of pCW099.

MP#10 DNA was digested with Nco I and Not I and purified by 1% agarose gel electrophoresis in TAE buffer. The wA fragment was extracted using a QIAQUICK® Gel Extraction Kit. The purified fragment was ligated to Nco I/Not I digested pCW098 to create pCW099 (FIG. 3).

Example 3

Construction of Plasmid pEFer14

Plasmid pEFer14 was constructed to contain the TAKA/NA2-tpi leader hybrid promoter, a 176 bp fragment of the *Aspergillus oryzae* wA gene, the *Escherichia coli* hygB inverted repeat (hyg IR), the *Aspergillus niger* amyloglucosidase (AMG) terminator, and the full-length *Aspergillus nidulans* amdS gene as a selectable marker.

Figure 4:
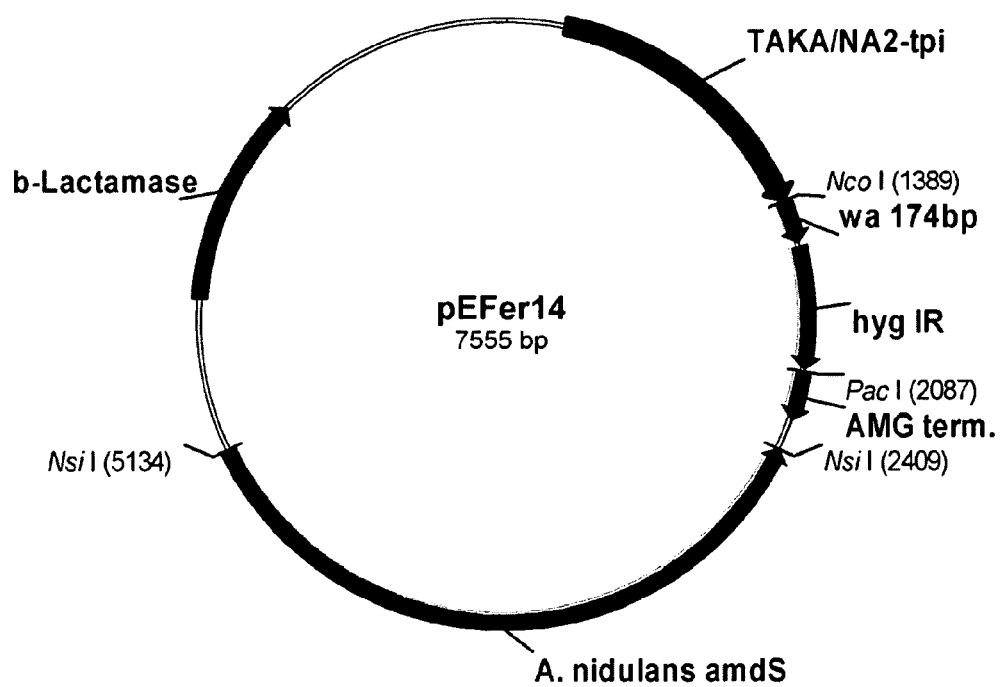
FIG. 4 shows a restriction map of pEFer14.

Plasmid pCW099 digested with Nco I and Pac I was purified by 1% agarose gel electrophoresis in TAE buffer. A 698 bp fragment containing the 176 bp wA fragment, and hygB inverted repeat was extracted using an ULTRA-FREE®-DA column (Millipore, Billerica, Mass., USA) according to the manufacturer's instructions. The purified fragment was ligated to Nco I/Pac I digested pAlLo1 (WO 05/056772, Example 1) to create pEFer14 (FIG. 4).

Example 4

Construction of Plasmid pDM261

Plasmid pDM261 was constructed to contain the TAKA/NA2-tpi leader hybrid promoter, the *Escherichia coli* hygB inverted repeat (hyg IR), the *Aspergillus niger* amyloglucosidase (AMG) terminator, and the full-length *Aspergillus nidulans* amdS gene as a selectable marker.

Figure 5:
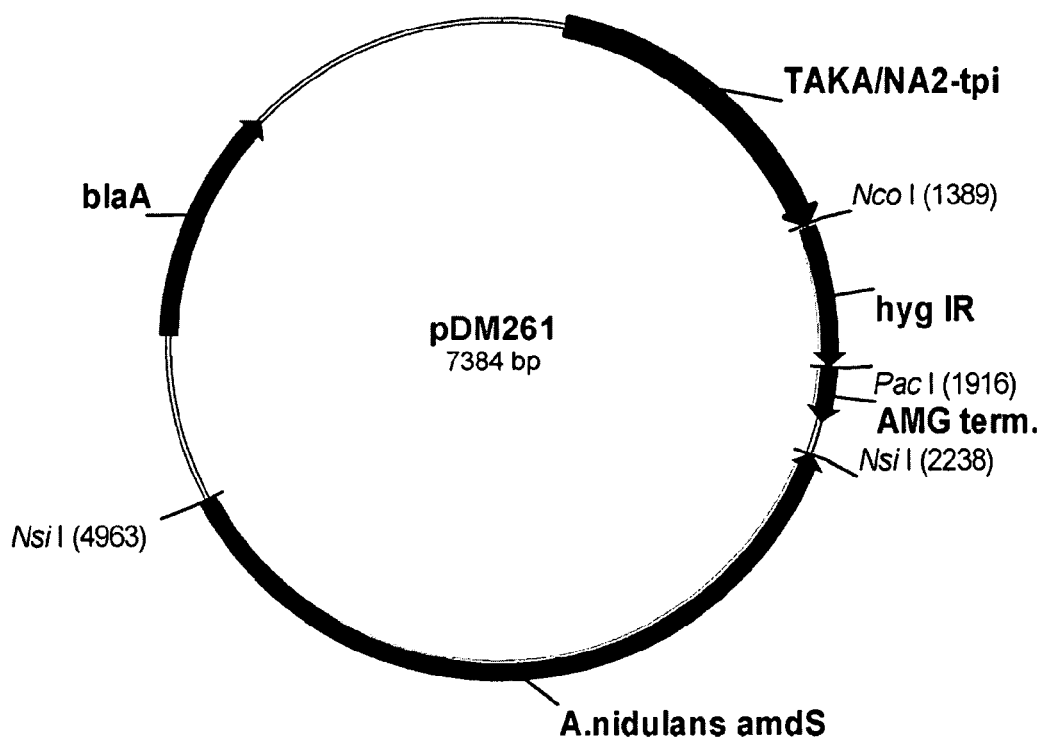
FIG. 5 shows a restriction map of pDM261.

Plasmid pCW098 digested with Nco I and Pac I was purified by 1% agarose gel electrophoresis in TAE buffer. The 527 bp fragment containing the hygB inverted repeat was extracted using an ULTRAFREE®-DA column. The purified fragment was ligated to Nco I/Pac I digested pAlLo1 to create pDM261 (FIG. 5).

Example 5

Construction of Plasmid pDM266

Plasmid pDM266 was constructed to contain the TAKA/NA2-tpi leader hybrid promoter, a 499 bp fragment of the *Aspergillus oryzae* wA gene, the *Escherichia coli* hygB inverted repeat (hyg IR), the *Aspergillus niger* amyloglucosidase (AMG) terminator, and the full-length *Aspergillus nidulans* amdS gene as a selectable marker.

A 499 bp fragment of the wA gene was amplified from *Aspergillus oryzae* strain A1560 (IFO 4177) genomic DNA using primers wA500FWD (sense) and wA500REV (antisense) shown below. The sense primer was engineered to have a Nco I site at the 5'-end and the antisense primer was engineered to have a Not I site at the 5'-end. *Aspergillus oryzae* strain A1560 (IFO 4177) genomic DNA was prepared using a DNEASY® Plant Maxi Kit (QIAGEN Inc., Valencia, Calif., USA) according to the manufacturer's instructions.

```
Primer wA500FWD (sense):
5'-ccatggGCGCTCAAAAACAACATCAAC-3'    (SEQ ID NO: 11)

Primer wAREV (antisense):
5'-gcggccgcAGAACGAACGCAGGTTTTAT-3'   (SEQ ID NO: 12)
``` wA sequence is shown in uppercase letters.

The amplification reactions (50 µl) were composed of 1× THERMOPOL™ Reaction Buffer, 0.2 mM dNTPs, 100 ng of *Aspergillus oryzae* strain A1560 genomic DNA, 50 pmoles of primer wA500FWD, 50 pmoles of primer wA500REV, and 2.5 units of Taq DNA polymerase. The reactions were incubated in an EPPENDORF® MASTERCYCLER® 5333 programmed for 30 cycles each for 30 seconds at 94° C., 30 seconds at 55° C., and 30 seconds at 72° C. (10 minute final extension).

A PCR product of 513 bp was purified by 1% agarose gel electrophoresis in TAE buffer and further purified using an ULTRAFREE®-DA column. The wA fragment was ligated with pCR2.1-TOPO® using a TOPO® TA Cloning Kit and transformed into ONE SHOT® TOP10 chemically competent *E. coli* cells according to the manufacturer's instructions. Plasmid DNA from several transformants was purified using a BIOROBOT® 9600 and analyzed by DNA sequencing to identify those containing the desired wA insert. One plasmid with the expected DNA sequence was designated MP#8.

Figure 6:
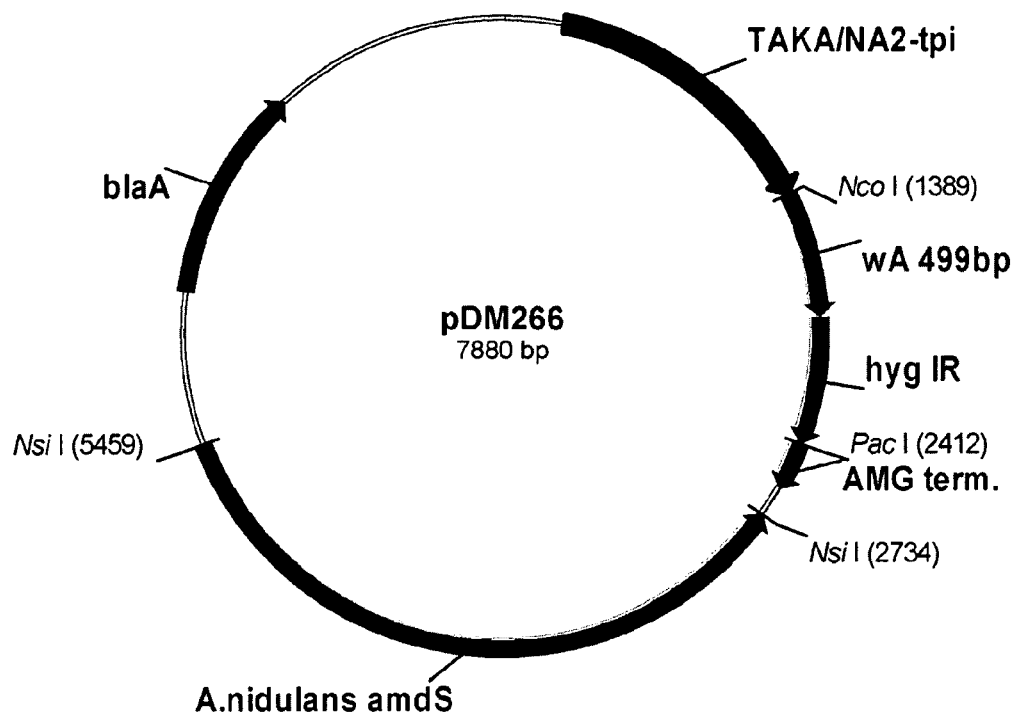
FIG. 6 shows a restriction map of pDM266.

MP#8 DNA was digested with Nco I and Not I and purified by 1% agarose gel electrophoresis in TAE buffer. The wA fragment was extracted using an ULTRAFREE®-DA column. The purified fragment was ligated to Nco I/Not I digested pDM261 to create pDM266 (FIG. 6).

The 499 bp wA fragment in pDM266 (basepairs 2607-3106 of the wA gene) has the same 3' end as the 176 bp wA fragment in pCW099 and pEFer14.

Example 6

Transformation of *Aspergillus oryzae* and Analysis of Transformants

*Aspergillus oryzae* strain JaL250 (WO 98/11203) was grown on a PDA plate supplemented with 20 mM uridine for 7 days at 34° C. Spores were collected by adding 5 ml of 0.01% TWEEN® 80 (Fisher Scientific, Fair Lawn, N.J., USA), scraping the surface of the plate using a sterile inoculating loop, and collecting the spore suspension with a 5 ml pipette. Approximately 2-5×10$^7$ spores were added to 100 ml of YPG medium in a 500 ml shake flask and incubated 16-18 hours at 30-34° C. and 140 rpm. Mycelia were collected using a sterile 0.2 µm 500 ml EXPRESS® filter unit (Millipore, Billerica, Mass., USA). Mycelia were filtered away from the growth medium, and then washed twice with 100 ml of 0.7 M KCl. Mycelia were re-suspended in 20 ml of protoplasting solution [5 mg/ml GLUCANEX® (Novozymes A/S, Bagsværd, Denmark) plus 0.5 mg/ml chitinase (Sigma Chemical Co., St. Louis, Mo., USA) in 0.7 M KCl]. Mycelia were transferred to a 125 ml shake flask and incubated at 34° C., 80 rpm for 30-90 minutes. Protoplasts were poured through a sterile funnel lined with MIRACLOTH™ (Calbiochem, San Diego, Calif., USA) into a sterile 50 ml polypropylene tube. Protoplasts were centrifuged 20 minutes at 1,303×g at room temperature in a Sorvall RT6000D centrifuge. The supernatant was discarded and protoplasts were re-suspended in 20 ml of STC. Protoplasts were centrifuged as above and re-suspended in 20 ml of STC. A 20 µl aliquot was removed and diluted with STC. Protoplasts were counted using a hemocytometer. The protoplasts were centrifuged as described above and re-suspended in the appropriate volume of STC to yield 2×10$^7$ protoplasts/ml.

Five µg of pEFer14, pDM261, or pDM266 DNA were added to 100 µl of *Aspergillus oryzae* JaL250 protoplasts. After incubation at room temperature for 30 minutes, the protoplast/DNA mix was adjusted to 9 ml with STC, split into 3 aliquots, and spread onto three 150 mm COVE plates supplemented with 20 mM uridine and 1% maltose. The plates were then incubated at 34° C. Growth on acetamide required expression of the amdS gene present on each expression plasmid.

After 4 days of incubation, before mature spore coloration was apparent, 25 or 30 primary transformants obtained using plasmids pEFer14, pDM261, and pDM266 were streaked onto COVE2 plates supplemented with 20 mM uridine and 1% maltose. All colonies derived from transformants of pDM261 were uniformly dark green. In contrast, colonies obtained from transformants of pEFer14 or pDM266 varied in spore color ranging from light yellow to dark green. The transformants were purified by streaking spores to COVE2 plates supplemented with 20 mM uridine and 1% maltose and then picking isolated colonies to plates of the same medium. All plates were incubated at 34° C.

The results are shown in Table 1. Forty percent of the 30 spore purified pDM266 (499 bp wA) transformants showed spore coloration that was lighter than the wild-type. Thirty percent of the 30 spore purified pEFer14 (176 bp wA) transformants showed spore coloration that was lighter than wild-type. One hundred percent of the 25 spore purified pDM261 (no wA) transformants showed wild-type spore coloration.

TABLE 1

| Plasmid | Transcribable region | % light colored | % wildtype | # screened |
| --- | --- | --- | --- | --- |
| pEFer14 | 176 bp wA, hyg IR | 30 | 70 | 30 |
| pDM266 | 499 bp wA, hyg IR | 40 | 60 | 30 |
| pDM261 | hyg IR | 0 | 100 | 25 |

The results showing light spore coloration of the pDM266 and pEFer14 transformants indicated a phenotype consistent with suppression of the wA gene by transitive RNAi.

Example 7

Southern Blot Analysis of wA Gene Silenced *Aspergillus oryzae* Transformants

Southern blot analysis was performed to verify that varying spore coloration in six selected transformants from Example 6, as listed below in Table 2, were not the result of gene disruptions. Mutant *Aspergillus oryzae* P2-5.1 (WO 2005/056772) contained a disruption of the wA gene.

TABLE 2

| Strain Name | Spore Color |
| --- | --- |
| JaL250 (untransformed) | Wild-type |
| DLM1610-45-pDM261#2 | Wild-type |
| P2-5.1 | white |
| DLM1641-74-pEFer14#3 | light colored |
| DLM1641-74-pDM266#17 | white |
| DLM1641-74-pDM266#24 | Light colored |
| DLM1641-74-pDM266#29 | white |

Genomic DNA from each of the above *Aspergillus oryzae* strains was prepared using a DNEASY® Plant Maxi Kit according to the manufacturer's instructions. Two µg of each genomic DNA were digested with Sap I and Cla I overnight at 37° C. Digested genomic DNA was fractionated by 0.7% agarose gel electrophoresis in TAE buffer for 17 hours and blotted onto a NYTRAN® SuPerCharged membrane (Schleicher & Schuell BioScience, Keene, N.H., USA) using a TURBOBLOTTER™ (Schleicher & Schuell BioScience, Keene, N.H., USA) for 14-16 hours, following the manufacturer's recommendations.

The membrane was first hybridized with a 463 bp digoxigenin-labeled *Aspergillus oryzae* wA probe, which was synthesized by incorporation of digoxigenin-11-dUTP by PCR using primer wA5primeFWD (sense) and primer wA5primeREV (antisense) shown below:

```
Primer wA5primeFWD (sense):
5'-TACTACGGAGACCTTGGAAA-3'         (SEQ ID NO: 13)

Primer wA5primeREV (antisense):
5'-GCTCTTAGACAGCCTAGAAT-3'         (SEQ ID NO: 14)
```

The amplification reaction (50 µl) was composed of 1× THERMOPOL™ Reaction Buffer, 5 µl of PCR DIG Labeling Mix (Roche Applied Science, Indianapolis, Ind., USA), 10 ng of *Aspergillus oryzae* JaL250 genomic DNA (prepared using a DNEASY® Plant Maxi Kit), 10 pmol of primer wA5primeFWD, 10 pmol of primer wA5primeREV, and 2.5 units of Taq DNA polymerase. The reaction was incubated in an EPPENDORF® MASTERCYCLER® programmed for 30 cycles each for 30 seconds at 95° C., 30 seconds at 52° C., and 1 minute at 72° C. (7 minute final extension). The PCR reaction was purified by 0.8% agarose gel electrophoresis in TAE buffer where incorporation of digoxigenin was indicated by an increase in molecular mass. A 463 bp product band was excised from the gel and purified using a MINELUTE® Gel Extraction Kit (QIAGEN Inc., Valencia, Calif., USA) according to the manufacturer's instructions.

Hybridization was performed in DIG Easy Hyb buffer (Roche Applied Science, Indianapolis, Ind., USA) at 42° C. for 15-17 hours. The membrane was then washed twice under high stringency conditions in 2×SSC plus 0.1% SDS for 5 minutes at room temperature followed by two washes in 0.5×SSC plus 0.1% SDS for 15 minutes each at 650° C. The probe-target hybrids were detected by a chemiluminescent assay (Roche Applied Science, Indianapolis, Ind., USA) following the manufacturer's instructions.

Southern blot analysis performed on the transformants revealed that in all transformants, hybridization bands were of the same size as that of *Aspergillus oryzae* host strain JaL250 containing the full-length wA gene compared to a significantly smaller hybridized band in P2-5.1. The results demonstrated that the non-wild-type spore colors were not the result of gene disruptions.

Example 8

Extraction of RNA from *Aspergillus oryzae* Transformants

Six *Aspergillus oryzae* transformants (Example 6) displaying varied spore colors were spread on COVE2 plates supplemented with 20 mM uridine and 1% maltose and cultivated for 7 days at 34° C. Spores of untransformed *Aspergillus oryzae* JaL250 were spread on PDA plates supplemented with 20 mM uridine and cultivated for 7 days at 34° C.

Following the addition of 5 ml of 0.01% TWEEN® 80, spores for each strain were collected by scraping the surface of the plate using a sterile disposable spreader (Arben Bioscience, Rochester, N.Y., USA). Each spore suspension was drawn up into a sterile 5 ml serological pipette, added to 75 ml of Minimal medium (pH 6.5) supplemented with 10 mM uridine and 1% maltose in a 500 ml shake flask, and cultivated for 22-24 hours at 34° C. and 65 rpm. A 47 mm cellulose nitrate filter (Whatman Inc., Florham Park, N.J., USA) was placed on top of a filter membrane in a sterile 0.2 µm 250 ml MF75 filter unit (Nalgene, Rochester, N.Y., USA). Twenty five to 75 ml of each whole culture broth were placed onto separate cellulose nitrate filters and subjected to vacuum filtration to produce a thin layer of mycelia on the filter. The cellulose nitrate filters plus mycelia were transferred to 60 mm Petri dishes containing Minimal medium agar (pH 6.5) supplemented with 10 mM uridine and 1% maltose. The agar plates were placed in a plastic bag, sealed, and incubated at 37° C.

When pigmented conidiaphores began to appear (42-48 hours) in the *Aspergillus oryzae* JaL250 control, 120 mg of mycelia were scraped from each filter using a spatula and each transferred to a Lysing Matrix C tube (Q-Biogene, Irvine, Calif., USA) containing 1 ml of RNAPRO™ Solution (Q-Biogene, Irvine, Calif., USA). The Lysing Matrix C tubes were securely capped to prevent leakage during homogenization. The sample tubes were processed for 40 seconds at speed 6 in a FASTPREP® FP120 Instrument (Q-Biogene, Irvine, Calif., USA), and then placed on ice for 2 minutes. The sample tubes were processed again for 40 seconds at speed 6, and then placed on ice for 2 minutes. The samples were centrifuged at 13,400×g in an EPPENDORF® 5415D microcentrifuge for 5 minutes at 4° C. The resulting supernatants were transferred to 1.7 ml microcentrifuge tubes, and then incubated for 5 minutes at room temperature. Three-hundred µl of chloroform were added to the sample tubes and vortexed for 10 seconds. After incubation at room temperature for 5 minutes, the samples were centrifuged at 13,400×g in an EPPENDORF® 5415D microcentrifuge for 5 minutes at 4° C. The upper phase of each sample was transferred to a new 1.7 ml microcentrifuge tube, and then incubated for 5 minutes at room temperature. Again, 300 µl of chloroform were added to the samples and vortexed for 10 seconds. The samples were incubated for 5 minutes at room temperature, followed by centrifugation at 13,400×g in an EPPENDORF® 5415D microcentrifuge for 5 minutes at 4° C. The upper phases were transferred to new 1.7 ml microcentrifuge tubes. Five-hundred µl of ice cold ethanol was added to the sample tubes and incubated for 30 minutes at −20° C. The samples were centrifuged at 13,400×g in an EPPENDORF® 5415D microcentrifuge for 20 minutes at 4° C. The resulting supernatants were removed and the pellets washed with 75% ethanol. The ethanol was removed and the pellets were allowed to air-dry for 5 minutes at room temperature. The pellets were resuspended in 100 µl of diethylpyrocarbonate (DEPC)-treated water followed by the addition of 50 μl of 8 M lithium chloride (VWR, West Chester, Pa., USA). The samples were incubated for 1 hour at −20° C. After incubation, the samples were centrifuged at 13,400×g in an EPPENDORF® 5415D microcentrifuge for 25 minutes at 4° C. The supernatants were removed from the sample tubes, and the RNA pellets were rinsed with 70% ethanol. The ethanol was removed, and the RNA pellets were resuspended in 25-40 μl of DNase, RNase-free water (Sigma-Aldrich, St. Louis, Mo., USA). RNA concentration was quantified using a NANODROP® 1000 Spectrophotometer (Nanodrop Technologies, Wilmington, Del., USA).

Example 9

Treatment of *Aspergillus oryzae* RNA with DNase

Contaminating genomic DNA was removed from the *Aspergillus oryzae* RNA samples (Example 8) using a TURBO DNA-Free™ Kit (Ambion, Austin, Tex., USA). Three μg of extracted RNA were combined with 1× TURBO DNase™ Buffer (Ambion, Austin, Tex., USA) and adjusted to a volume of 10 μl with DNase, RNase-free water. One unit of TURBO DNase™ (Ambion, Austin, Tex., USA) was added to the sample and incubated for 30 minutes at 37° C. Another 1 unit of TURBO DNase™ was added and the sample was incubated for 1 hour at 37° C. Two μl of DNase Inactivation Reagent (Ambion, Austin, Tex., USA) were added. The contents of the sample tubes were mixed 3 times during a 2 minute incubation period at room temperature to redisperse the DNase Inactivation Reagent. The DNase Inactivation Reagent was pelleted by centrifugation for 2 minutes at 9,300×g in an EPPENDORF® 5415D microcentrifuge. Nine μl of each supernatant was transferred to a 0.65 ml microcentrifuge tube. One μl of DNase-treated RNA was measured using a NANODROP® 1000 Spectrophotometer in order to determine RNA concentration.

Example 10

Synthesis of First Strand cDNA from *Aspergillus oryzae* Total RNA Samples

First strand cDNA was synthesized from each of the extracted *Aspergillus oryzae* RNA samples (Example 9) using a Transcriptor First Strand cDNA Synthesis Kit (Roche Applied Science, Indianapolis, Ind., USA). One μg of DNase-treated RNA was combined with 1.2 nmol of random hexamer primer (Roche Applied Science, Indianapolis, Ind., USA) and adjusted to a volume of 13 μl with DEPC-treated water. The sample was incubated for 10 minutes at 65° C., and then placed on ice. The 13 μl sample was combined with 1× Transcriptor RT Reaction Buffer (Roche Applied Science, Indianapolis, Ind., USA), 20 units of Protector RNase Inhibitor (Roche Applied Science, Indianapolis, Ind., USA), 10 mM deoxynucleotide mix, and 10 units of Transcriptor Reverse Transcriptase (Roche Applied Science, Indianapolis, Ind., USA) in a final volume of 20 μl. The reaction mixture was incubated for 10 minutes at 25° C., 60 minutes at 50° C., and 5 minutes at 85° C. After synthesis, the sample tubes were placed on ice.

To verify removal of contaminating genomic DNA and check integrity of the cDNA, the sample was PCR amplified with wA and actin primer sets that span introns shown below.

```
Primer 2wAFWD (sense):
5'-ATGCCTCGCAGCTTATAGGA-3'         (SEQ ID NO: 15)

Primer 2wAREV (antisense):
5'-CGCACTGATATACGGTTTGG-3'         (SEQ ID NO: 16)

Primer 2actinFWD (sense):
5'-GGATCTCTACGGTAACATCGTCA-3'      (SEQ ID NO: 17)

Primer 2actinREV (antisense):
5'-GATCGGAGATGCCAGGGTA-3'          (SEQ ID NO: 18)
```

The amplification reactions (50 μl) were composed of 1× THERMOPOL™ Reaction Buffer, 0.4 mM dNTPs, 2 μl of template cDNA sample, 50 μmol of primer 2wAFWD, 50 pmol of primer 2wAREV, and 2.5 units of Taq DNA polymerase. A control amplification reaction (50 μl) was composed of 1× THERMOPOL™ Reaction Buffer, 0.4 mM dNTPs, 10 ng of *Aspergillus oryzae* JaL250 genomic DNA (prepared using a DNEASY® Plant Maxi Kit), 50 pmol of primer 2wAFWD, 50 pmol of primer 2wAREV, and 2.5 units of Taq DNA polymerase. The reactions were incubated in an EPPENDORF® MASTERCYCLER™ programmed for 30 cycles each for 30 seconds at 95° C., 30 seconds at 50° C., and 1 minute at 72° C. (7 minute final extension). The PCR reactions were purified by 0.8% agarose gel electrophoresis in TAE buffer. The results showed that PCR reactions using cDNA templates produced a smaller amplicon than the control PCR reactions using genomic DNA as templates. A PCR amplicon generated from genomic DNA will be larger than the corresponding amplicon generated from cDNA. Therefore, the cDNA preparations did not contain detectable amounts of genomic DNA.

Example 11

Detection of Steady-State wA mRNA *Aspergillus oryzae* by Real Time PCR (RT-PCR)

Determination of *Aspergillus oryzae* wA expression levels in the transformants was accomplished using RT-PCR. Complementary DNA (cDNA) synthesized from each transformant as described in Example 10 was used as a template for RT-PCR reactions. The wA gene served as the target DNA sequence, while the *Aspergillus oryzae* actin gene (SEQ ID NO: 19 for the DNA sequence and SEQ ID NO: 20 for the deduced amino acid sequence) served as the endogenous control, as well as the reference DNA sequence. Primers and their corresponding mono-color hydrolysis probes were selected and designed according to the Universal ProbeLibrary Assay Design Software Guide (Roche Applied Science, Indianapolis, Ind., USA). The probes were first selected based on the desired transcript DNA sequence near exon-exon splice junctions. The primer sets were then designed to amplify targets that span the same exon-exon splice junctions, or introns. The following probes were selected:

```
Universal ProbeLibrary Probe #131
(actin-reference)
5'-CTGGTGGT-3'

Universal ProbeLibrary Probe #134 (wA-target)
5'-CCTCCTTC-3'
```

The following primers were used:

```
Primer 2wAFWD (sense):
5'-ATGCCTCGCAGCTTATAGGA-3'          (SEQ ID NO: 21)

Primer 2wAREV (antisense):
5'-CGCACTGATATACGGTTTGG-3'          (SEQ ID NO: 22)

Primer 2actinFWD (sense):
5'-GGATCTCTACGGTAACATCGTCA-3'       (SEQ ID NO: 23)

Primer 2actinREV (antisense):
5'-GATCGGAGATGCCAGGGTA-3'           (SEQ ID NO: 24)
```

The Relative Quantification Real-Time PCR assay was performed using a LIGHTCYCLER® 480 System (Roche Applied Science, Indianapolis, Ind., USA). Each RT-PCR reaction (20 µl) was composed of 1× LIGHTCYCLER® 480 Probes Master mix (Roche Applied Science, Indianapolis, Ind., USA), 200 nM sense primer, 200 nM antisense primer, 100 nM probe, and varying dilutions (i.e., undiluted, 1:10, 1:100, 1:1000) of cDNA template. The RT-PCR reactions were carried out in a LIGHTCYCLER® 480 System programmed for 45 cycles each for 10 seconds of denaturation at 95° C. and 30 seconds at 60° C. for both quantification and extension of amplified product. Each sample was prepared in triplicate using 384 well plates (Roche Applied Science, Indianapolis, Ind., USA). A negative control in which the template cDNA was replaced with PCR-grade water was run on every 384 well plate tested to reveal putative false-positive results.

Data obtained from the LIGHTCYCLER® 480 System was analyzed using LIGHTCYCLER® 480 Relative Quantification Software (Roche Applied Science, Indianapolis, Ind., USA). In the Relative Quantification method, each sample was corrected for differences in quality and quantity caused by discrepancies in initial sample concentration, variations in sample loading, pipetting errors, or disparities in cDNA synthesis efficiency by calculating the target gene concentration relative to a non-regulated reference gene. The target gene/reference gene ratio was not only determined, but also normalized by a calibrator that corrects for any differences in PCR efficiencies of the target and reference genes. The Relative Quantification analysis results were expressed as a normalized ratio in which the ratio of the target DNA sequence to the reference DNA sequence in a sample was divided by the ratio of the same two sequences in a standard sample or the calibrator.

A standard curve was first generated for both the target and reference using untransformed *Aspergillus oryzae* JaL250 as the standard sample. The standard curves yielded $R^2$ values of 0.996 and 0.995 for the target and reference, respectively. The PCR efficiency values calculated by the Roche LIGHTCYCLER® 480 Relative Quantification Software were 1.757 (error 0.0449) and 1.907 (error 0.0287) for the target and reference, respectively. In order to compare the relative expression levels of mRNA across all the strains listed in Example 7, real-time PCR reactions were carried out as described above. Data was collected and analyzed using the LIGHTCYCLER® 480 Relative Quantification Software and compared to the previously generated standard curves according to Roche LIGHTCYCLER® 480 Relative Quantification Software Manual (Roche Applied Science, Indianapolis, Ind., USA). Using Relative Quantification analysis, the expression level of wA mRNA in *Aspergillus oryzae* DLM1610-45-pDM261#2, the transformant with wild-type spore color, was comparable to the untransformed *Aspergillus oryzae* JaL250 strain. Relative expression levels of wA mRNA in *Aspergillus oryzae* DLM1641-74-pE-Fer14#3 and *Aspergillus oryzae* DLM1641-74-pDM266#24, transformants with light colored spores, showed a 67% and 62% reduction, respectively, as compared to the wA mRNA expression level in the strains with wild-type spore color. *Aspergillus oryzae* DLM1641-74-pDM266#17 and *Aspergillus oryzae* DLM1641-74-pDM266#29, strains with white spores, showed a 73% and 81% reduction in wA mRNA compared to the strains with wild-type spore color.

Example 12

Construction of Plasmid pAmFs031

A transitive RNAi expression vector was constructed for suppressing the expression of an *Aspergillus niger* ATCC 1015 polyketide synthase gene (SEQ ID NO: 25 for the cDNA sequence and SEQ ID NO: 26 for the deduced amino acid sequence).

Plasmid pAmFs031 was constructed to contain the TAKA/NA2-tpi leader hybrid promoter, a fragment of the open reading frame for the *Aspergillus niger* polyketide synthase gene, the *Escherichia coli* hygB inverted repeat (hyg IR), the *Aspergillus niger* amyloglucosidase terminator, and the full-length *Aspergillus nidulans* amdS gene (Kelly and Hynes, 1985, *EMBO J.* 4: 475-479) as a selectable marker. The *Aspergillus niger* polyketide synthase gene was selected as a silencing target because of its sequence identity to other polyketide synthases involved in conidial pigment biosynthesis in filamentous fungi.

A 502 base pair fragment from within the *Aspergillus niger* polyketide synthase open reading frame (SEQ ID NO: 27 for DNA sequence and SEQ ID NO: 28 for the deduced amino acid sequence) was amplified from genomic DNA isolated from *Aspergillus niger* strain MBin120 (WO 2004/090155) using a sense strand primer possessing a 5' Nco I restriction site and an antisense primer possessing a 5' Not I restriction site shown below.

```
Primer 56896F (sense):
                                    (SEQ ID NO: 29)
5'-ggggccatggTCAGCGCGGTAAGCTCTAAT-3'

Primer 56896R (antisense):
                                    (SEQ ID NO: 30)
5'-gggggcggccgcGTAAGGTTCCGCATTTCTGG-3'
```

Polyketide Synthase Coding Sequence Shown in Uppercase Letters.

The amplification reaction (50 µl) was composed of 1× HERCULASE® Reaction Buffer (Stratagene, La Jolla, Calif., USA), 0.2 mM dNTPs, 128 ng of *Aspergillus niger* MBin120 genomic DNA (prepared using a DNEASY® Plant Maxi Kit), 20 pmoles of sense primer, 20 pmoles of antisense primer, and 2.5 units of HERCULASE Hotstart DNA polymerase (Stratagene, La Jolla, Calif., USA). The reactions were incubated in an EPPENDORF® MASTERCYCLER® 5333 programmed for 30 cycles each for 30 seconds at 94° C., 30 seconds at 55° C., and 1 minute at 72° C. (7 minute final extension).

Figure 7:
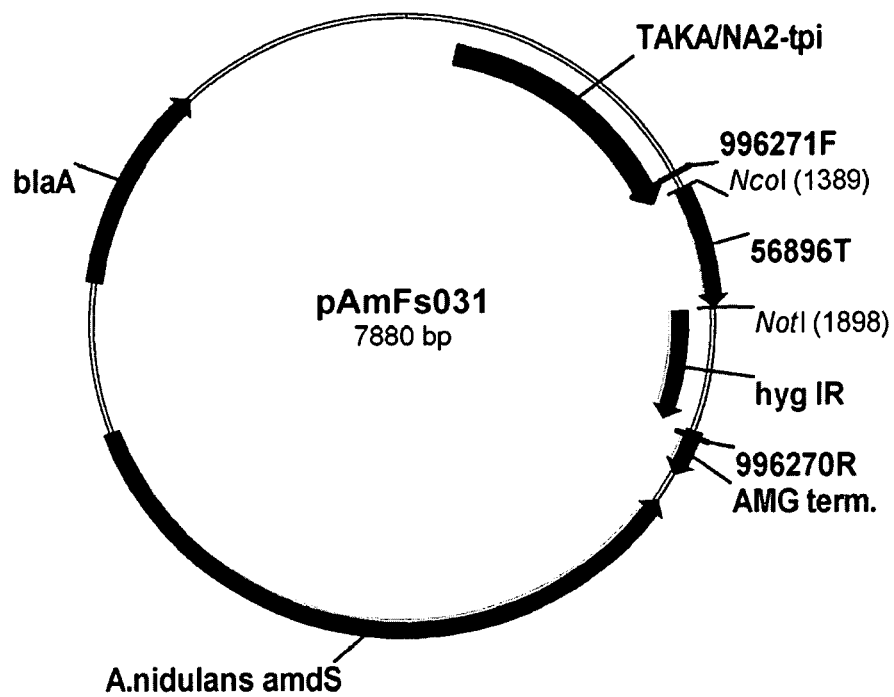
FIG. 7 shows a restriction map of pAmFs031.

The resulting PCR product of 502 bp and pDM261 were digested with Nco I and Not I, purified by 0.75% agarose gel electrophoresis in TAE buffer, and further purified using a MINELUTE® Kit for the PCR product or a QIAQUICK® Gel Extraction Kit for the plasmid. The PCR product was ligated with the pDM261 plasmid fragment using a FAST- LINK™ DNA Ligation Kit (Epicentre Biotechnologies, Madison, Wis., USA) and transformed into SURE™ II chemically competent *E. coli* cells according to the manufacturer's instructions (Stratagene, La Jolla, Calif., USA). Plasmid DNA from several transformants was purified using a BIOROBOT® 9600 and analyzed by DNA sequencing to identify those containing the desired polyketide synthase insert. One plasmid with the expected DNA sequence was designated pAmFs031 (FIG. 7).

Example 13

Transformation of *Aspergillus niger* and Analysis of Transformants

*Aspergillus niger* strain MBin120 was grown on a PDA plate for 14 days at 34° C. Spores were collected by adding 7 ml of 0.01% TWEEN® 20 (Fisher Scientific, Fair Lawn, N.J., USA), scraping the surface of the plate using a sterile inoculating loop, and collecting the spore suspension with a 5 ml pipette. A 500 ml glass shake flask containing 25 ml of YPG medium supplemented with 1 M sucrose was inoculated with $2.6 \times 10^8$ spores and incubated 15 hours at 28° C. at 150 rpm. Mycelia were collected using a sterile 0.2 μm 500 ml EXPRESS® filter unit (Millipore, Billerica, Mass., USA). Mycelia were filtered from the growth medium, and then washed twice with 150 ml of 1 M sorbitol. Mycelia were resuspended in 30 ml of protoplasting solution containing 20 mg of GLUCANEX® and 0.4 mg of chitinase per ml of 1 M sorbitol. Mycelia were transferred to a 125 ml glass shake flask and incubated at 34° C., 100 rpm for 45 minutes. Protoplasts were poured through a sterile funnel lined with MIRACLOTH™ into a sterile 50 ml polypropylene tube. The tube was then filled with ice cold 1 M sorbitol. The protoplasts were centrifuged for 5 minutes at 1,303×g at room temperature in a Sorvall RT6000D centrifuge. The supernatant was discarded and the protoplasts were re-suspended in 50 ml of 1 M sorbitol. The protoplasts were centrifuged in a Sorvall RT6000D centrifuge and re-suspended in 10 ml of STC. A 20 μl aliquot was removed and diluted with STC. The protoplasts were counted using a hemocytometer. The protoplasts were centrifuged in a Sorvall RT6000D centrifuge and re-suspended in the appropriate volume of PEG 4000 (Polysciences, Inc., Warrington, Pa., USA) to yield $2 \times 10^7$ protoplasts/ml.

Five μg of pAmFs031 or pDM261 DNA were added to 100 μl of the *Aspergillus niger* MBin120 protoplasts. After incubation on ice for 30 minutes, 1 ml of SPC was added to the protoplast/DNA solutions and gently mixed. The solutions were incubated for 30 minutes at room temperature. Then 10 ml of dissolved amdS overlay agar cooled to 50° C. was added to the transformation mixtures and spread onto 150 mm COVE plates. The plates were then incubated at 34° C. Growth on acetamide required expression of the amdS gene present on each expression plasmid.

After 4 days of incubation, 10 primary transformants were obtained for each of pAmFs031 and pDM261. The transformants were streaked onto COVE A minus urea plus acetamide plates supplemented with 1% maltose. All colonies derived from pDM261 were uniformly dark black. In contrast, the colonies obtained from the pAmFs031 transformants varied in spore color ranging from white to dark brown. The transformants were purified by streaking spores to COVE A minus urea plus acetamide plates supplemented with 1% maltose and then picking isolated colonies to plates of the same medium. Strain purification was repeated four times in total. All plates were incubated at 34° C.

Three of the 10 spore purified pAmFs031 transformants displayed spore coloration that was lighter than the wild-type. All of the 10 spore purified pDM261 "empty vector" transformants showed wild-type spore coloration. These results showing light spore coloration for the pAmFs031 transformants indicated a phenotype consistent with transitive RNAi associated suppression of the polyketide synthase gene.

Example 14

Growth and Total RNA Extraction from Polyketide Synthase Silenced and Control *Aspergillus niger* Strains The following *Aspergillus niger* strains were grown for 7 days on COVE A minus urea plus acetamide plates supplemented with 1% maltose at 34° C.: two *Aspergillus niger* pAmFs031 strains with white spores (designated pAmFs031-W1 and pAmFs031-W2), one *Aspergillus niger* pAmFs031 strain with black spores (designated pAmFs031-B1), and one *Aspergillus niger* strain transformed with pDM261. The untransformed control strain *Aspergillus niger* MBin120 was grown on PDA plates. Spores were collected from each strain by adding 5 ml of 0.01% TWEEN® 20, scraping the surface of the plate with a sterile inoculating loop, and collecting the spore suspension with a 10 ml pipette. Forty μl of spore suspension were mixed with 10 ml of M410 medium and 1 ml of this mixture was added to each well of a 24 well polystyrene microtiter plate (Corning Incorporated, Corning, N.Y., USA). Each strain was grown in a separate microtiter plate to avoid cross contamination. The plates were incubated at 34° C. for 4 days in a humidity controlled chamber at which point the fungi formed a continuous mat of mycelial growth across the well and pigmented conidiaphores were present for all strains.

Total RNA was extracted from the mycelial mats using a RNAPRO™ Pro Red Kit (Q-Biogene, Irvine, Calif., USA). The mats were removed from the wells and placed onto a paper-towel to absorb any excess medium. Totally 200 mg of each mycelial mat tissue were transferred to a FAS-TRNA® ProRed tube containing 1 ml of RNAPRO™ solution (Q-Biogene, Irvine, Calif., USA). The mycelia were homogenized for 40 seconds at speed 6 using a FAST-PREP® FP120 Instrument. Each sample was centrifuged at 13,400×g in a Sorvall MC12V microcentrifuge for 5 minutes at 4° C. The aqueous phases were transferred to 1.7 ml microfuge tubes. The samples were incubated at room temperature for 5 minutes. Three hundred μl of chloroform were added and the samples were vortexed 10 seconds and then incubated at room temperature for 5 minutes. The samples were centrifuged at 13,400×g in a Sorvall MC12V microcentrifuge for 5 minutes at 4° C. The upper phases were transferred to new 1.7 ml microfuge tubes. The samples were extracted again with chloroform as described above. Five hundred μl of ice cold ethanol were added and the samples were stored at −20° C. for one hour. The samples were centrifuged at 13,400×g in a Sorvall MC12V microcentrifuge for 20 minutes at 4° C. The ethanol was removed and the pellets were washed with 75% ethanol. The ethanol was removed and the pellets were air dried for 5 minutes. The RNA samples were resuspended in 100 μl of DEPC-treated water. Fifty μl of 8 M LiCl were added and the samples were stored for 1 hour at −20° C. The samples were centrifuged at 13,400×g in a Sorvall MC12V microcentrifuge for 25 minutes at 4° C. The LiCl was removed and 500

μl of 75% ethanol were added to the pellets and then removed. The pelleted samples were air dried for 5 minutes. The RNA samples were resuspended in 30 μl of DEPC-treated water. The RNA concentration was measured using a NANODROP® 1000 Spectrophotometer. Samples were stored at −80° C.

Example 15

First Strand cDNA Synthesis

RNA samples from each of the *Aspergillus niger* strains described in Example 14 were treated with DNase to remove genomic DNA using reagents from a TURBO DNase™ Kit (Ambion, Inc., Austin, Tex., USA). Three μg of RNA were combined with 1 μl of TURBO DNase™ buffer (Ambion, Inc., Austin, Tex., USA) and adjusted to a volume of 10 μl with DEPC-treated water. A 0.5 μl aliquot of TURBO DNase™ (Ambion, Inc., Austin, Tex., USA) was added and the sample was incubated 30 minutes at 37° C. A second 0.5 μl aliquot of TURBO DNase™ was added and the sample was again incubated for 30 minutes at 37° C. Two μl of Inactivation Reagent (Ambion, Inc., Austin, Tex., USA) were added and the sample was mixed three times during a 2 minute incubation at room temperature. The sample was centrifuged for 2 minutes at 9,300×g in an EPPENDORF® 5415D microcentrifuge. Nine μl of supernatant were transferred to a 0.6 ml microfuge tube. The RNA concentration was measured using a NANODROP® 1000 Spectrophotometer. Samples were stored at −80° C.

First strand cDNA was synthesized using a Transcriptor Reverse Transcriptase First Strand cDNA Synthesis Kit (Roche Applied Science, Indianapolis, Ind., USA). Four libraries were prepared for each of the five *Aspergillus niger* strains described in Example 14 using different quantities of DNase-treated RNA: 300 ng, 600 ng, 900 ng, and 1.2 μg in a volume of 1 to 2 μl combined with 2 μl of random hexamer primer (Roche Applied Science, Indianapolis, Ind., USA) and adjusted to a volume of 13 μl with DEPC-treated water. The sample were incubated for 10 minutes at 65° C. and then placed on ice. A 6.5 μl aliquot of Transcriptor Reverse Transcriptase master mix (4 μl of Transcriptor Reverse Transcriptase buffer, 0.5 μl of Protector RNase inhibitor, and 2 μl of dNTP mix) were added to a tube followed by the addition of a 0.5 μl aliquot of Transcriptor Reverse Transcriptase. The samples were removed from the ice and transferred to an EPPENDORF® MASTERCYCLER® 5333 programmed for 10 minutes at 25° C., 60 minutes at 55° C., and then 5 minutes at 85° C. Samples were stored at −80° C.

Example 16

Detection of *Aspergillus niger* Polyketide Synthase mRNA by Real-Time PCR

The relative expression levels of *Aspergillus niger* polyketide synthase mRNA by the *Aspergillus niger* strains described in Example 14 were quantified by RT-PCR. Total RNA was extracted from each strain to serve as a template for first strand cDNA synthesis as described in Example 15. The first strand cDNA served as a template for RT-PCR. The *Aspergillus niger* actin gene was used as a reference standard (i.e., internal control). Probes and primers were designed using the Roche Universal ProbeLibrary Design Center Software (Roche Applied Science, Indianapolis, Ind., USA). The following primers and probe pairs were used:

```
Aspergillus niger polyketide synthase forward
primer (62488):
5'-tcgtgaatcaggtcctagcc-3'          (SEQ ID NO: 31)

Aspergillus niger polyketide synthase reverse
primer (62489):
5'-aaacaacccaattggtagatgc-3'        (SEQ ID NO: 32)

Roche Universal ProbeLibrary Probe #80
(04689038001):
5'-cctggaga-3'

Aspergilus niger actin forward primer (62520):
5'-atctgtacggcaacattgtca-3'         (SEQ ID NO: 33)

Aspergillus niger actin reverse primer (62521):
5'-ttctgcatacggtcggagat-3'          (SEQ ID NO: 34)

Roche Universal ProbeLibrary Probe #131
(04694155001):
5'-ctggtggt-3'
```

The RT-PCR assay was performed using a LIGHTCYCLER® 480 System and the above Roche Universal ProbeLibrary Probes, which were pre-labeled with fluorescein at the 5'-end and a dark quencher dye near the 3'-end. Each reaction mixture contained 10 μl of LIGHTCYCLER® 480 Probes Master Mix, 0.1 μM Roche Universal ProbeLibrary Probe, 0.2 μM forward primer, 0.2 μM reverse primer, and 2 μl of first strand cDNA (produced as described in Example 15 from varying amounts of total RNA) in a total volume of 20 μl. All RT-PCR reactions were carried out in 384 well plates (Roche Applied Science, Indianapolis, Ind., USA). RT-PCR reactions were carried out in a LIGHTCYCLER® 480 System programmed for 1 cycle of preincubation at 95° C. for 10 minutes, 4.8° C./s; 45 cycles of amplification using the Quantification Analysis mode at 95° C. for 10 seconds, 4.8° C./s; 55° C. for 15 seconds, 2.5° C./s; 72° C. for 1 second, 4.8° C./s (in acquisition mode Single); and 1 cycle of cooling at 40° C. for 10 seconds, 2° C./s. In order to generate standard curves and PCR efficiency values for the target (polyketide synthase gene) and the reference (actin gene), four serial dilutions were created from two cDNA libraries. Each of these serial dilutions was assayed in quadruplicate with both the probe/primer set for the target and reference in separate reactions. The standard curves yielded $R^2$ values of 0.996 and 0.998 for the target and reference respectively. The PCR efficiency values calculated by the LIGHTCYCLER® 480 Relative Quantification Software were 1.950 (error 0.0266) and 1.854 (error 0.0181) for the target and reference, respectively. In order to compare the relative level of polyketide synthase mRNA across all five *Aspergillus niger* strains, three dilutions were tested in triplicate for each of the cDNA libraries. The RT-PCR reactions were carried out using both the probe/primer set for the target and reference in separate reactions for each dilution and replicate. These data were compared with the standard curves using the LIGHTCYCLER® 480 Relative Quantification Software according to the manufacturer. Using this method of analysis, the quantity of expression of the treated sample was calculated relative to the untreated control sample. The quantity of the treated sample was determined from the standard curve divided by the quantity of the untreated control sample. Thus, the untreated sample was designated the 1× sample and all other quantities were expressed as an n-fold difference relative to the untreated sample. Then, the treated sample amount was normalized to an endogenous control, actin, to account for differences in the amount of total RNA added to each reaction.

Using Relative Quantification analysis, the relative expression level of *Aspergillus niger* polyketide synthase mRNA was determined to be significantly lower in strains pAmFs031-W1 and pAmFs031-W2 compared to strains *Aspergillus niger* MBin120 pAmFs031-B1, *Aspergillus niger* MBin120 pDM261, or untransformed *Aspergillus niger* MBin120, which correlated with the observed changes in spore coloration. The *Aspergillus niger* MBin120 pAmFs031-W1 and *Aspergillus niger* MBin120 pAmFs031-W2 strains showed a 68% and 82% reduction in polyketide synthase mRNA compared to the "empty vector" control strain. A Southern blot was performed on the same strains, as described in Example 17, to confirm the presence of the entire polyketide synthase gene and eliminate the possibility that the reduction in transcript was due to a disruption of the polyketide synthase gene itself.

Example 17

Detection of the *Aspergillus niger* Polyketide Synthase Gene by Southern Blotting Genomic DNA was extracted from the following *Aspergillus niger* strains (described in Example 16): untransformed *Aspergillus niger* MBin120, *Aspergillus niger* MBin120 pAmFs031-W1, *Aspergillus niger* MBin120 pAmFs031-W2, *Aspergillus niger* MBin120 pAmFs031-B1, and *Aspergillus niger* MBin120 pDM261 using a DNEASY® Plant Maxi Kit. A total of 2 µg of genomic DNA from each strain was digested with Hind III for 17 hours at 37° C. The digested genomic DNA and the DNA molecular weight marker II, DIG-labeled (Roche Applied Science, Indianapolis, Ind., USA) were loaded onto a 0.7% agarose gel in TAE buffer and a current of 22 V was applied for 17 hours. The DNA was transferred from the gel onto a NYTRAN® SuPerCharged membrane for 18 hours using 20×SSC transfer buffer. The DNA was cross-linked to the membrane using ultraviolet irradiation and then equilibrated in DIG Easy Hyb Solution (Roche Applied Science, Indianapolis, Ind., USA) at 42° C. for 30 minutes. The membrane was probed with 20 µl of a DIG-labeled 434 bp PCR product suspended in DIG Easy Hyb solution (Roche Applied Science, Indianapolis, Ind., USA) at 42° C. for 18 hours. The 434 bp DIG-labeled DNA probe was synthesized using a PCR DIG Probe Synthesis Kit (Roche Applied Science, Indianapolis, Ind., USA) and the primers shown below. *Aspergillus niger* polyketide synthase Southern forward primer (062849): 5'-ttaattaatcggtcaatcgccgttgtcaga-3' (SEQ ID NO: 35) *Aspergillus niger* polyketide synthase Southern reverse primer (062850): 5'-aatttccaaacagggtaactccac-3' (SEQ ID NO: 36)

The amplification reaction (50 µl) was composed of 1×PCR Buffer, 5 µl of PCR DIG Probe Synthesis Mix, 50 µM of sense primer, 50 µM of antisense primer, 2.6 units of Expand High Fidelity Polymerase, and 50 ng of *Aspergillus niger* MBin120 genomic DNA (purified as described above). The reaction was incubated in an EPPENDORF® MASTERCYCLER™ 5333 programmed for 30 cycles each for 30 seconds at 94° C., 30 seconds at 55° C., and 30 seconds at 72° C. (7 minute final extension). The probe sequence is complimentary to the promoter (5' untranslated region) of the *Aspergillus niger* polyketide synthase gene, the sequence of which is contained within an 8.8 kb Hind III genomic DNA fragment.

After the membrane was probed, it was washed with 2×SSC plus 0.1% SDS low stringency buffer for 5 minutes at room temperature followed by two high stringency washes with 0.5×SSC plus 0.1% SDS at 65° C. for 15 minutes at room temperature each. The hybridized DIG labeled probe and molecular weight markers were then visualized using a DIG Luminescent Detection Kit (Roche Applied Science, Indianapolis, Ind., USA) following the manufacturer's specifications. The blot was exposed to Biomax XAR film (Sigma Aldrich, St. Louis, Mo., USA) and developed using a Konica SRX-101A film processor (Konica Minolta Medical Imaging USA Inc., Wayne, N.J., USA) to visualize the labeled DNA. The results demonstrated that all of the strains displayed an expected 8.8 kb band indicating that the entire gene was intact in all strains tested.

Example 18

Construction of the *Trichoderma reesei* Transitive RNAi Expression Vector pAL02

A transitive RNAi expression vector was constructed for suppressing the expression of a *Trichoderma reesei* beta-xylosidase gene (SEQ ID NO: 37 for the DNA sequence and SEQ ID NO: 38 for the deduced amino acid sequence).

Figure 8:
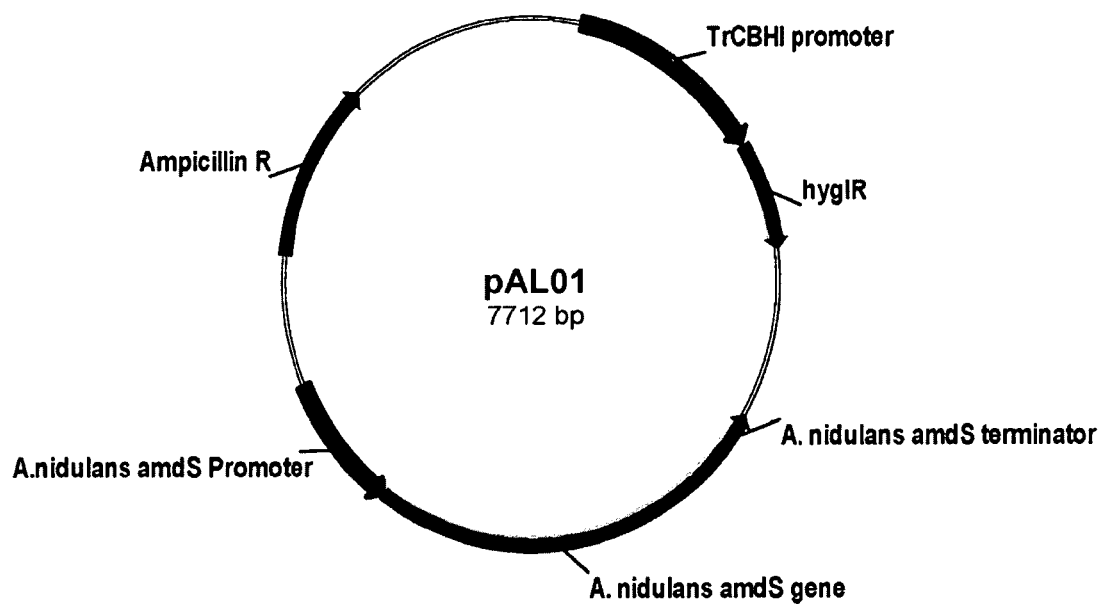
FIG. 8 shows a restriction map of pAL01.

The transitive RNAi plasmid pEvFz-14 was digested with Pac I and Mlu I to isolate the hygromycin inverted repeat. A 527 bp fragment was resolved by 1.0% agarose gel electrophoresis in TAE buffer and then excised from the gel. The fragment was purified using a QIAQUICK® Gel Extraction Kit according to the manufacturer's instructions. The purified fragment was then ligated to Pac I and Mlu I digested pMJ09 (WO 2005/056772) using a Rapid Ligation Kit (Roche Applied Science, Indianapolis, Ind., USA). Two µl of the ligation mixture were used to transform SURE™ chemically competent *E. coli* cells (Stratagene, La Jolla, Calif., USA) according to manufacturer's instructions. Plasmid DNA from several transformants was purified using a BIOROBOT® 9600 and analyzed by digestion with Pac I and Mlu I. The products of the restriction digest were resolved by 1.0% agarose gel electrophoresis in TAE buffer. One transformant was confirmed by DNA sequence analysis to possess the 527 bp hygromycin inverted repeat and was designated pAL01 (FIG. 8).

PCR was employed to amplify a 500 bp fragment comprising a portion of the *Trichoderma reesei* beta-xylosidase coding region (SEQ ID NO: 39 for the DNA sequence and SEQ ID NO: 40 for the deduced amino acid sequence) utilizing genomic DNA from *Trichoderma reesei* RutC30 (WO 2005/056772) serving as template. The genomic DNA from *Trichoderma reesei* RutC30 was isolated using a DNEASY® Plant Maxi Kit according to the manufacturer's instructions. A sense primer was designed to incorporate a Nco I site at the 5'-end and a reverse primer was designed to incorporate a Mlu I site at the 5' end as shown below.

```
Sense primer:
5'-CCATGGTACGAGTTTGGCAGTGGTCT-3'    (SEQ ID NO: 41)

Antisense primer:
5'-ACGCGTTTATGCGTCAGGTGTAGCAT-3'    (SEQ ID NO: 42)
```

The amplification reaction (50 µl) was composed of 10× HERCULASE™ Reaction Buffer (Stratagene, La Jolla, Calif., USA), 0.8 mM dNTPs, 200 ng of *Trichoderma reesei* RutC30 genomic DNA prepared as described in Example 7, 1 ng of primers, and 2.5 units of HERCULASE HOT-START™ Polymerase (Stratagene, La Jolla, Calif., USA).

Figure 9:
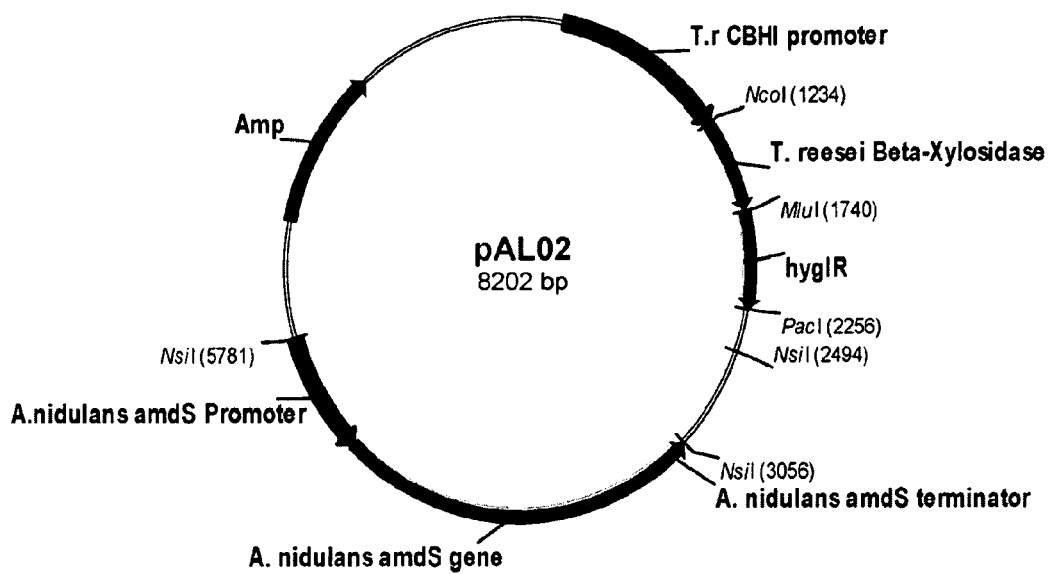
FIG. 9 shows a restriction map of pAL02.

The reactions were incubated in an EPPENDORF® MASTERCYCLER® 5333 programmed for 1 cycle at 92° C. for 2 minutes; 30 cycles each at 92° C. for 30 seconds, 58° C. for 30 seconds, and 68° C. for 1 minute; and a 10 minute final extension. The reaction products were isolated by 1.0% agarose gel electrophoresis in TAE buffer where a 500 bp band was excised from the gel and purified using a QIAQUICK® Gel Extraction Kit according to the manufacturer's instructions. The purified PCR fragment was digested with Nco I and Mlu I and ligated using a Rapid Ligation Kit into pAL01 that had been digested with Nco I and Mlu I. The ligation mixture was used to transform SURE™ chemically competent E. coli cells according to the manufacturer's instructions. Then transformants were screened by colony PCR to identify those containing the desired beta-xylosidase insert. The reactions (20 µl) were composed of 2 µl of 10× THERMOPOL™ Reaction Buffer, 0.4 µl of 10 mM dNTPs, 1 µl of an E. coli transformant colony suspended in 50 µl of deionized water, and 1 pmol of the beta-xylosidase amplification primers. The reactions were incubated in an EPPENDORF® MASTERCYCLER® 5333 programmed for 1 cycle at 94° C. for 2 minutes; 17 cycles each at 94° C. for 30 seconds, 55° C. for 30 seconds, and 72° C. for 30 seconds; and a 5 minute final extension. The amplification products were isolated by 1.0% agarose gel electrophoresis in TAE buffer. Plasmid DNA from several transformants containing the 500 bp beta-xylosidase amplification product was purified using a BIOROBOT® 9600 and analyzed by DNA sequencing. DNA sequence analysis of one plasmid containing the 500 bp beta-xylosidase amplification product confirmed the expected insertion and was designated pAL02 (FIG. 9).

Example 19

Transformation and Determination of Transitive RNAi in *Trichoderma reesei* of the *Trichoderma reesei* Beta-Xylosidase Gene Five µg of pAL02 was used to transform *Trichoderma reesei* SaMe13, a cbh1 deleted strain (WO 2005/030926). *Trichoderma reesei* SaMe13 spores were harvested by pouring 20 ml of 0.01% TWEEN® 80 onto a COVE2 plate of mature *Trichoderma reesei* SaMe13 and spores were scraped off with a petri dish spreader. The spore mixture was drawn up into a 20 ml pipette. Approximately 2-5×10$^7$ spores were inoculated into 100 ml of YP medium supplemented with 2% glucose and 10 mM uridine and incubated at 27° C. at 90 rpm for 16 hours. Mycelia were collected using a 500 ml STERICUP™ filter unit (Millipore, Burlington, Mass., USA) and washed twice with 100 ml of deionized water. The mycelia were then washed twice with 250 ml of 1.2 M sorbitol. The washed mycelia were resuspended in 20 ml of 1.2 M sorbitol, 5 mg of GLUCANEX® per ml and 0.5 mg of chitinase per ml. The mixture was incubated at 34° C. for 15-25 minutes at 90 rpm. The flask was placed on ice for five minutes followed by filtration through MIRACLOTH™. The filter containing the protoplasts was placed into a 50 ml FALCON™ tube (VWR International, West Chester, Pa., USA). The tube was centrifuged at 370×g for 10 minutes in a Sorvall RT6000D centrifuge. The supernatant was discarded and the protoplast pellet was resuspended in 25 ml of 1.2 M sorbitol and centrifuged at 370×g for 10 minutes in a Sorvall RT6000D centrifuge. The supernatant was discarded and pellet resuspended in 25 ml of 1.2 M sorbitol. Ten µl were removed and the tube centrifuged as described above while the protoplasts were counted in a hemocytometer. The supernatant was discarded and the pellet resuspended at a concentration of 1×10$^8$ protoplast per ml of STC.

A transformation mixture consisting of 100 µl of the protoplast suspension, 1-10 µg of plasmid DNA in 10 µl of STC, and 250 µl of polyethylene glycol was gently mixed. The mixture was incubated at room temperature for 30 minutes. Three ml of STC was added, mixed, and poured onto a 150 mm COVE plate. The plates were incubated at 28° C. for 10-14 days.

Twenty transformants, AL02-1-AL02-20, and 4 control transformants containing pAL01 were selected and spores from single colonies were streaked onto COVE plates and incubated for 5 days at 28° C. Spores from these plates were inoculated into 125 ml baffled shake flasks containing 25 ml of Cellulase-Inducing Medium and cultivated at 28° C. and 200 rpm for 5 days. One ml samples of culture broth were removed 5 days post-inoculation, centrifuged at 6,000×g for 10 minutes in an EPPENDORF® centrifuge 5415D, and the supernatants transferred to new EPPENDORF® tubes. Duplicates of the broth samples were used to determine beta-xylosidase activity and beta-glucosidase activity.

The supernatants above were assayed for beta-xylosidase activity using a Coulter Biomek 3000, Biomek NX, and a ORCA robotic arm (Beckman Coulter, Inc, Fullerton, Calif., USA). Culture supernatants were diluted appropriately in 0.1 M succinate, 0.01% Triton X-100 pH 5.0 (sample buffer) followed by a series dilution from 0-fold to ⅓-fold to ⅙-fold of the diluted sample. A total of 20 µl of each dilution was transferred to a 96-well flat bottom. plate. Two hundred micro-liters of a substrate solution containing 1 mg of para-nitrophenyl-beta-D-xylopyranoside per ml of 0.1 M succinate pH 5.0 was added to each well and then incubated at ambient temperature for 45 minutes. Upon completion of the incubation period, 50 µl of 1 M TRIS buffer pH 9 was added to each well to stop the reaction. An endpoint was measured at an optical density of 405 nm for the 96-well plate.

The supernatants above were assayed for beta-glucosidase activity using a Coulter Biomek 3000, Biomek NX, and a ORCA robotic arm. Culture supernatants were diluted appropriately in 0.1 M succinate, 0.01% Triton X-100 pH 5.0 (sample buffer) followed by a series dilution from 0-fold to ⅓-fold to ⅙-fold of the diluted sample. A total of 20 µl of each dilution was transferred to a 96-well flat bottom plate. Two hundred micro-liters of a substrate solution containing 1 mg of para-nitrophenyl-beta-D-glucopyranoside per ml of 0.1 M succinate pH 5.0 was added to each well and then incubated at ambient temperature for 45 minutes. Upon completion of the incubation period, 50 µl of 1 M TRIS buffer pH 9 was added to each well to stop the reaction. An endpoint was measured at an optical density of 405 nm for the 96-well plate. Sample activity was determined by use of the following equation:

$$[(\{OD405/\text{extinction coefficient}\} \times 1 \times 10^6)/\text{incubation time}]/\text{sample volume}$$

where extinction coefficient=17,749, incubation time=45, and sample volume=0.02.

A ratio between the OD obtained from the beta-xylosidase activity assay and the activity determined from the beta-glucosidase assay was calculated and reported as BX/BG. Since beta-glucosidase occurs natively its activity was used as means to normalize for growth differences between transformants. The results are shown in Table 3.

TABLE 3

| Sample | Beta-xylosidase[1] | Beta-glucosidase[2] | Protein[3] | Ratio BX/BG[4] |
|---|---|---|---|---|
| AL02 1 | 5.53 ± 1.10 | 965.63 ± 107.02 | 3.51 ± 0.48 | 0.006 ± 0.001 |
| AL02 2 | 10.13 ± 2.38 | 857.73 ± 40.30 | 4.23 ± 0.51 | 0.012 ± 0.004 |
| AL02 3 | 9.89 ± 1.60 | 1139.06 ± 37.99 | 2.54 ± 0.31 | 0.009 ± 0.002 |
| AL02 4 | 2.94 ± 0.25 | 174.90 ± 45.20 | 1.38 ± 0.25 | 0.017 ± 0.007 |
| AL02 5 | 15.67 ± 2.55 | 919.14 ± 39.01 | 3.56 ± 0.03 | 0.017 ± 0.004 |
| AL02 6 | 15.04 ± 7.12 | 725.61 ± 225.20 | 4.58 ± 1.96 | 0.021 ± 0.004 |
| AL02 7 | 4.78 ± 0.44 | 494.99 ± 69.17 | 3.29 ± 0.17 | 0.010 ± 0.003 |
| AL02 8 | 3.87 ± 0.22 | 507.37 ± 262.44 | 3.25 ± 0.09 | 0.008 ± 0.005 |
| AL02 9 | 9.70 ± 3.52 | 771.72 ± 35.46 | 4.25 ± 0.43 | 0.013 ± 0.005 |
| AL02 10 | 3.25 ± 1.61 | 576.40 ± 202.08 | 2.45 ± 1.04 | 0.006 ± 0.001 |
| AL02 11 | 3.47 ± 2.19 | 667.39 ± 159.68 | 2.21 ± 0.76 | 0.005 ± 0.003 |
| AL02 13 | 7.27 ± 2.44 | 521.00 ± 66.65 | 3.40 ± 0.74 | 0.014 ± 0.004 |
| AL02 14 | 5.75 ± 2.54 | 834.19 ± 414.42 | 4.54 ± 1.58 | 0.007 ± 0.000 |
| AL02 15 | 10.58 ± 0.64 | 625.86 ± 427.59 | 5.51 ± 2.95 | 0.017 ± 0.015 |
| AL02 16 | 1.80 ± 0.60 | 309.91 ± 39.37 | 4.51 ± 1.76 | 0.006 ± 0.002 |
| AL02 17 | 7.31 ± 6.48 | 477.29 ± 370.17 | 6.75 ± 2.44 | 0.015 ± 0.003 |
| AL02 18 | 6.04 ± 3.83 | 556.43 ± 143.08 | 4.69 ± 1.81 | 0.011 ± 0.005 |
| AL02 19 | 1.64 ± 0.42 | 226.67 ± 24.94 | 2.49 ± 0.12 | 0.007 ± 0.001 |
| AL02 20 | 3.55 ± 1.78 | 410.71 ± 261.33 | 3.91 ± 1.97 | 0.009 ± 0.001 |
| AL03 ev | 3.59 ± 0.78 | 320.76 ± 92.52 | 3.60 ± 1.36 | 0.011 ± 0.003 |

[1]Beta-xylosidase activity was measured using para-nitrophenyl-β-D-xylopyranoside as a substrate. Values are expressed as absorbance units ± standard deviation (n = 2 except for sample AL03 ev for which n = 4).
[2]Beta-glucosidase activity was measured using p-nitrophenyl-β-glucopyranoside as a substrate. Values are expressed as μmol substrate hydrolyzed per min per ml of culture broth ± standard deviation (n = 2 except for sample AL03 ev for which n = 4).
[3]Protein concentrations were determined using BCA assay reagents. Values are expressed in mg/ml of culture broth ± standard deviation (n = 2 except for sample AL03 ev for which n = 4).
[4]Ratio of beta-xylosidase and beta-glucosidase activities ± standard deviation (n = 2 except for sample AL03 ev for which n = 4).

Approximately 5/20 transformants appeared to express BX/BG with values from 36% to 55% of the control. These results demonstrate that transitive RNAi can be used to successfully knockdown gene expression in *Trichoderma reesei*.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. A method for reducing or eliminating expression of a target gene encoding a biological substance in an *Aspergillus niger* strain, an *Aspergillus oryzae* strain, or a *Trichoderma reesei* strain, comprising:
   (a) inserting into the genome of the *Aspergillus niger* strain, the *Aspergillus oryzae* strain, or the *Trichoderma reesei* strain a double-stranded transcribable nucleic acid construct comprising a promoter operably linked to a first polynucleotide comprising a first transcribable region with homology to the target gene or a homologue thereof encoding the biological substance and a second polynucleotide comprising a second transcribable region with no effective homology to the target gene or the homologue thereof, wherein the second transcribable region comprises two segments complementary to each other in reverse orientation relative to each other and the first and second transcribable regions are transcribed as a single mRNA molecule; and
   (b) inducing production of short interfering RNAs (siRNAs), comprising sequences of the target gene to be silenced by the process of transitive RNAi, by cultivating the *Aspergillus niger* strain, the *Aspergillus oryzae* strain, or the *Trichoderma reesei* strain under conditions to produce RNA transcripts of the double-stranded transcribable nucleic acid construct that are then converted to the siRNAs, which interact with RNA transcripts of the target gene or the homologue thereof to reduce or eliminate expression of the target gene or the homologue thereof encoding the biological substance.

2. The method of claim 1, wherein the first transcribable region with homology to the target gene comprises at least 19 nucleotides of the target gene.

3. The method of claim 1, wherein the second transcribable region with no effective homology to the target gene comprises at least 19 nucleotides.

4. The method of claim 1, wherein the first and second polynucleotides are separated by an intervening sequence.

5. The method of claim 1, wherein the two segments complementary to each other in reverse orientation are separated by a linking sequence.

6. The method of claim 1, wherein expression of the target gene is reduced by at least 20%.

7. The method of claim 1, wherein the short interfering RNAs interact with RNA transcripts of one or more homologues of the target gene to reduce or eliminate expression of the one or more homologues of the target gene.

8. The method of claim 1, wherein expression of the one or more homologues of the target gene is reduced by at least 20%.

* * * * *

```
                        SEQUENCE LISTING

<160> NUMBER OF SEQ ID NOS: 42

<210> SEQ ID NO 1
<211> LENGTH: 38
<212> TYPE: DNA
<213> ORGANISM: Escherichia coli

<400> SEQUENCE: 1
gcggccgcgc gatgttcggg gattcccaat acgaggtc                            38

<210> SEQ ID NO 2
<211> LENGTH: 36
<212> TYPE: DNA
<213> ORGANISM: Escherichia coli

<400> SEQUENCE: 2 cccgggcat catcgaaatt gccgtcaacc aagctc                               36

<210> SEQ ID NO 3
<211> LENGTH: 38
<212> TYPE: DNA
<213> ORGANISM: Escherichia coli

<400> SEQUENCE: 3
ttaattaagc gatgttcggg gattcccaat acgaggtc                            38
```

<210> SEQ ID NO 4
<211> LENGTH: 36
<212> TYPE: DNA
<213> ORGANISM: Escherichia coli

<400> SEQUENCE: 4

| | | |
|---|---|---|
| cccgggatcg gtccagacgg ccgcgcttct gcgggc | | 36 |

<210> SEQ ID NO 5
<211> LENGTH: 6651
<212> TYPE: DNA
<213> ORGANISM: Aspergillus oryzae

<400> SEQUENCE: 5

| | |
|---|---|
| atggagggc cacgcggcgt ctatctcttc ggagaccaga caagtgattt cgacgccggc | 60 |
| ttacgtcgcc tcctacaagt aaagaataac acaattgttg catcgttctt ccagagatgc | 120 |
| tttcacgctt tgcgccaaga gatcgcgagg cttcaccat ctgaacggaa gatcttcccc | 180 |
| cggtttacga gcatagtgga tctactggcg cgtcaccggg agtcagaccc taatccggct | 240 |
| ctggagagtg cgttgacctg tatctatcaa ttgggatgct ttataaagta cgtgtaactg | 300 |
| cagatcctga cccgtttgaa cgagcctaac ctgagatagc tactacggag accttggaaa | 360 |
| cgtgtaccca tctgcttcag actgccatat agttggcctg tgcgcgggtc ttcttagttc | 420 |
| tgcagctgta agctgttcga caatgttgg agaattgctc cccgctgcgg ttgaagcggt | 480 |
| ggtggtagct ctccgacttg gtctatgcgt ccttaaagtt cgagagctgg tgagctctga | 540 |
| ccaagcgtcg tcaacaagct ggtcagtctt gatttcaggg attagcgaga agatgcctc | 600 |
| gcagcttata ggagaattca ctgctgaacg gtaagtcaa ttgatctgaa atagtttgca | 660 |
| ggacagaatg ttctaaccac tggataaagg caattcctcc ttcatccaaa ccgtatatca | 720 |
| gtgcggtggg atataacagt ataaccatca gcgcaccgcc taaggtcctt gatgatttaa | 780 |
| ttgattctag gctgtctaag agccataagc cggtgagggc gcaaatccat ggtccttacc | 840 |
| atgcagcaca tctgtactat ggccgagatg tcgacaggat catcgaaagc tgccataatg | 900 |
| aggtcgtttc aaactacaca ccccgtatcc ccgtactatc aagtactacg ggacagccga | 960 |
| tagaggccaa acacatgaaa gatctactta aggccgccct tgaagagatt ctactacgtc | 1020 |
| aactatgctg ggagaaagtg accgatgcct gctattccat attaaaaact gctcgtcatc | 1080 |
| aaccatgcaa gttgttccca atttcaagca ctgcgacaca aagcttgttt acagctctta | 1140 |
| cgaaagccgg gataaccgac atcgaagtgg aaaatgggct cggagatgtt cccacgaacc | 1200 |
| cgaaggacaa ccttaacatc agcggcaggg cggactgctc caagatagct atcattggca | 1260 |
| tgtctggacg attcccagaa gctgatggca cagagagttt ctggaccctt ctgtataatg | 1320 |
| gcctcgatgt acaccggaag gtgcctgcag agcgttggga tgttgatgcc cacgttgatc | 1380 |
| ctaccggaac aaaacggaac accagcaagg ttccatacgg atgctggata acgaaccgg | 1440 |
| ggttatttga ccccgcttc ttcaatatgt cgccacgcga agccctccag gcagatcccg | 1500 |
| ctcaaagact tgcattgctc acggcctatg aagctcttga atggccggc tttatccccg | 1560 |
| acagcacccc ttctacacag agggatcgag tcggcctctt ctatggaatg actagcgatg | 1620 |
| actatcggga gataaatagt ggtcaagata ttgatactta ctttatccct ggtgggaatc | 1680 |
| gtgctttcac acctggccgg ataaactact atttcaagtt cagtgggccc agcgtcagcg | 1740 |
| ttgatacagc ttgttcttca agtcttgcgc ctattcatat ggcttgcaat tcgatctgga | 1800 |
| gaaatgattg cgatgctgct attgctggag gtgtcaatat attgacaaac cctgataacc | 1860 |

```
atgccggtct tgaccgtggc catttcctgt ccagaaccgg gaattgcaac acatttgacg   1920
atggtgctga tggctactgt agagcagatg gagtgggtac aatcattctc aagcggctgg   1980
aagacgctca ggcggacaac gatccaatcc tcggtgtgat caatggagcc tataccaatc   2040
attcggcaga agcagtctcg attacccgcc ctcatgttgg cgcacaagcg tttatcttta   2100
ataagctatt gaacgatgcc aatatcgacc ctaaggacgt cagctacgtt gaaatgcatg   2160
gaactggtac tcaagctggg gatgcggtgg aaatgcaatc ggtcttggat acgtttgctc   2220
ccgactaccg ccgtggacca ggacagtctc tccatcttgg ttccgccaaa gcaaatgttg   2280
ggcatggaga gtcagcatct ggtgtaactg cacttgtgaa agtgctgcta atgatgaaga   2340
agaataccat acccccctcat tgtggtataa agactaagat caaccacaac ttccccacgg   2400
atctcgcgca acgaaatgtc cacattgcct tcaacctac cccttggaac agaccggctt   2460
ccggaaagcg gcagtgcttc attaacaact tttcggcggc tggtggaaat accgctcttt   2520
tgatggaaga cgctccaatc gctgaggtta aggggcagga cactcgacct gttcacgttg   2580
tgtctgtatc ggcacgatcc cagagtgcgc tcaaaaacaa catcaactct ctcgtaaaat   2640
acatcgacga acaaggaagg tcattcaatg tgaacgaggc agactttatc ccaagcttgg   2700
catacaccac cacagcacgg cgtatccatc acccattccg tgtcacagct atcgggtcta   2760
gtttgcagga gctgcgtgac tcacttaaca acagctctcg tctggaaagc tttccccctg   2820
tccctgcgac ggcccctggc gtagggttcg tgttcgctgg ccaaggagct cagcacaccg   2880
gaatgggaag gcaactatac gaaaaatgct ctcaattccg ggcaacaatg cagcacttcg   2940
attgcattag tcaaaaccaa gggtttcctt cgatccttcc cttggttgac ggaagcgtgc   3000
ccgtggagga gctgggccct atcgtgacac agctcggcac cacatgtctt cagatggctt   3060
tggtcaacta ttgggttca ctaggtataa aacctgcgtt cgttcttggg catagtctcg   3120
gggagtttgc tgctttgaat accgcaggag tattatcgac ttccgatacc atctaccttt   3180
gtggccgtcg ggctacccctc cttacagaat actgccaggt tggacacac gccatgctgg   3240 ctgtcaaggc ttcctacccc caggtcaagc agttactgaa agaaggtgtg gatgaagttg   3300
cctgtgtcaa ctcacccagt gagacagtcg tcagtggcct caccgctgat attgatgact   3360
tggctcaaag gtgttccact gaaggttgga agtccactaa actaagggta ccgttcgctt   3420
tccattctgc ccaagttact ccaattcttg aacggtttca agaagaggcc cagggtgtca   3480
cgttccgtaa gccgtcgtta ccgtttgttt cctcactcct tggggaagtc atcaccgaat   3540
ctaattacga tgtcctggga gctcaatata tggtgaagca gtgccggaag tcggtgaact   3600
tccttggtgc tcttgaggcc accagatatg cgaaattgat gactgataag actgtctggc   3660
tggaagttgg tgcccatacc atttgctctg tatgatcaa agcaacattc ggtccccagg   3720
ttaccactgt ggcatctctt cgccgagagg agaatgcatg gaaggtcctc tccaatagtc   3780
tatcggccct tcatttggct ggcattgata ttaattggaa agaatatcat caagacttca   3840
gctccagcca ccaggtgctc ccacttcctt cttacaagtg ggatctcaag aactactgga   3900
taccctacac taacaatttc tgccttacga agggtgctcc ccaaactgca attcaagctg   3960
caccacaaac tacattcctg accactgctg cgcaaaaggt tgttgagagt cgcgacgacg   4020
gtacaacagc gactgtcgtg gtgcaaaatg acatcgctga tcctgagttg aaccgtgtta   4080
tccaaggtca caaggtcaat ggagccgcac tttgcccatc ggtaagtatt gcatgcattg   4140
ccagactatc ttgtgtttata attccggctac ttacgtattg cctagtcact ctacgcagat   4200
attgcccaga cacttggaga gtatcttatt gagaaataca aacccgagtt caaagatctt   4260
```

```
ggtctcgatg tgtgtgacat ggtcgtaccg aagccactca tcgcgaaggg aggagagcag    4320
ctctttagag tctctgctat tgctaattgg gctgagaaga aggcttcagt tcaagtatac    4380
gccgttaatg ctgacggcaa aaagaccgtg gatcatgcgt attgtacggt gaagttcttt    4440
gataccaatg cctccgagct cgagtggaag agaatctcgt acctggtcaa gagaagcatc    4500
gacagtcttc accagaatgc ggagacaggg gaggctcacc gtatccagcg aggaatggtc    4560
tataaacttt tcagcgcgtt ggtcgattat gatgaaaatt tcaagtcgat tcgcgaggtt    4620
atcctggaca gcgacaataa tgaggccacc gctcgtgtca aattccaagc accgccagga    4680
aatttccacc gaaacccatt ctggattgac agtttcggtc acttgtccgg attcattatg    4740
aatgcgagcg acgcgaccga ctctaagaac caagtatttg ttaaccatgg atgggattcg    4800
atgcgttgcc tgaagaagtt ctcgcctgat gtcacttatc gcacttatgt gaggatgcag    4860
ccatggcaaa acaacatttg ggctggagat gtttatatct ttgagggcga cgatattatt    4920
gctgtcttcg gaggtgtgaa ggtgggtacc tcactactga ttttggttcc tgcttactga    4980
catgataatt agttccaagc actggcacgc aagatacttg acactgttct tccccctgtt    5040
ggcggttcaa aggcaccaat tacagcgaaa tcaccacctc cagctcgcac tcagaaggcc    5100
aacaccggcg ccaagacccg tcctaaagca cctgttcctt ccaagtcgtt caccaaatct    5160
tctgggccga gtgttgtcgt acgcgcactc agcattctgg cctcagaagt tggcctggca    5220
gagtctgaaa tctcagacga catggtgttt gcggactacg gtgtagactc actcctctcc    5280
cttacagtta ctggcaggta tcgtgaagag ttgaacctcg atttggactc ctctgtgttt    5340
accgatcatc aactgtcaa cgacttcaag cggctcatcg cccaagtgag tccttcagag    5400
agccatgatg gttcctccag tgaacaagag tcgaatttct ctttcaacgg tggcgagtcc    5460
tcaagcgcaa gcacacctga cataacgtca ccgccgaatg agaaggtagc tcaagtcgag    5520
caaaacggca ccatgaagga aatccgtaac atcatggcgg aggagatcgg tgtacccgca    5580
gaagagatcg accctgacga gaacttggga gagatgggta tggactcgct tctctccctt    5640
actgttcttg gaagaatacg ggagactttg gacatggacc tgccaggaga gttcttcatc    5700
gaaaaccaga ccctcaatga tatagaggtg gctttggacc taaaacccaa gactacctct    5760
gctccaattc ctatgccaga gccagtgaaa ttccctgaag ctatccacga cctccagcca    5820
aagcttgctc aacatcccaa ggccacatcc atcctgttac aaggaaaccc caggacagca    5880
acaaagacgt tattcttgtt tcctgacggc tctggctcag ctacatctta cgctaccatc    5940
cccggactct ctcctgacgt ctgcgtttac gggttgaatt gcccatatat gaagacacct    6000
gagaagctca aatgcagcct agatgaactc actgcgccct atgtagcaga gattcgtcgt    6060
cggcaaccca agggtcctta cagcttcggt ggctggtcag caggagggat ctgtgcatat    6120
gatgcggcac gccatctaat gtttgaggaa ggtgaacaag tcgaccgctt gcttctcctt    6180 gatacccct tccccatcgg cctcgagaag ctgccgcaga gattgtacgg cttcttcaac    6240
tctatcggtc tcttcggtga aggtaaaacg gcaccaccct cctggctcct accccacttc    6300
ctagccttta tcgacgctct cgacgcatac aaggccgcgc ccttccatt caaagacgag    6360 aaatgggcca agaaactgcc caagacttat atcatctggg ccaaggacgg tgtttgcggt    6420
aagccgggag atccccggcc tgatcccccg acagacggtt ccaaggatcc caaggagatg    6480
gtctggcttc ttaatgaccg gaccgatctg ggacctaaca agtgggatac attggttgga    6540
cctgagaata ttggtggaat cacagtaatg gaagatgcta atcattttac gatgacgaag    6600
```

```
ggcgaaaaag cgaaagagtt gtctacattt atggctaacg ccatggctta a            6651
```

<210> SEQ ID NO 6
<211> LENGTH: 2141
<212> TYPE: PRT
<213> ORGANISM: Aspergillus oryzae
<400> SEQUENCE: 6

```
Met Glu Gly Pro Arg Gly Val Tyr Leu Phe Gly Asp Gln Thr Ser Asp
1               5                   10                  15

Phe Asp Ala Gly Leu Arg Arg Leu Leu Gln Val Lys Asn Asn Thr Ile
            20                  25                  30

Val Ala Ser Phe Phe Gln Arg Cys Phe His Ala Leu Arg Gln Glu Ile
        35                  40                  45

Ala Arg Leu Ser Pro Ser Glu Arg Lys Ile Phe Pro Arg Phe Thr Ser
    50                  55                  60

Ile Val Asp Leu Leu Ala Arg His Arg Glu Ser Asp Pro Asn Pro Ala
65                  70                  75                  80

Leu Glu Ser Ala Leu Thr Cys Ile Tyr Gln Leu Gly Cys Phe Ile Asn
                85                  90                  95

Tyr Tyr Gly Asp Leu Gly Asn Val Tyr Pro Ser Ala Ser Asp Cys His
            100                 105                 110

Ile Val Gly Leu Cys Ala Gly Leu Leu Ser Ser Ala Ala Val Ser Cys
        115                 120                 125

Ser Asn Asn Val Gly Glu Leu Leu Pro Ala Ala Val Glu Ala Val Val
    130                 135                 140

Val Ala Leu Arg Leu Gly Leu Cys Val Leu Lys Val Arg Glu Leu Val
145                 150                 155                 160

Ser Ser Asp Gln Ala Ser Ser Thr Ser Trp Ser Val Leu Ile Ser Gly
                165                 170                 175

Ile Ser Glu Lys Asp Ala Ser Gln Leu Ile Gly Glu Phe Thr Ala Glu
            180                 185                 190

Arg Ala Ile Pro Pro Ser Ser Lys Pro Tyr Ile Ser Ala Val Gly Tyr
        195                 200                 205

Asn Ser Ile Thr Ile Ser Ala Pro Pro Lys Val Leu Asp Asp Leu Ile
    210                 215                 220

Asp Ser Arg Leu Ser Lys Ser His Lys Pro Val Arg Ala Gln Ile His
225                 230                 235                 240

Gly Pro Tyr His Ala Ala His Leu Tyr Tyr Gly Arg Asp Val Asp Arg
                245                 250                 255

Ile Ile Glu Ser Cys His Asn Glu Val Val Ser Asn Tyr Thr Pro Arg
            260                 265                 270

Ile Pro Val Leu Ser Ser Thr Thr Gly Gln Pro Ile Glu Ala Lys His
        275                 280                 285

Met Lys Asp Leu Leu Lys Ala Ala Leu Glu Glu Ile Leu Leu Arg Gln
    290                 295                 300

Leu Cys Trp Glu Lys Val Thr Asp Ala Cys Tyr Ser Ile Leu Lys Thr
305                 310                 315                 320

Ala Arg His Gln Pro Cys Lys Leu Phe Pro Ile Ser Ser Thr Ala Thr
                325                 330                 335

Gln Ser Leu Phe Thr Ala Leu Thr Lys Ala Gly Ile Thr Asp Ile Glu
            340                 345                 350

Val Glu Asn Gly Leu Gly Asp Val Pro Thr Asn Pro Lys Asp Asn Leu
        355                 360                 365
```

-continued

Asn Ile Ser Gly Arg Ala Asp Cys Ser Lys Ile Ala Ile Ile Gly Met
370                 375                 380

Ser Gly Arg Phe Pro Glu Ala Asp Gly Thr Glu Ser Phe Trp Asp Leu
385                 390                 395                 400

Leu Tyr Asn Gly Leu Asp Val His Arg Lys Val Pro Ala Glu Arg Trp
                405                 410                 415

Asp Val Asp Ala His Val Asp Pro Thr Gly Thr Lys Arg Asn Thr Ser
                420                 425                 430

Lys Val Pro Tyr Gly Cys Trp Ile Asn Glu Pro Gly Leu Phe Asp Pro
                435                 440                 445

Arg Phe Phe Asn Met Ser Pro Arg Glu Ala Leu Gln Ala Asp Pro Ala
450                 455                 460

Gln Arg Leu Ala Leu Leu Thr Ala Tyr Glu Ala Leu Glu Met Ala Gly
465                 470                 475                 480

Phe Ile Pro Asp Ser Thr Pro Ser Thr Gln Arg Asp Arg Val Gly Leu
                485                 490                 495

Phe Tyr Gly Met Thr Ser Asp Asp Tyr Arg Glu Ile Asn Ser Gly Gln
                500                 505                 510

Asp Ile Asp Thr Tyr Phe Ile Pro Gly Gly Asn Arg Ala Phe Thr Pro
                515                 520                 525

Gly Arg Ile Asn Tyr Tyr Phe Lys Phe Ser Gly Pro Ser Val Ser Val
                530                 535                 540

Asp Thr Ala Cys Ser Ser Ser Leu Ala Ala Ile His Met Ala Cys Asn
545                 550                 555                 560

Ser Ile Trp Arg Asn Asp Cys Asp Ala Ala Ile Ala Gly Gly Val Asn
                565                 570                 575

Ile Leu Thr Asn Pro Asp Asn His Ala Gly Leu Asp Arg Gly His Phe
                580                 585                 590

Leu Ser Arg Thr Gly Asn Cys Asn Thr Phe Asp Asp Gly Ala Asp Gly
                595                 600                 605

Tyr Cys Arg Ala Asp Gly Val Gly Thr Ile Ile Leu Lys Arg Leu Glu
                610                 615                 620

Asp Ala Gln Ala Asp Asn Asp Pro Ile Leu Gly Val Ile Asn Gly Ala
625                 630                 635                 640

Tyr Thr Asn His Ser Ala Glu Ala Val Ser Ile Thr Arg Pro His Val
                645                 650                 655

Gly Ala Gln Ala Phe Ile Phe Asn Lys Leu Leu Asn Asp Ala Asn Ile
                660                 665                 670

Asp Pro Lys Asp Val Ser Tyr Val Glu Met His Gly Thr Gly Thr Gln
                675                 680                 685

Ala Gly Asp Ala Val Glu Met Gln Ser Val Leu Asp Thr Phe Ala Pro
                690                 695                 700

Asp Tyr Arg Arg Gly Pro Gly Gln Ser Leu His Leu Gly Ser Ala Lys
705                 710                 715                 720

Ala Asn Val Gly His Gly Glu Ser Ala Ser Gly Val Thr Ala Leu Val
                725                 730                 735

Lys Val Leu Leu Met Met Lys Lys Asn Thr Ile Pro Pro His Cys Gly
                740                 745                 750

Ile Lys Thr Lys Ile Asn His Asn Phe Pro Thr Asp Leu Ala Gln Arg
                755                 760                 765

Asn Val His Ile Ala Phe Gln Pro Thr Pro Trp Asn Arg Pro Ala Ser
770                 775                 780

Gly Lys Arg Gln Cys Phe Ile Asn Asn Phe Ser Ala Ala Gly Gly Asn

-continued

```
            785                 790                 795                 800
        Thr Ala Leu Leu Met Glu Asp Ala Pro Ile Ala Glu Val Lys Gly Gln
                        805                 810                 815

Asp Thr Arg Pro Val His Val Ser Val Ser Ala Arg Ser Gln Ser
                        820                 825                 830

Ala Leu Lys Asn Asn Ile Asn Ser Leu Val Lys Tyr Ile Asp Glu Gln
                        835                 840                 845

Gly Arg Ser Phe Asn Val Asn Glu Ala Asp Phe Ile Pro Ser Leu Ala
                        850                 855                 860

Tyr Thr Thr Thr Ala Arg Arg Ile His His Pro Phe Arg Val Thr Ala
        865                 870                 875                 880

Ile Gly Ser Ser Leu Gln Glu Leu Arg Asp Ser Leu Asn Asn Ser Ser
                        885                 890                 895

Arg Leu Glu Ser Phe Thr Pro Val Pro Ala Thr Ala Pro Gly Val Gly
                        900                 905                 910

Phe Val Phe Ala Gly Gln Gly Ala Gln His Thr Gly Met Gly Arg Gln
                        915                 920                 925

Leu Tyr Glu Lys Cys Ser Gln Phe Arg Ala Thr Met Gln His Phe Asp
                        930                 935                 940

Cys Ile Ser Gln Asn Gln Gly Phe Pro Ser Ile Leu Pro Leu Val Asp
        945                 950                 955                 960

Gly Ser Val Pro Val Glu Glu Leu Gly Pro Ile Val Thr Gln Leu Gly
                        965                 970                 975

Thr Thr Cys Leu Gln Met Ala Leu Val Asn Tyr Trp Gly Ser Leu Gly
                        980                 985                 990

Ile Lys Pro Ala Phe Val Leu Gly His Ser Leu Gly Glu Phe Ala Ala
                        995                 1000                1005

Leu Asn Thr Ala Gly Val Leu Ser Thr Ser Asp Thr Ile Tyr Leu
                        1010                1015                1020

Cys Gly Arg Arg Ala Thr Leu Leu Thr Glu Tyr Cys Gln Val Gly
                        1025                1030                1035

Thr His Ala Met Leu Ala Val Lys Ala Ser Tyr Pro Gln Val Lys
                        1040                1045                1050

Gln Leu Leu Lys Glu Gly Val Asp Glu Val Ala Cys Val Asn Ser
                        1055                1060                1065

Pro Ser Glu Thr Val Val Ser Gly Leu Thr Ala Asp Ile Asp Asp
                        1070                1075                1080

Leu Ala Gln Arg Cys Ser Thr Glu Gly Trp Lys Ser Thr Lys Leu
                        1085                1090                1095

Arg Val Pro Phe Ala Phe His Ser Ala Gln Val Thr Pro Ile Leu
                        1100                1105                1110

Glu Arg Phe Gln Glu Glu Ala Gln Gly Val Thr Phe Arg Lys Pro
                        1115                1120                1125

Ser Leu Pro Phe Val Ser Ser Leu Leu Gly Glu Val Ile Thr Glu
                        1130                1135                1140

Ser Asn Tyr Asp Val Leu Gly Ala Gln Tyr Met Val Lys Gln Cys
                        1145                1150                1155

Arg Lys Ser Val Asn Phe Leu Gly Ala Leu Glu Ala Thr Arg Tyr
                        1160                1165                1170

Ala Lys Leu Met Thr Asp Lys Thr Val Trp Leu Glu Val Gly Ala
                        1175                1180                1185

His Thr Ile Cys Ser Gly Met Ile Lys Ala Thr Phe Gly Pro Gln
                        1190                1195                1200
```

-continued

Val Thr Thr Val Ala Ser Leu Arg Arg Glu Glu Asn Ala Trp Lys
1205                1210                1215

Val Leu Ser Asn Ser Leu Ser Ala Leu His Leu Ala Gly Ile Asp
1220                1225                1230

Ile Asn Trp Lys Glu Tyr His Gln Asp Phe Ser Ser Ser His Gln
1235                1240                1245

Val Leu Pro Leu Pro Ser Tyr Lys Trp Asp Leu Lys Asn Tyr Trp
1250                1255                1260

Ile Pro Tyr Thr Asn Asn Phe Cys Leu Thr Lys Gly Ala Pro Gln
1265                1270                1275

Thr Ala Ile Gln Ala Ala Pro Gln Thr Thr Phe Leu Thr Thr Ala
1280                1285                1290

Ala Gln Lys Val Val Glu Ser Arg Asp Asp Gly Thr Thr Ala Thr
1295                1300                1305

Val Val Val Gln Asn Asp Ile Ala Asp Pro Glu Leu Asn Arg Val
1310                1315                1320

Ile Gln Gly His Lys Val Asn Gly Ala Ala Leu Cys Pro Ser Ser
1325                1330                1335

Leu Tyr Ala Asp Ile Ala Gln Thr Leu Gly Glu Tyr Leu Ile Glu
1340                1345                1350

Lys Tyr Lys Pro Glu Phe Lys Asp Leu Gly Leu Asp Val Cys Asp
1355                1360                1365

Met Val Val Pro Lys Pro Leu Ile Ala Lys Gly Gly Glu Gln Leu
1370                1375                1380

Phe Arg Val Ser Ala Ile Ala Asn Trp Ala Glu Lys Lys Ala Ser
1385                1390                1395

Val Gln Val Tyr Ala Val Asn Ala Asp Gly Lys Lys Thr Val Asp
1400                1405                1410

His Ala Tyr Cys Thr Val Lys Phe Phe Asp Thr Asn Ala Ser Glu
1415                1420                1425

Leu Glu Trp Lys Arg Ile Ser Tyr Leu Val Lys Arg Ser Ile Asp
1430                1435                1440

Ser Leu His Gln Asn Ala Glu Thr Gly Glu Ala His Arg Ile Gln
1445                1450                1455

Arg Gly Met Val Tyr Lys Leu Phe Ser Ala Leu Val Asp Tyr Asp
1460                1465                1470

Glu Asn Phe Lys Ser Ile Arg Glu Val Ile Leu Asp Ser Asp Asn
1475                1480                1485

Asn Glu Ala Thr Ala Arg Val Lys Phe Gln Ala Pro Pro Gly Asn
1490                1495                1500

Phe His Arg Asn Pro Phe Trp Ile Asp Ser Phe Gly His Leu Ser
1505                1510                1515

Gly Phe Ile Met Asn Ala Ser Asp Ala Thr Asp Ser Lys Asn Gln
1520                1525                1530

Val Phe Val Asn His Gly Trp Asp Ser Met Arg Cys Leu Lys Lys
1535                1540                1545

Phe Ser Pro Asp Val Thr Tyr Arg Thr Tyr Val Arg Met Gln Pro
1550                1555                1560

Trp Gln Asn Asn Ile Trp Ala Gly Asp Val Tyr Ile Phe Glu Gly
1565                1570                1575

Asp Asp Ile Ile Ala Val Phe Gly Gly Val Lys Phe Gln Ala Leu
1580                1585                1590

| | | | | | | | | | | | |
|---|---|---|---|---|---|---|---|---|---|---|---|
| Ala | Arg | Lys | Ile | Leu | Asp | Thr | Val | Leu | Pro | Val | Gly Gly Ser |
| 1595 | | | | | 1600 | | | | | 1605 | |
| Lys | Ala | Pro | Ile | Thr | Ala | Lys | Ser | Pro | Pro | Ala | Arg Thr Gln |
| 1610 | | | | | 1615 | | | | | 1620 | |
| Lys | Ala | Asn | Thr | Gly | Ala | Lys | Thr | Arg | Pro | Lys | Ala Pro Val Pro |
| 1625 | | | | | 1630 | | | | | 1635 | |
| Ser | Lys | Ser | Phe | Thr | Lys | Ser | Ser | Gly | Pro | Ser | Val Val Arg |
| 1640 | | | | | 1645 | | | | | 1650 | |
| Ala | Leu | Ser | Ile | Leu | Ala | Ser | Glu | Val | Gly | Leu | Ala Glu Ser Glu |
| 1655 | | | | | 1660 | | | | | 1665 | |
| Ile | Ser | Asp | Asp | Met | Val | Phe | Ala | Asp | Tyr | Gly | Val Asp Ser Leu |
| 1670 | | | | | 1675 | | | | | 1680 | |
| Leu | Ser | Leu | Thr | Val | Thr | Gly | Arg | Tyr | Arg | Glu | Glu Leu Asn Leu |
| 1685 | | | | | 1690 | | | | | 1695 | |
| Asp | Leu | Asp | Ser | Ser | Val | Phe | Thr | Asp | His | Pro | Thr Val Asn Asp |
| 1700 | | | | | 1705 | | | | | 1710 | |
| Phe | Lys | Arg | Leu | Ile | Ala | Gln | Val | Ser | Pro | Ser | Glu Ser His Asp |
| 1715 | | | | | 1720 | | | | | 1725 | |
| Gly | Ser | Ser | Ser | Glu | Gln | Glu | Ser | Asn | Phe | Ser | Phe Asn Gly Gly |
| 1730 | | | | | 1735 | | | | | 1740 | |
| Glu | Ser | Ser | Ser | Ala | Ser | Thr | Pro | Asp | Ile | Thr | Ser Pro Pro Asn |
| 1745 | | | | | 1750 | | | | | 1755 | |
| Glu | Lys | Val | Ala | Gln | Val | Glu | Gln | Asn | Gly | Thr | Met Lys Glu Ile |
| 1760 | | | | | 1765 | | | | | 1770 | |
| Arg | Asn | Ile | Met | Ala | Glu | Glu | Ile | Gly | Val | Pro | Ala Glu Glu Ile |
| 1775 | | | | | 1780 | | | | | 1785 | |
| Asp | Pro | Asp | Glu | Asn | Leu | Gly | Glu | Met | Gly | Met | Asp Ser Leu Leu |
| 1790 | | | | | 1795 | | | | | 1800 | |
| Ser | Leu | Thr | Val | Leu | Gly | Arg | Ile | Arg | Glu | Thr | Leu Asp Met Asp |
| 1805 | | | | | 1810 | | | | | 1815 | |
| Leu | Pro | Gly | Glu | Phe | Phe | Ile | Glu | Asn | Gln | Thr | Leu Asn Asp Ile |
| 1820 | | | | | 1825 | | | | | 1830 | |
| Glu | Val | Ala | Leu | Asp | Leu | Lys | Pro | Lys | Thr | Thr | Ser Ala Pro Ile |
| 1835 | | | | | 1840 | | | | | 1845 | |
| Pro | Met | Pro | Glu | Pro | Val | Lys | Phe | Pro | Glu | Ala | Ile His Asp Leu |
| 1850 | | | | | 1855 | | | | | 1860 | |
| Gln | Pro | Lys | Leu | Ala | Gln | His | Pro | Lys | Ala | Thr | Ser Ile Leu Leu |
| 1865 | | | | | 1870 | | | | | 1875 | |
| Gln | Gly | Asn | Pro | Arg | Thr | Ala | Thr | Lys | Thr | Leu | Phe Leu Phe Pro |
| 1880 | | | | | 1885 | | | | | 1890 | |
| Asp | Gly | Ser | Gly | Ser | Ala | Thr | Ser | Tyr | Ala | Thr | Ile Pro Gly Leu |
| 1895 | | | | | 1900 | | | | | 1905 | |
| Ser | Pro | Asp | Val | Cys | Val | Tyr | Gly | Leu | Asn | Cys | Pro Tyr Met Lys |
| 1910 | | | | | 1915 | | | | | 1920 | |
| Thr | Pro | Glu | Lys | Leu | Lys | Cys | Ser | Leu | Asp | Glu | Leu Thr Ala Pro |
| 1925 | | | | | 1930 | | | | | 1935 | |
| Tyr | Val | Ala | Glu | Ile | Arg | Arg | Arg | Gln | Pro | Lys | Gly Pro Tyr Ser |
| 1940 | | | | | 1945 | | | | | 1950 | |
| Phe | Gly | Gly | Trp | Ser | Ala | Gly | Gly | Ile | Cys | Ala | Tyr Asp Ala Ala |
| 1955 | | | | | 1960 | | | | | 1965 | |
| Arg | His | Leu | Met | Phe | Glu | Glu | Gly | Glu | Gln | Val | Asp Arg Leu Leu |
| 1970 | | | | | 1975 | | | | | 1980 | |
| Leu | Leu | Asp | Thr | Pro | Phe | Pro | Ile | Gly | Leu | Glu | Lys Leu Pro Gln |

```
                1985                1990                1995
Arg Leu Tyr Gly Phe Phe Asn Ser Ile Gly Leu Phe Gly Glu Gly
        2000                2005                2010

Lys Thr Ala Pro Pro Ser Trp Leu Leu Pro His Phe Leu Ala Phe
        2015                2020                2025

Ile Asp Ala Leu Asp Ala Tyr Lys Ala Ala Pro Leu Pro Phe Lys
        2030                2035                2040

Asp Glu Lys Trp Ala Lys Lys Leu Pro Lys Thr Tyr Ile Ile Trp
        2045                2050                2055

Ala Lys Asp Gly Val Cys Gly Lys Pro Gly Asp Pro Arg Pro Asp
        2060                2065                2070

Pro Pro Thr Asp Gly Ser Lys Asp Pro Lys Glu Met Val Trp Leu
        2075                2080                2085

Leu Asn Asp Arg Thr Asp Leu Gly Pro Asn Lys Trp Asp Thr Leu
        2090                2095                2100

Val Gly Pro Glu Asn Ile Gly Gly Ile Thr Val Met Glu Asp Ala
        2105                2110                2115

Asn His Phe Thr Met Thr Lys Gly Glu Lys Ala Lys Glu Leu Ser
        2120                2125                2130

Thr Phe Met Ala Asn Ala Met Ala
        2135                2140

<210> SEQ ID NO 7
<211> LENGTH: 176
<212> TYPE: DNA
<213> ORGANISM: Aspergillus oryzae

<400> SEQUENCE: 7
cagcacttcg attgcattag tcaaaaccaa gggtttcctt cgatccttcc cttggttgac      60
ggaagcgtgc ccgtggagga gctgggccct atcgtgacac agctcggcac cacatgtctt     120
cagatggctt tggtcaacta ttggggttca ctaggtataa aacctgcgtt cgttct         176

<210> SEQ ID NO 8
<211> LENGTH: 59
<212> TYPE: PRT
<213> ORGANISM: Aspergillus oryzae

<400> SEQUENCE: 8

Gln His Phe Asp Cys Ile Ser Gln Asn Gln Gly Phe Pro Ser Ile Leu
1               5                   10                  15

Pro Leu Val Asp Gly Ser Val Pro Val Glu Glu Leu Gly Pro Ile Val
            20                  25                  30

Thr Gln Leu Gly Thr Thr Cys Leu Gln Met Ala Leu Val Asn Tyr Trp
        35                  40                  45

Gly Ser Leu Gly Ile Lys Pro Ala Phe Val Leu
    50                  55

<210> SEQ ID NO 9
<211> LENGTH: 25
<212> TYPE: DNA
<213> ORGANISM: Aspergillus oryzae

<400> SEQUENCE: 9
ccatggagca cttcgattgc attag                                            25

<210> SEQ ID NO 10
<211> LENGTH: 30
```

<212> TYPE: DNA
<213> ORGANISM: Aspergillus oryzae

<400> SEQUENCE: 10
gcggccgcag aacgaacgca ggttttatac                              30

<210> SEQ ID NO 11
<211> LENGTH: 27
<212> TYPE: DNA
<213> ORGANISM: Aspergillus oryzae

<400> SEQUENCE: 11
ccatgggcgc tcaaaaacaa catcaac                                 27

<210> SEQ ID NO 12
<211> LENGTH: 28
<212> TYPE: DNA
<213> ORGANISM: Aspergillus oryzae

<400> SEQUENCE: 12
gcggccgcag aacgaacgca ggttttat                                28

<210> SEQ ID NO 13
<211> LENGTH: 20
<212> TYPE: DNA
<213> ORGANISM: Aspergillus oryzae

<400> SEQUENCE: 13
tactacggag accttggaaa                                         20

<210> SEQ ID NO 14
<211> LENGTH: 20
<212> TYPE: DNA
<213> ORGANISM: Aspergillus oryzae

<400> SEQUENCE: 14
gctcttagac agcctagaat                                         20

<210> SEQ ID NO 15
<211> LENGTH: 20
<212> TYPE: DNA
<213> ORGANISM: Aspergillus oryzae

<400> SEQUENCE: 15
atgcctcgca gcttatagga                                         20

<210> SEQ ID NO 16
<211> LENGTH: 20
<212> TYPE: DNA
<213> ORGANISM: Aspergillus oryzae

<400> SEQUENCE: 16
cgcactgata tacggtttgg                                         20

<210> SEQ ID NO 17
<211> LENGTH: 23
<212> TYPE: DNA
<213> ORGANISM: Aspergillus oryzae

<400> SEQUENCE: 17
ggatctctac ggtaacatcg tca                                     23

<210> SEQ ID NO 18

```
<211> LENGTH: 19
<212> TYPE: DNA
<213> ORGANISM: Aspergillus oryzae

<400> SEQUENCE: 18
gatcggagat gccagggta                                               19

<210> SEQ ID NO 19
<211> LENGTH: 1128
<212> TYPE: DNA
<213> ORGANISM: Aspergillus oryzae

<400> SEQUENCE: 19
atggaagagg aagttgctgc tctcgtcatt gacaatggtt cgggtatgtg caaggccggt    60
ttcgccggtg acgatgctcc ccgtgccgtc ttcccctcca ttgtcggtcg tccccgtcac   120
catggtatca tgattggtat gggtcagaag gactcctacg tcggtgatga ggcacagtcc   180
aagcgtggta tcctcaccct cagataccCC attgagcacg gtgtcgtcac gaactgggat   240
gacatggaga agatctggca ccacaccttc tacaatgaac tccgtgtcgc tcctgaggag   300
caccccgtcc tcttgaccga agcccccatc aaccccaagt ccaaccgtga aagatgacc    360 cagatcgtct tcgagacctt caacgccccc gccttctacg tctccatcca ggccgtcctg   420
tccctgtacg cctccggtcg taccaccggt atcgttctgg actctggtga cggtgtcacc   480
cacgttgtcc ccatctacga gggtttcgcc cttcccacg ccatctcccg tgtcgacatg    540
gctggtcgtg acctgacgga ttacctcatg aagatcctgg ccgagcgtgg ttacactttc   600
tccactaccg ctgagcgtga aattgtccgt gacatcaagg agaagctctg ctacgtcgct   660
ctcgacttcg agcaggagat ccagaccgct tcccagagct ccagcctcga agtcctac     720 gagcttcccg acggtcaggt catcaccatc ggcaacgagc gtttccgtgc tcctgaggct   780
ctgttcgctc ctagcgtcct gggtctggag agcggtggta tccacgagac caccttcaac   840
tccatcatga gtgtgatgt tgatgtccgt aaggatctgt acggcaacat tgtcatgtct    900
ggtggtacta ccatgtaccc cggtatctcc gaccgtatgc agaaggagat cactgctctt   960
gctccttctt ccatgaaggt caagatcatt gctcctcccg agcgcaagta ctccgtctgg  1020
atcggtggtt ccatcctggc ctccctgtcc accttccagc agatgtggat ctccaagcag  1080
gagtacgacg agagcggtcc ctcgatcgtc accgcaagt gcttctaa               1128

<210> SEQ ID NO 20
<211> LENGTH: 375
<212> TYPE: PRT
<213> ORGANISM: Aspergillus oryzae

<400> SEQUENCE: 20

Met Glu Glu Glu Val Ala Ala Leu Val Ile Asp Asn Gly Ser Gly Met
1               5                   10                  15

Cys Lys Ala Gly Phe Ala Gly Asp Asp Ala Pro Arg Ala Val Phe Pro
            20                  25                  30

Ser Ile Val Gly Arg Pro Arg His His Gly Ile Met Ile Gly Met Gly
        35                  40                  45

Gln Lys Asp Ser Tyr Val Gly Asp Glu Ala Gln Ser Lys Arg Gly Ile
    50                  55                  60

Leu Thr Leu Arg Tyr Pro Ile Glu His Gly Val Val Thr Asn Trp Asp
65                  70                  75                  80

Asp Met Glu Lys Ile Trp His His Thr Phe Tyr Asn Glu Leu Arg Val
                85                  90                  95
```

```
Ala Pro Glu Glu His Pro Val Leu Leu Thr Glu Ala Pro Ile Asn Pro
            100                 105                 110

Lys Ser Asn Arg Glu Lys Met Thr Gln Ile Val Phe Glu Thr Phe Asn
        115                 120                 125

Ala Pro Ala Phe Tyr Val Ser Ile Gln Ala Val Leu Ser Leu Tyr Ala
    130                 135                 140

Ser Gly Arg Thr Thr Gly Ile Val Leu Asp Ser Gly Asp Gly Val Thr
145                 150                 155                 160

His Val Val Pro Ile Tyr Glu Gly Phe Ala Leu Pro His Ala Ile Ser
                165                 170                 175

Arg Val Asp Met Ala Gly Arg Asp Leu Thr Asp Tyr Leu Met Lys Ile
            180                 185                 190

Leu Ala Glu Arg Gly Tyr Thr Phe Ser Thr Thr Ala Glu Arg Glu Ile
        195                 200                 205

Val Arg Asp Ile Lys Glu Lys Leu Cys Tyr Val Ala Leu Asp Phe Glu
    210                 215                 220

Gln Glu Ile Gln Thr Ala Ser Gln Ser Ser Leu Glu Lys Ser Tyr
225                 230                 235                 240

Glu Leu Pro Asp Gly Gln Val Ile Thr Ile Gly Asn Glu Arg Phe Arg
                245                 250                 255

Ala Pro Glu Ala Leu Phe Ala Pro Ser Val Leu Gly Leu Glu Ser Gly
            260                 265                 270

Gly Ile His Glu Thr Thr Phe Asn Ser Ile Met Lys Cys Asp Val Asp
        275                 280                 285

Val Arg Lys Asp Leu Tyr Gly Asn Ile Val Met Ser Gly Gly Thr Thr
    290                 295                 300

Met Tyr Pro Gly Ile Ser Asp Arg Met Gln Lys Glu Ile Thr Ala Leu
305                 310                 315                 320

Ala Pro Ser Ser Met Lys Val Lys Ile Ile Ala Pro Pro Glu Arg Lys
                325                 330                 335

Tyr Ser Val Trp Ile Gly Gly Ser Ile Leu Ala Ser Leu Ser Thr Phe
            340                 345                 350

Gln Gln Met Trp Ile Ser Lys Gln Glu Tyr Asp Glu Ser Gly Pro Ser
        355                 360                 365

Ile Val His Arg Lys Cys Phe
    370                 375

<210> SEQ ID NO 21
<211> LENGTH: 20
<212> TYPE: DNA
<213> ORGANISM: Aspergillus oryzae

<400> SEQUENCE: 21
atgcctcgca gcttatagga                                                 20

<210> SEQ ID NO 22
<211> LENGTH: 20
<212> TYPE: DNA
<213> ORGANISM: Aspergillus oryzae

<400> SEQUENCE: 22
cgcactgata tacggtttgg                                                 20

<210> SEQ ID NO 23
<211> LENGTH: 23
<212> TYPE: DNA
```

<213> ORGANISM: Aspergillus oryzae

<400> SEQUENCE: 23
ggatctctac ggtaacatcg tca                                          23

<210> SEQ ID NO 24
<211> LENGTH: 19
<212> TYPE: DNA
<213> ORGANISM: Aspergillus oryzae

<400> SEQUENCE: 24
gatcggagat gccagggta                                               19

<210> SEQ ID NO 25
<211> LENGTH: 6387
<212> TYPE: DNA
<213> ORGANISM: Aspergillus niger

<400> SEQUENCE: 25

| | | | | | |
|---|---|---|---|---|---|
| atggagggtc | catctcgtgt | gtacctttt | ggagaccaga | ccagcgacat | cgaagctggc | 60 |
| ctgcgccgtc | tgctccaagc | gaagaatagt | accattgtcc | agtccttttt | ccagcaatgc | 120 |
| ttccatgcaa | ttcgtcaaga | gatcgcgaag | ctcccgccgt | ctcatcggaa | gctcttccca | 180 |
| cgcttcacga | gcatcgttga | tctcctttcc | aggagtcgtg | aatcaggtcc | tagccctgtc | 240 |
| ctggagagtg | cattgacatg | catctaccaa | ttgggttgtt | tcattcactt | ttacggggat | 300 |
| cttggacatg | actaccctac | accctccaac | agccatcttg | ttggcctgtg | cactggtgtt | 360 |
| ctgagctgca | cggctgtaag | ttgcgccaga | aatgttggag | agcttattcc | agctgcagtg | 420 |
| gaatcggttg | taattgcact | gcgactggga | atctgcgttt | tcgagttcg | agaactggtg | 480 |
| gactccgccg | attccgagtc | aacatgctgg | tcagcgttgg | tttctggaat | cagtgaagca | 540 |
| gaggctagcc | acctgatcga | cgagtacagt | agtaagaagg | ctactccgcc | ttcttcgaaa | 600 |
| ccgtatatca | gcgcggtaag | ctctaatggc | gttactgtca | gcgcaccacc | tacggtactt | 660 |
| gatgaattcg | tcgagacctg | catttccaag | aattacaagc | cagtgaaggc | ccctattcat | 720 |
| ggcccgtacc | atgcgccaca | tctgtatgat | gataaggata | tcgaccgcat | cctgcagcag | 780 |
| tcctctgctc | tagaaggact | gaccggctgt | tcacccgtta | ttcccatcat | ctccagtaac | 840 |
| actgaaagc | cgatcaaggc | caagtccatc | aaagatctct | tcaaggtcgc | actggaggag | 900 |
| atactcctac | gacgactatg | ctgggacaag | gtcacggagt | cctgcacatc | agtctgcaag | 960 |
| accggcacaa | accactcttg | caaattgttt | ccgatctcga | gtagcgccac | tcaaagtttg | 1020 |
| ttcacagtcc | tcaagaaggc | cggtgtgagc | atcagcttgg | agactggggt | aggagagatc | 1080 |
| gcgacgaacc | cagaaatgcg | gaaccttact | ggcaaggcag | aaaattcaaa | gattgctatc | 1140 |
| attggtatgt | ctggaagatt | tcctgactcg | gatggtacgg | agagcttctg | gaacctcctg | 1200 |
| tacaaaggac | tcgacgtaca | tcgcaaagtc | cccgcagacc | gttgggacgt | tgatgcccac | 1260 |
| gtcgacatga | ccgggtcaaa | gagaaacaca | agcaaagtgg | cttacggttg | ctggatcaac | 1320 |
| gaacccggcc | tgtttgaccc | ccgattcttc | aacatgtcgc | ctcgggaagc | actccaagca | 1380 |
| gatcctgcac | aacgtcttgc | gttgcttaca | gcgtacgagg | ctctcgagat | ggctggcttc | 1440 |
| atcccggata | gctctccatc | gacgcagagg | gaccgtgtgg | gtattttcta | cggaatgacc | 1500 |
| agtgacgact | accgtgagat | caacagcggc | caggacattg | atacctattt | catccctggc | 1560 |
| ggtaaccgag | catttacgcc | gggtcggata | aactactact | tcaaatttag | cggccccagt | 1620 |
| gtgagcgttg | acacagcgtg | ctcgtctagt | cttgctgcta | tccacatggc | ttgcaattcg | 1680 |

```
atctggagaa atgactgcga tgccgccatc actggaggtg tgaacattct gaccaaccct    1740
gacaaccacg ccggtctgga tcggggccat ttcctgtcca ccactggcaa ctgtaacacc    1800
tttgatgacg gcgccgacgg ctactgtaga gcggacggag ttggaagcat cgttttgaag    1860
cggcttgaag atgccgaggc cgacaacgac ccgatcctgg ccgtcatcaa cggtgcttac    1920
accaaccact cggcggaggc cgtgtcaatc actcgtcccc atgttggcgc gcaagcattc    1980
atcttcaaca agctgctcaa tgatgcgaat atcgaccta aggacgtgag ctacgtggaa    2040
atgcatggca ctggaactca agcaggtgat gcagtcgaaa tgcagtccgt tcttgacgtc    2100
ttcgcaccag actaccgccg gggtcccggt caatcgcttc atatcggttc tgccaaggca    2160
aacattggac acgtgaatc cgcatcagga gtgactgctc ttgtcaaggt cctcctaatg    2220
atgagagaga acatgattcc tcctcattgt ggtatcaaga ccaagatcaa ttccaatttc    2280
ccgacagact tggcgaagcg caatgttcat atcgccttcc aacccactcc ctggaatcgg    2340
ccagcttcag gaaagcggcg aactttcgtc aacaactttt ctgctgctgg tggtaacact    2400
gctcttctac tggaagatgc tcccataccg gaacgccaag ggcaggaccc caggtcgttc    2460
catttggtct ccgtgtcagc aagatcccag tctgcattga agaacaacgt cgaagctctg    2520
gtgaagtaca ttgactctca gggcaagtcc tttggtgtga agagactga attccttcca    2580 aacctggcgt acacgaccac cgcacgccgt atccaccatc ccttccgtgt cactgcggtt    2640
ggagcgaacc tacaatcact gcgtgactcg ctgcatggtg ctttgcaccg tgagacatat    2700
accccagttc cctcaacggc tcctggtatt ggtttcgtct tcaccggcca aggagcccaa    2760
tactccggaa tgggcaagga actctaccgc agttgtttcc aattccgaac caccattgag    2820
cattttgact gcatcgcaag aagccagggc cttccttcta tccttcctct tgtcgatgga    2880
agcgtggctg tcgaagaact tagccctgtc gtggtacaag tgggaactac ctgtgtacaa    2940
atggctctag taaattactg gactgctctg ggtgtgaagc cggcctttat catcggacac    3000
agtcttggag actatgcagc ccttaacacg gccggtgttc tatccaccag cgatacaatc    3060
tatctttgtg gccggcgtgc tcagttgctg acgaaggaat gcaagattgg gacacattcg    3120
atgctggcca tcaaggcgtc cctggcagag gtcaaacatt tcctcagaga cgagctccac    3180
gaagtctctt gtgttaacgc acctgcggag accgtcgtca gcggccttgt cgctgatatc    3240
gacgagttgg ctcagaaatg ctccacagag ggtttgaagt caaccaagct caaggttcct    3300
tacgcgttcc attcctctca ggttgatcct atcttggagg ccttcgaaga tattgcccaa    3360
ggtgtcacct ccacaagcc gacaacacct ttcgtctcag ccctgttcgg ggaagtgatc    3420
accgatgcta actgggagtg tctcggcccc aagtacctgc gcgatcattg cagaaagacg    3480
gtcaacttcc ttggcggcgt ggaggctacg aggcatgcga agctgaccaa tgacaagact    3540
ctgtgggttg agatcggctc acataccatt tgctctggaa tgatcaaagc aactcttgga    3600
ccgcaagtta caacggttgc atctctacgc gcgaagaag atacctggaa ggtccttccg    3660
aacagtcttg cgagccttca tctggcgggt attgatatca actggaagca atatcaccag    3720
gactttagct cctctctcca ggtcctccgc ctcccagcct acaagtggga tctcaagaac    3780
tactggattc cctataccaa caacttctgc ctgagcaagg gcgctccagt tgcgacagta    3840
gcggcagggc cacagcatga gtacctgaca accgcggctc agaaggtcat tgagactcga    3900
agtgatggag caacagctac agtcgtgata gagaacgaca ttgctgatcc cgagctcaac    3960
cgcgtcattc aaggccataa ggtcaacggt actgctttgt gtccctcatc actatatgcc    4020
```

```
gacatctctc aaacgcttgc agagtatctc atcaaaaagt acaagcctga gtacgacgga    4080
cttggactgg atgtgtgtga ggtcacagtg ccacgaccac tgattgcgaa aggcggacag    4140
cagctcttta gagtatctgc gacagcggat tgggcggaga agaagacaac ccttcagata    4200
tattcagtca ctgcggaggg gaagaagacg gctgaccacg caacttgcac tgtccgattc    4260
tttgactgcg ctgctgcgga ggcggaatgg aaacgagttt cctaccttgt caagaggagc    4320
attgaccgac tgcatgatat cgccgaaaat ggtgacgctc accgtcttgg tagaggcatg    4380
gtttacaaac tcttcgctgc cttggttgat tatgacgaca acttcaagtc cattcgcgag    4440
gttattcttg acagtgaaca gcacgaagcg actgcacgcg tcaagttcca agcaccacaa    4500
ggcaatttcc accgaaaccc gttctggatt gacagttttg gacacctgtc tgggttcatc    4560
atgaacgcaa gcgatgcaac cgactccaag aaccaggtct ttgtcaatca cggatgggac    4620
tccatgcgtt gtttgaagaa gttctcgcct gatgtcacct acaggactta tgttagaatg    4680
cagccttgga aagactccat ctgggctggt gatgtctacg ttttcgatgg ggatgatatc    4740
gttgcggtgt atggtgcagt caagttccaa gccttatcac gcaagattct cgatacggtc    4800
ctacctccaa gtcgtgctag cgccccggcc ccggcgaagc ctgctgctaa gcccagcgcc    4860
ccaagcttgg tcaaacgggc acttaccatc ctcgcagagg aagtgggtct gtctgaatcc    4920
gagattacgg atgatctggt cttcgcagac tacggtgtgg actcccttct ttcgttgacg    4980
gtcacgggca ggtatcgtga agagctggat atcgatctcg aatcctccat cttcatcgac    5040
cagccgaccg tgaaagactt caagcagttc ttggccccaa tgagccaggg agaagccagc    5100
gatgggtcca ccagtgaccc agagtctagt agctccttca atggtggctc ttcaacagac    5160
gagtccagtg ctgggtcccc tgtcagctca ccaccaaatg agaaggttac gcaggtcgag    5220
cagcatgcta cgataaagga gattcgcgcc attttggccg atgagattgg tgttacggag    5280
gaggagctga aggacgatga aacttgggga gagatgggga tggactctct gctttcgctt    5340
acggtgcttg gtaggatccg tgagacattg gatctggatc taccgggcga gttcttcatc    5400
gagaatcaaa ctctgaatga cgtggaggat gcattgggcc tcaaacccaa ggcagctcct    5460
gcgcctgcgc ctgcgcctgc tcccgtaccc gcacccgtgt ccgcgcccat attgaaggag    5520
cctgtcccca acgcaaactc taccatcatg gcccgggcga gcccgcaccc tcgatcaacc    5580
tccattctgt tgcaaggaaa cccgaaaaac gcgaccaaga ccctgttcct gttccctgat    5640
gggtctggct ccgcaacatc gtatgcaacc attcccggag tgtccccgga cgtgtgtgtc    5700
tacggattga actgcccgta catgaagact ccagagaagc tcaagtatcc ccttgctgag    5760
atgacattcc cctatctggc cgagatccgc cgcagacagc ccaagggccc gtacaacttc    5820
ggtggatggt ctgcaggtgg tatttgcgcc tatgatgccg ctcgctacct aatccttgaa    5880
gagggcgaac aggttgaccg attgcttctt cttgactcgc ccttccccat ggcttagag     5940
aagttgccca ctcggctgta cggcttcatc aactcaatgg gtctctttgg tgaaggcaac    6000
aaggctcccc cggcctggtt gctccctcat ttcctggcct tcattgattc cctcgatacc    6060
tacaaggccg tccccctccc ctttgacgat ccgaagtggg ccaagaagat gcccaagaca    6120
ttcatggtct gggccaagga cggtatctgc agcaagccgg atgacccgtg gcccgagccg    6180
gacccggacg gcaagccgga cacgagagag atggtctggc tcctcaagaa ccggaccgac    6240
atgggaccca acaagtggga cacactcgtc gggcccaaa  acgtcggtgg aatcactgtg    6300
atagagggtg cgaatcattt caccatgact ttgggaccca aggctaaaga attgggctcg    6360
ttcattggca acgccatggc caattaa                                        6387
```

<210> SEQ ID NO 26
<211> LENGTH: 2128
<212> TYPE: PRT
<213> ORGANISM: Aspergillus niger

<400> SEQUENCE: 26

```
Met Glu Gly Pro Ser Arg Val Tyr Leu Phe Gly Asp Gln Thr Ser Asp
1               5                   10                  15

Ile Glu Ala Gly Leu Arg Arg Leu Leu Gln Ala Lys Asn Ser Thr Ile
            20                  25                  30

Val Gln Ser Phe Phe Gln Gln Cys Phe His Ala Ile Arg Gln Glu Ile
        35                  40                  45

Ala Lys Leu Pro Pro Ser His Arg Lys Leu Phe Pro Arg Phe Thr Ser
    50                  55                  60

Ile Val Asp Leu Leu Ser Arg Ser Arg Glu Ser Gly Pro Ser Pro Val
65                  70                  75                  80

Leu Glu Ser Ala Leu Thr Cys Ile Tyr Gln Leu Gly Cys Phe Ile His
                85                  90                  95

Phe Tyr Gly Asp Leu Gly His Asp Tyr Pro Thr Pro Ser Asn Ser His
            100                 105                 110

Leu Val Gly Leu Cys Thr Gly Val Leu Ser Cys Thr Ala Val Ser Cys
        115                 120                 125

Ala Arg Asn Val Gly Glu Leu Ile Pro Ala Ala Val Glu Ser Val Val
    130                 135                 140

Ile Ala Leu Arg Leu Gly Ile Cys Val Phe Arg Val Arg Glu Leu Val
145                 150                 155                 160

Asp Ser Ala Asp Ser Glu Ser Thr Cys Trp Ser Ala Leu Val Ser Gly
                165                 170                 175

Ile Ser Glu Ala Glu Ala Ser His Leu Ile Asp Glu Tyr Ser Ser Lys
            180                 185                 190

Lys Ala Thr Pro Pro Ser Ser Lys Pro Tyr Ile Ser Ala Val Ser Ser
        195                 200                 205

Asn Gly Val Thr Val Ser Ala Pro Pro Thr Val Leu Asp Glu Phe Val
    210                 215                 220

Glu Thr Cys Ile Ser Lys Asn Tyr Lys Pro Val Lys Ala Pro Ile His
225                 230                 235                 240

Gly Pro Tyr His Ala Pro His Leu Tyr Asp Asp Lys Asp Ile Asp Arg
                245                 250                 255

Ile Leu Gln Gln Ser Ser Ala Leu Glu Gly Leu Thr Gly Cys Ser Pro
            260                 265                 270

Val Ile Pro Ile Ile Ser Ser Asn Thr Gly Lys Pro Ile Lys Ala Lys
        275                 280                 285

Ser Ile Lys Asp Leu Phe Lys Val Ala Leu Glu Glu Ile Leu Leu Arg
    290                 295                 300

Arg Leu Cys Trp Asp Lys Val Thr Glu Ser Cys Thr Ser Val Cys Lys
305                 310                 315                 320

Thr Gly Thr Asn His Ser Cys Lys Leu Phe Pro Ile Ser Ser Ser Ala
                325                 330                 335

Thr Gln Ser Leu Phe Thr Val Leu Lys Lys Ala Gly Val Ser Ile Ser
            340                 345                 350

Leu Glu Thr Gly Val Gly Glu Ile Ala Thr Asn Pro Glu Met Arg Asn
        355                 360                 365

Leu Thr Gly Lys Ala Glu Asn Ser Lys Ile Ala Ile Ile Gly Met Ser
```

```
            370                 375                 380
Gly Arg Phe Pro Asp Ser Asp Gly Thr Glu Ser Phe Trp Asn Leu Leu
385                 390                 395                 400

Tyr Lys Gly Leu Asp Val His Arg Lys Val Pro Ala Asp Arg Trp Asp
                405                 410                 415

Val Asp Ala His Val Asp Met Thr Gly Ser Lys Arg Asn Thr Ser Lys
                420                 425                 430

Val Ala Tyr Gly Cys Trp Ile Asn Glu Pro Gly Leu Phe Asp Pro Arg
            435                 440                 445

Phe Phe Asn Met Ser Pro Arg Glu Ala Leu Gln Ala Asp Pro Ala Gln
450                 455                 460

Arg Leu Ala Leu Leu Thr Ala Tyr Glu Ala Leu Glu Met Ala Gly Phe
465                 470                 475                 480

Ile Pro Asp Ser Ser Pro Ser Thr Gln Arg Asp Arg Val Gly Ile Phe
                485                 490                 495

Tyr Gly Met Thr Ser Asp Asp Tyr Arg Glu Ile Asn Ser Gly Gln Asp
                500                 505                 510

Ile Asp Thr Tyr Phe Ile Pro Gly Gly Asn Arg Ala Phe Thr Pro Gly
            515                 520                 525

Arg Ile Asn Tyr Tyr Phe Lys Phe Ser Gly Pro Ser Val Ser Val Asp
530                 535                 540

Thr Ala Cys Ser Ser Leu Ala Ala Ile His Met Ala Cys Asn Ser
545                 550                 555                 560

Ile Trp Arg Asn Asp Cys Asp Ala Ala Ile Thr Gly Gly Val Asn Ile
                565                 570                 575

Leu Thr Asn Pro Asp Asn His Ala Gly Leu Asp Arg Gly His Phe Leu
                580                 585                 590

Ser Thr Thr Gly Asn Cys Asn Thr Phe Asp Asp Gly Ala Asp Gly Tyr
            595                 600                 605

Cys Arg Ala Asp Gly Val Gly Ser Ile Val Leu Lys Arg Leu Glu Asp
610                 615                 620

Ala Glu Ala Asp Asn Asp Pro Ile Leu Ala Val Ile Asn Gly Ala Tyr
625                 630                 635                 640

Thr Asn His Ser Ala Glu Ala Val Ser Ile Thr Arg Pro His Val Gly
                645                 650                 655

Ala Gln Ala Phe Ile Phe Asn Lys Leu Leu Asn Asp Ala Asn Ile Asp
                660                 665                 670

Pro Lys Asp Val Ser Tyr Val Glu Met His Gly Thr Gly Thr Gln Ala
            675                 680                 685

Gly Asp Ala Val Glu Met Gln Ser Val Leu Asp Val Phe Ala Pro Asp
690                 695                 700

Tyr Arg Arg Gly Pro Gly Gln Ser Leu His Ile Gly Ser Ala Lys Ala
705                 710                 715                 720

Asn Ile Gly His Gly Glu Ser Ala Ser Gly Val Thr Ala Leu Val Lys
                725                 730                 735

Val Leu Leu Met Met Arg Glu Asn Met Ile Pro Pro His Cys Gly Ile
                740                 745                 750

Lys Thr Lys Ile Asn Ser Asn Phe Pro Thr Asp Leu Ala Lys Arg Asn
            755                 760                 765

Val His Ile Ala Phe Gln Pro Thr Pro Trp Asn Arg Pro Ala Ser Gly
770                 775                 780

Lys Arg Arg Thr Phe Val Asn Asn Phe Ser Ala Ala Gly Gly Asn Thr
785                 790                 795                 800
```

```
Ala Leu Leu Leu Glu Asp Ala Pro Ile Pro Glu Arg Gln Gly Gln Asp
                805                 810                 815

Pro Arg Ser Phe His Leu Val Ser Val Ser Ala Arg Ser Gln Ser Ala
            820                 825                 830

Leu Lys Asn Asn Val Glu Ala Leu Val Lys Tyr Ile Asp Ser Gln Gly
        835                 840                 845

Lys Ser Phe Gly Val Lys Glu Thr Glu Phe Leu Pro Asn Leu Ala Tyr
    850                 855                 860

Thr Thr Thr Ala Arg Arg Ile His His Pro Phe Arg Val Thr Ala Val
865                 870                 875                 880

Gly Ala Asn Leu Gln Ser Leu Arg Asp Ser Leu His Gly Ala Leu His
                885                 890                 895

Arg Glu Thr Tyr Thr Pro Val Pro Ser Thr Ala Pro Gly Ile Gly Phe
            900                 905                 910

Val Phe Thr Gly Gln Gly Ala Gln Tyr Ser Gly Met Gly Lys Glu Leu
        915                 920                 925

Tyr Arg Ser Cys Phe Gln Phe Arg Thr Thr Ile Glu His Phe Asp Cys
    930                 935                 940

Ile Ala Arg Ser Gln Gly Leu Pro Ser Ile Leu Pro Leu Val Asp Gly
945                 950                 955                 960

Ser Val Ala Val Glu Glu Leu Ser Pro Val Val Gln Val Gly Thr
                965                 970                 975

Thr Cys Val Gln Met Ala Leu Val Asn Tyr Trp Thr Ala Leu Gly Val
            980                 985                 990

Lys Pro Ala Phe Ile Ile Gly His Ser Leu Gly Asp Tyr Ala Ala Leu
        995                 1000                1005

Asn Thr Ala Gly Val Leu Ser Thr Ser Asp Thr Ile Tyr Leu Cys
    1010                1015                1020

Gly Arg Arg Ala Gln Leu Leu Thr Lys Glu Cys Lys Ile Gly Thr
    1025                1030                1035

His Ser Met Leu Ala Ile Lys Ala Ser Leu Ala Glu Val Lys His
    1040                1045                1050

Phe Leu Arg Asp Glu Leu His Glu Val Ser Cys Val Asn Ala Pro
    1055                1060                1065

Ala Glu Thr Val Val Ser Gly Leu Val Ala Asp Ile Asp Glu Leu
    1070                1075                1080

Ala Gln Lys Cys Ser Thr Glu Gly Leu Lys Ser Thr Lys Leu Lys
    1085                1090                1095

Val Pro Tyr Ala Phe His Ser Ser Gln Val Asp Pro Ile Leu Glu
    1100                1105                1110

Ala Phe Glu Asp Ile Ala Gln Gly Val Thr Phe His Lys Pro Thr
    1115                1120                1125

Thr Pro Phe Val Ser Ala Leu Phe Gly Glu Val Ile Thr Asp Ala
    1130                1135                1140

Asn Trp Glu Cys Leu Gly Pro Lys Tyr Leu Arg Asp His Cys Arg
    1145                1150                1155

Lys Thr Val Asn Phe Leu Gly Gly Val Glu Ala Thr Arg His Ala
    1160                1165                1170

Lys Leu Thr Asn Asp Lys Thr Leu Trp Val Glu Ile Gly Ser His
    1175                1180                1185

Thr Ile Cys Ser Gly Met Ile Lys Ala Thr Leu Gly Pro Gln Val
    1190                1195                1200
```

```
Thr Thr Val Ala Ser Leu Arg Arg Glu Glu Asp Thr Trp Lys Val
1205                1210                1215

Leu Ser Asn Ser Leu Ala Ser Leu His Leu Ala Gly Ile Asp Ile
1220                1225                1230

Asn Trp Lys Gln Tyr His Gln Asp Phe Ser Ser Ser Leu Gln Val
1235                1240                1245

Leu Arg Leu Pro Ala Tyr Lys Trp Asp Leu Lys Asn Tyr Trp Ile
1250                1255                1260

Pro Tyr Thr Asn Asn Phe Cys Leu Ser Lys Gly Ala Pro Val Ala
1265                1270                1275

Thr Val Ala Ala Gly Pro Gln His Glu Tyr Leu Thr Thr Ala Ala
1280                1285                1290

Gln Lys Val Ile Glu Thr Arg Ser Asp Gly Ala Thr Ala Thr Val
1295                1300                1305

Val Ile Glu Asn Asp Ile Ala Asp Pro Glu Leu Asn Arg Val Ile
1310                1315                1320

Gln Gly His Lys Val Asn Gly Thr Ala Leu Cys Pro Ser Ser Leu
1325                1330                1335

Tyr Ala Asp Ile Ser Gln Thr Leu Ala Glu Tyr Leu Ile Lys Lys
1340                1345                1350

Tyr Lys Pro Glu Tyr Asp Gly Leu Gly Leu Asp Val Cys Glu Val
1355                1360                1365

Thr Val Pro Arg Pro Leu Ile Ala Lys Gly Gly Gln Gln Leu Phe
1370                1375                1380

Arg Val Ser Ala Thr Ala Asp Trp Ala Glu Lys Lys Thr Thr Leu
1385                1390                1395

Gln Ile Tyr Ser Val Thr Ala Glu Gly Lys Lys Thr Ala Asp His
1400                1405                1410

Ala Thr Cys Thr Val Arg Phe Phe Asp Cys Ala Ala Ala Glu Ala
1415                1420                1425

Glu Trp Lys Arg Val Ser Tyr Leu Val Lys Arg Ser Ile Asp Arg
1430                1435                1440

Leu His Asp Ile Ala Glu Asn Gly Asp Ala His Arg Leu Gly Arg
1445                1450                1455

Gly Met Val Tyr Lys Leu Phe Ala Ala Leu Val Asp Tyr Asp Asp
1460                1465                1470

Asn Phe Lys Ser Ile Arg Glu Val Ile Leu Asp Ser Glu Gln His
1475                1480                1485

Glu Ala Thr Ala Arg Val Lys Phe Gln Ala Pro Gln Gly Asn Phe
1490                1495                1500

His Arg Asn Pro Phe Trp Ile Asp Ser Phe Gly His Leu Ser Gly
1505                1510                1515

Phe Ile Met Asn Ala Ser Asp Ala Thr Asp Ser Lys Asn Gln Val
1520                1525                1530

Phe Val Asn His Gly Trp Asp Ser Met Arg Cys Leu Lys Lys Phe
1535                1540                1545

Ser Pro Asp Val Thr Tyr Arg Thr Tyr Val Arg Met Gln Pro Trp
1550                1555                1560

Lys Asp Ser Ile Trp Ala Gly Asp Val Tyr Val Phe Asp Gly Asp
1565                1570                1575

Asp Ile Val Ala Val Tyr Gly Ala Val Lys Phe Gln Ala Leu Ser
1580                1585                1590

Arg Lys Ile Leu Asp Thr Val Leu Pro Pro Ser Arg Ala Ser Ala
```

```
            1595                1600                1605

Pro Ala  Pro Ala Lys  Pro Ala  Ala Lys Pro  Ser Ala  Pro Ser Leu
    1610             1615              1620

Val Lys  Arg Ala Leu  Thr Ile  Leu Ala Glu  Glu Val  Gly Leu Ser
    1625             1630              1635

Glu Ser  Glu Ile Thr  Asp Asp  Leu Val Phe  Ala Asp  Tyr Gly Val
    1640             1645              1650

Asp Ser  Leu Leu Ser  Leu Thr  Val Thr Gly  Arg Tyr  Arg Glu Glu
    1655             1660              1665

Leu Asp  Ile Asp Leu  Glu Ser  Ser Ile Phe  Ile Asp  Gln Pro Thr
    1670             1675              1680

Val Lys  Asp Phe Lys  Gln Phe  Leu Ala Pro  Met Ser  Gln Gly Glu
    1685             1690              1695

Ala Ser  Asp Gly Ser  Thr Ser  Asp Pro Glu  Ser Ser  Ser Ser Phe
    1700             1705              1710

Asn Gly  Gly Ser Ser  Thr Asp  Glu Ser Ser  Ala Gly  Ser Pro Val
    1715             1720              1725

Ser Ser  Pro Pro Asn  Glu Lys  Val Thr Gln  Val Glu  Gln His Ala
    1730             1735              1740

Thr Ile  Lys Glu Ile  Arg Ala  Ile Leu Ala  Asp Glu  Ile Gly Val
    1745             1750              1755

Thr Glu  Glu Glu Leu  Lys Asp  Asp Glu Asn  Leu Gly  Glu Met Gly
    1760             1765              1770

Met Asp  Ser Leu Leu  Ser Leu  Thr Val Leu  Gly Arg  Ile Arg Glu
    1775             1780              1785

Thr Leu  Asp Leu Asp  Leu Pro  Gly Glu Phe  Phe Ile  Glu Asn Gln
    1790             1795              1800

Thr Leu  Asn Asp Val  Glu Asp  Ala Leu Gly  Leu Lys  Pro Lys Ala
    1805             1810              1815

Ala Pro  Ala Pro Ala  Pro Ala  Pro Ala Pro  Val Pro  Ala Pro Val
    1820             1825              1830

Ser Ala  Pro Ile Leu  Lys Glu  Pro Val Pro  Asn Ala  Asn Ser Thr
    1835             1840              1845

Ile Met  Ala Arg Ala  Ser Pro  His Pro Arg  Ser Thr  Ser Ile Leu
    1850             1855              1860

Leu Gln  Gly Asn Pro  Lys Thr  Ala Thr Lys  Thr Leu  Phe Leu Phe
    1865             1870              1875

Pro Asp  Gly Ser Gly  Ser Ala  Thr Ser Tyr  Ala Thr  Ile Pro Gly
    1880             1885              1890

Val Ser  Pro Asp Val  Cys Val  Tyr Gly Leu  Asn Cys  Pro Tyr Met
    1895             1900              1905

Lys Thr  Pro Glu Lys  Leu Lys  Tyr Pro Leu  Ala Glu  Met Thr Phe
    1910             1915              1920

Pro Tyr  Leu Ala Glu  Ile Arg  Arg Arg Gln  Pro Lys  Gly Pro Tyr
    1925             1930              1935

Asn Phe  Gly Gly Trp  Ser Ala  Gly Gly Ile  Cys Ala  Tyr Asp Ala
    1940             1945              1950

Ala Arg  Tyr Leu Ile  Leu Glu  Glu Gly Glu  Gln Val  Asp Arg Leu
    1955             1960              1965

Leu Leu  Leu Asp Ser  Pro Phe  Pro Ile Gly  Leu Glu  Lys Leu Pro
    1970             1975              1980

Thr Arg  Leu Tyr Gly  Phe Ile  Asn Ser Met  Gly Leu  Phe Gly Glu
    1985             1990              1995
```

```
Gly Asn Lys Ala Pro Pro Ala Trp Leu Leu Pro His Phe Leu Ala
    2000            2005                2010

Phe Ile Asp Ser Leu Asp Thr Tyr Lys Ala Val Pro Leu Pro Phe
    2015            2020                2025

Asp Asp Pro Lys Trp Ala Lys Lys Met Pro Lys Thr Phe Met Val
    2030            2035                2040

Trp Ala Lys Asp Gly Ile Cys Ser Lys Pro Asp Pro Trp Pro
    2045            2050                2055

Glu Pro Asp Pro Asp Gly Lys Pro Asp Thr Arg Glu Met Val Trp
    2060            2065                2070

Leu Leu Lys Asn Arg Thr Asp Met Gly Pro Asn Lys Trp Asp Thr
    2075            2080                2085

Leu Val Gly Pro Gln Asn Val Gly Gly Ile Thr Val Ile Glu Gly
    2090            2095                2100

Ala Asn His Phe Thr Met Thr Leu Gly Pro Lys Ala Lys Glu Leu
    2105            2110                2115

Gly Ser Phe Ile Gly Asn Ala Met Ala Asn
    2120            2125

<210> SEQ ID NO 27
<211> LENGTH: 502
<212> TYPE: DNA
<213> ORGANISM: Aspergillus niger

<400> SEQUENCE: 27
tcagcgcggt aagctctaat ggcgttactg tcagcgcacc acctacggta cttgatgaat      60
tcgtcgagac ctgcatttcc aagaattaca agccagtgaa ggcccctatt catggcccgt     120
accatgcgcc acatctgtat gatgataagg atatcgaccg catcctgcag cagtcctctg     180
ctctagaagg actgaccggc tgttcacccg ttattcccat catctccagt aacactggaa     240
agccgatcaa ggccaagtcc atcaaagatc tcttcaaggt cgcactggag agatactcc      300 tacgacgact atgctgggac aaggtcacgg agtcctgcac atcagtctgc aagaccggca     360
caaaccactc ttgcaaattg tttccgatct cgagtagcgc cactcaaagt ttgttcacag     420
tcctcaagaa ggccggtgtg agcatcagct tggagactgg ggtaggagag atcgcgacga     480
acccagaaat gcggaacctt ac                                              502

<210> SEQ ID NO 28
<211> LENGTH: 166
<212> TYPE: PRT
<213> ORGANISM: Aspergillus niger

<400> SEQUENCE: 28

Ser Ala Val Ser Ser Asn Gly Val Thr Val Ser Ala Pro Pro Thr Val
1               5                   10                  15

Leu Asp Glu Phe Val Glu Thr Cys Ile Ser Lys Asn Tyr Lys Pro Val
                20                  25                  30

Lys Ala Pro Ile His Gly Pro Tyr His Ala Pro His Leu Tyr Asp Asp
            35                  40                  45

Lys Asp Ile Asp Arg Ile Leu Gln Gln Ser Ser Ala Leu Glu Gly Leu
        50                  55                  60

Thr Gly Cys Ser Pro Val Ile Pro Ile Ser Ser Asn Thr Gly Lys
65                  70                  75                  80

Pro Ile Lys Ala Lys Ser Ile Lys Asp Leu Phe Lys Val Ala Leu Glu
                85                  90                  95
```

```
Glu Ile Leu Leu Arg Arg Leu Cys Trp Asp Lys Val Thr Glu Ser Cys
            100                 105                 110

Thr Ser Val Cys Lys Thr Gly Thr Asn His Ser Cys Lys Leu Phe Pro
            115                 120                 125

Ile Ser Ser Ala Thr Gln Ser Leu Phe Thr Val Leu Lys Lys Ala
        130                 135                 140

Gly Val Ser Ile Ser Leu Glu Thr Gly Val Gly Glu Ile Ala Thr Asn
145                 150                 155                 160

Pro Glu Met Arg Asn Leu
                165

<210> SEQ ID NO 29
<211> LENGTH: 30
<212> TYPE: DNA
<213> ORGANISM: Aspergillus niger

<400> SEQUENCE: 29
ggggccatgg tcagcgcggt aagctctaat                                          30

<210> SEQ ID NO 30
<211> LENGTH: 32
<212> TYPE: DNA
<213> ORGANISM: Aspergillus niger

<400> SEQUENCE: 30
gggggcggcc gcgtaaggtt ccgcatttct gg                                       32

<210> SEQ ID NO 31
<211> LENGTH: 20
<212> TYPE: DNA
<213> ORGANISM: Aspergillus niger

<400> SEQUENCE: 31
tcgtgaatca ggtcctagcc                                                     20

<210> SEQ ID NO 32
<211> LENGTH: 22
<212> TYPE: DNA
<213> ORGANISM: Aspergillus niger

<400> SEQUENCE: 32
aaacaaccca attggtagat gc                                                  22

<210> SEQ ID NO 33
<211> LENGTH: 21
<212> TYPE: DNA
<213> ORGANISM: Aspergillus niger

<400> SEQUENCE: 33
atctgtacgg caacattgtc a                                                   21

<210> SEQ ID NO 34
<211> LENGTH: 20
<212> TYPE: DNA
<213> ORGANISM: Aspergillus niger

<400> SEQUENCE: 34
ttctgcatac ggtcggagat                                                     20

<210> SEQ ID NO 35
<211> LENGTH: 30
```

```
<212> TYPE: DNA
<213> ORGANISM: Aspergillus niger

<400> SEQUENCE: 35
ttaattaatc ggtcaatcgc cgttgtcaga                                      30

<210> SEQ ID NO 36
<211> LENGTH: 24
<212> TYPE: DNA
<213> ORGANISM: Aspergillus niger

<400> SEQUENCE: 36
aatttccaaa cagggtaact ccac                                            24

<210> SEQ ID NO 37
<211> LENGTH: 2564
<212> TYPE: DNA
<213> ORGANISM: Trichoderma reesei

<400> SEQUENCE: 37
ggacagccgg acgcaatggt gaataacgca gctcttctcg ccgccctgtc ggctctcctg     60
cccacggccc tggcgcagaa caatcaaaca tacgccaact actctgctca gggccagcct    120
gatctctacc ccgagacact tgccacgctc acactctcgt tccccgactg cgaacatggc    180
cccctcaaga caatctcgt  ctgtgactca tcggccggct atgtagagcg agcccaggcc    240
ctcatctcgc tcttcaccct cgaggagctc attctcaaca cgcaaaactc gggccccggc    300
gtgcctcgcc tgggtcttcc gaactaccaa gtctggaatg aggctctgca cggcttggac    360
cgcgccaact tcgccaccaa gggcggccag ttcgaatggg cgacctcgtt ccccatgccc    420
atcctcacta cggcggccct caaccgcaca ttgatccacc agattgccga catcatctcg    480
acccaagctc gagcattcag caacagcggc cgttacggtc tcgacgtcta tgcgccaaac    540
gtcaatggct tccgaagccc cctctggggc cgtggccagg agacgcccgg cgaagacgcc    600
tttttcctca gctccgccta tacttacgag tacatcacgg gcatccaggg tggcgtcgac    660
cctgagcacc tcaaggttgc cgccacggtg aagcactttg ccggatacga cctcgagaac    720
tggaacaacc agtcccgtct cggtttcgac gccatcaata ctcagcagga cctctccgaa    780
tactacactc cccagttcct cgctgcggcc cgttatgcaa agtcacgcag cttgatgtgc    840
gcatacaact ccgtcaacgg cgtgcccagc tgtgccaaca gcttcttcct gcagacgctt    900
ttgcgcgaga gctggggctt ccccgaatgg ggatacgtct cgtccgattg cgatgccgtc    960
tacaacgttt tcaaccctca tgactacgcc agcaaccagt cgtcagccgc cgccagctca    1020
ctgcgagccg gcaccgatat cgactgcggt cagacttacc cgtggcacct caacgagtcc    1080
tttgtggccg gcgaagtctc ccgcggcgag atcgagcggt ccgtcacccg tctgtacgcc    1140
aacctcgtcc gtctcggata cttcgacaag aagaaccagt accgctcgct cggttggaag    1200
gatgtcgtca agactgatgc ctggaacatc tcgtacgagg ctgctgttga gggcatcgtc    1260
ctgctcaaga acgatggcac tctccctctg tccaagaagg tgcgcagcat tgctctgatc    1320
ggaccatggg ccaatgccac aacccaaatg caaggcaact actatggccc tgcccccatac   1380 ctcatcagcc ctctggaagc tgctaagaag gccggctatc acgtcaactt tgaactcggc    1440
acagagatcg ccggcaacag caccactggc tttgccaagg ccattgctgc cgccaagaag    1500
tcggatgcca tcatctacct cggtggaatt gacaacacca ttgaacagga gggcgctgac    1560
cgcacggaca ttgcttggcc cggtaatcag ctggatctca tcaagcagct cagcgaggtc    1620
```

-continued

```
ggcaaacccc ttgtcgtcct gcaaatgggc ggtggtcagg tagactcatc ctcgctcaag    1680
agcaacaaga aggtcaactc cctcgtctgg ggcggatatc ccggccagtc gggaggcgtt    1740
gccctcttcg acattctctc tggcaagcgt gctcctgccg ccgactggt caccactcag     1800 tacccggctg agtatgttca ccaattcccc cagaatgaca tgaacctccg acccgatgga    1860
aagtcaaacc ctggacagac ttacatctgg tacaccggca aacccgtcta cgagtttggc    1920
agtggtctct tctacaccac cttcaaggag actctcgcca gccaccccaa gagcctcaag    1980
ttcaacacct catcgatcct ctctgctcct cacccgggat acacttacag cgagcagatt    2040
cccgtcttca ccttcgaggc caacatcaag aactcgggca agacggagtc cccatatacg    2100
gccatgctgt ttgttcgcac aagcaacgct ggcccagccc cgtacccgaa caagtggctc    2160
gtcggattcg accgacttgc cgacatcaag cctggtcact cttccaagct cagcatcccc    2220
atccctgtca gtgctctcgc ccgtgttgat tctcacggaa accggattgt ataccccggc    2280
aagtatgagc tagccttgaa caccgacgag tctgtgaagc ttgagtttga gttggtggga    2340
gaagaggtaa cgattgagaa ctggccgttg gaggagcaac agatcaagga tgctacacct    2400
gacgcataag ggttttaatg atgttgttat gacaaacggg tagagtagtt aatgatggaa    2460
taggaagagg ccatagtttt ctgtttgcaa accattttg ccattgcgaa aaaaaaaaa     2520 aaaaaaaaaa aaaaaaaaaa aaaaaaaaaa aaaaaaaaaa aaaa                    2564
```

<210> SEQ ID NO 38
<211> LENGTH: 797
<212> TYPE: PRT
<213> ORGANISM: Trichoderma reesei

<400> SEQUENCE: 38

```
Met Val Asn Asn Ala Ala Leu Leu Ala Leu Ser Ala Leu Leu Pro
1               5                   10                  15

Thr Ala Leu Ala Gln Asn Asn Gln Thr Tyr Ala Asn Tyr Ser Ala Gln
                20                  25                  30

Gly Gln Pro Asp Leu Tyr Pro Glu Thr Leu Ala Thr Leu Thr Leu Ser
            35                  40                  45

Phe Pro Asp Cys Glu His Gly Pro Leu Lys Asn Leu Val Cys Asp
    50                  55                  60

Ser Ser Ala Gly Tyr Val Glu Arg Ala Gln Ala Leu Ile Ser Leu Phe
65                  70                  75                  80

Thr Leu Glu Glu Leu Ile Leu Asn Thr Gln Asn Ser Gly Pro Gly Val
                85                  90                  95

Pro Arg Leu Gly Leu Pro Asn Tyr Gln Val Trp Asn Glu Ala Leu His
            100                 105                 110

Gly Leu Asp Arg Ala Asn Phe Ala Thr Lys Gly Gly Gln Phe Glu Trp
        115                 120                 125

Ala Thr Ser Phe Pro Met Pro Ile Leu Thr Thr Ala Ala Leu Asn Arg
    130                 135                 140

Thr Leu Ile His Gln Ile Ala Asp Ile Ile Ser Thr Gln Ala Arg Ala
145                 150                 155                 160

Phe Ser Asn Ser Gly Arg Tyr Gly Leu Asp Val Tyr Ala Pro Asn Val
                165                 170                 175

Asn Gly Phe Arg Ser Pro Leu Trp Gly Arg Gly Gln Glu Thr Pro Gly
            180                 185                 190

Glu Asp Ala Phe Phe Leu Ser Ser Ala Tyr Thr Tyr Glu Tyr Ile Thr
        195                 200                 205
```

```
Gly Ile Gln Gly Gly Val Asp Pro Glu His Leu Lys Val Ala Ala Thr
210                 215                 220
Val Lys His Phe Ala Gly Tyr Asp Leu Glu Asn Trp Asn Asn Gln Ser
225                 230                 235                 240
Arg Leu Gly Phe Asp Ala Ile Ile Thr Gln Gln Asp Leu Ser Glu Tyr
            245                 250                 255
Tyr Thr Pro Gln Phe Leu Ala Ala Arg Tyr Ala Lys Ser Arg Ser
            260                 265                 270
Leu Met Cys Ala Tyr Asn Ser Val Asn Gly Val Pro Ser Cys Ala Asn
                275                 280                 285
Ser Phe Phe Leu Gln Thr Leu Leu Arg Glu Ser Trp Gly Phe Pro Glu
290                 295                 300
Trp Gly Tyr Val Ser Ser Asp Cys Asp Ala Val Tyr Asn Val Phe Asn
305                 310                 315                 320
Pro His Asp Tyr Ala Ser Asn Gln Ser Ser Ala Ala Ser Ser Leu
                325                 330                 335
Arg Ala Gly Thr Asp Ile Asp Cys Gly Gln Thr Tyr Pro Trp His Leu
            340                 345                 350
Asn Glu Ser Phe Val Ala Gly Glu Val Ser Arg Gly Glu Ile Glu Arg
            355                 360                 365
Ser Val Thr Arg Leu Tyr Ala Asn Leu Val Arg Leu Gly Tyr Phe Asp
            370                 375                 380
Lys Lys Asn Gln Tyr Arg Ser Leu Gly Trp Lys Asp Val Val Lys Thr
385                 390                 395                 400
Asp Ala Trp Asn Ile Ser Tyr Glu Ala Ala Val Glu Gly Ile Val Leu
                405                 410                 415
Leu Lys Asn Asp Gly Thr Leu Pro Leu Ser Lys Lys Val Arg Ser Ile
            420                 425                 430
Ala Leu Ile Gly Pro Trp Ala Asn Ala Thr Thr Gln Met Gln Gly Asn
            435                 440                 445
Tyr Tyr Gly Pro Ala Pro Tyr Leu Ile Ser Pro Leu Glu Ala Ala Lys
            450                 455                 460
Lys Ala Gly Tyr His Val Asn Phe Glu Leu Gly Thr Glu Ile Ala Gly
465                 470                 475                 480
Asn Ser Thr Thr Gly Phe Ala Lys Ala Ile Ala Ala Lys Lys Ser
                485                 490                 495
Asp Ala Ile Ile Tyr Leu Gly Gly Ile Asp Asn Thr Ile Glu Gln Glu
                500                 505                 510
Gly Ala Asp Arg Thr Asp Ile Ala Trp Pro Gly Asn Gln Leu Asp Leu
            515                 520                 525
Ile Lys Gln Leu Ser Glu Val Gly Lys Pro Leu Val Val Leu Gln Met
530                 535                 540
Gly Gly Gly Gln Val Asp Ser Ser Leu Lys Ser Asn Lys Lys Val
545                 550                 555                 560
Asn Ser Leu Val Trp Gly Gly Tyr Pro Gly Gln Ser Gly Gly Val Ala
                565                 570                 575
Leu Phe Asp Ile Leu Ser Gly Lys Arg Ala Pro Ala Gly Arg Leu Val
            580                 585                 590
Thr Thr Gln Tyr Pro Ala Glu Tyr Val His Gln Phe Pro Gln Asn Asp
            595                 600                 605
Met Asn Leu Arg Pro Asp Gly Lys Ser Asn Pro Gly Gln Thr Tyr Ile
610                 615                 620
Trp Tyr Thr Gly Lys Pro Val Tyr Glu Phe Gly Ser Gly Leu Phe Tyr
```

```
625                 630                 635                 640
Thr Thr Phe Lys Glu Thr Leu Ala Ser His Pro Lys Ser Leu Lys Phe
                645                 650                 655
Asn Thr Ser Ser Ile Leu Ser Ala Pro His Pro Gly Tyr Thr Tyr Ser
                660                 665                 670
Glu Gln Ile Pro Val Phe Thr Phe Glu Ala Asn Ile Lys Asn Ser Gly
                675                 680                 685
Lys Thr Glu Ser Pro Tyr Thr Ala Met Leu Phe Val Arg Thr Ser Asn
                690                 695                 700
Ala Gly Pro Ala Pro Tyr Pro Asn Lys Trp Leu Val Gly Phe Asp Arg
705                 710                 715                 720
Leu Ala Asp Ile Lys Pro Gly His Ser Ser Lys Leu Ser Ile Pro Ile
                725                 730                 735
Pro Val Ser Ala Leu Ala Arg Val Asp Ser His Gly Asn Arg Ile Val
                740                 745                 750
Tyr Pro Gly Lys Tyr Glu Leu Ala Leu Asn Thr Asp Glu Ser Val Lys
                755                 760                 765
Leu Glu Phe Glu Leu Val Gly Glu Val Thr Ile Glu Asn Trp Pro
                770                 775                 780
Leu Glu Glu Gln Gln Ile Lys Asp Ala Thr Pro Asp Ala
785                 790                 795
```

<210> SEQ ID NO 39
<211> LENGTH: 500
<212> TYPE: DNA
<213> ORGANISM: Trichoderma reesei

<400> SEQUENCE: 39

```
acgagtttgg cagtggtctc ttctacacca ccttcaagga gactctcgcc agccacccca    60
agagcctcaa gttcaacacc tcatcgatcc tctctgctcc tcaccccgga tacacttaca   120
gcgagcagat tcccgtcttc accttcgagg ccaacatcaa gaactcgggc aagacggagt   180
cccccatatac ggccatgctg tttgttcgca aagcaacgc tggcccagcc cgtacccga   240
acaagtggct cgtcggattc gaccgacttg ccgacatcaa gcctggtcac tcttccaagc   300
tcagcatccc catccctgtc agtgctctcg cccgtgttga ttctcacgga aaccggattg   360
tatacccccgg caagtatgag ctagccttga acaccgacga gtctgtgaag cttgagtttg   420
agttggtggg agaagaggta acgattgaga actggccgtt ggaggagcaa cagatcaagg   480
atgctacacc tgacgcataa                                                500
```

<210> SEQ ID NO 40
<211> LENGTH: 166
<212> TYPE: PRT
<213> ORGANISM: Trichoderma reesei

<400> SEQUENCE: 40

```
Tyr Glu Phe Gly Ser Gly Leu Phe Tyr Thr Thr Phe Lys Glu Thr Leu
1               5                   10                  15
Ala Ser His Pro Lys Ser Leu Lys Phe Asn Thr Ser Ser Ile Leu Ser
                20                  25                  30
Ala Pro His Pro Gly Tyr Thr Tyr Ser Glu Gln Ile Pro Val Phe Thr
                35                  40                  45
Phe Glu Ala Asn Ile Lys Asn Ser Gly Lys Thr Glu Ser Pro Tyr Thr
                50                  55                  60
Ala Met Leu Phe Val Arg Thr Ser Asn Ala Gly Pro Ala Pro Tyr Pro
```

```
                65                  70                  75                  80
Asn Lys Trp Leu Val Gly Phe Asp Arg Leu Ala Asp Ile Lys Pro Gly
                85                  90                  95

His Ser Ser Lys Leu Ser Ile Pro Ile Pro Val Ser Ala Leu Ala Arg
            100                 105                 110

Val Asp Ser His Gly Asn Arg Ile Val Tyr Pro Gly Lys Tyr Glu Leu
            115                 120                 125

Ala Leu Asn Thr Asp Glu Ser Val Lys Leu Glu Phe Glu Leu Val Gly
            130                 135                 140

Glu Glu Val Thr Ile Glu Asn Trp Pro Leu Glu Glu Gln Gln Ile Lys
145                 150                 155                 160

Asp Ala Thr Pro Asp Ala
                165

<210> SEQ ID NO 41
<211> LENGTH: 26
<212> TYPE: DNA
<213> ORGANISM: Trichoderma reesei

<400> SEQUENCE: 41
ccatggtacg agtttggcag tggtct                                             26

<210> SEQ ID NO 42
<211> LENGTH: 26
<212> TYPE: DNA
<213> ORGANISM: Trichoderma reesei

<400> SEQUENCE: 42
acgcgtttat gcgtcaggtg tagcat                                             26
```